(12) United States Patent
Omenetto et al.

(10) Patent No.: US 10,126,467 B2
(45) Date of Patent: Nov. 13, 2018

(54) SIGNAL ENHANCEMENT BY SILK PHOTONIC CRYSTALS

(71) Applicant: Tufts University, Medford, MA (US)

(72) Inventors: Fiorenzo Omenetto, Wakefield, MA (US); David Kaplan, Concord, MA (US); Sunghwan Kim, Malden, MA (US)

(73) Assignee: TUFTS UNIVERSITY, Medford, MA (US)

( * ) Notice: Subject to any disclaimer, the term of this patent is extended or adjusted under 35 U.S.C. 154(b) by 0 days.

(21) Appl. No.: 14/363,216

(22) PCT Filed: Dec. 5, 2012

(86) PCT No.: PCT/US2012/068046
§ 371 (c)(1),
(2) Date: Jun. 5, 2014

(87) PCT Pub. No.: WO2013/130156
PCT Pub. Date: Sep. 6, 2013

(65) Prior Publication Data
US 2014/0334005 A1 Nov. 13, 2014

Related U.S. Application Data

(60) Provisional application No. 61/567,114, filed on Dec. 5, 2011.

(51) Int. Cl.
*G02B 1/00* (2006.01)
*B29D 11/00* (2006.01)
*B82Y 20/00* (2011.01)

(52) U.S. Cl.
CPC .......... *G02B 1/005* (2013.01); *B29D 11/0074* (2013.01); *B29D 11/00788* (2013.01);
(Continued)

(58) Field of Classification Search
CPC .................. G02B 6/29358; G02B 27/144; G02B 27/106; G02B 27/145; G02B 1/005;
(Continued)

(56) References Cited

U.S. PATENT DOCUMENTS

| 5,245,012 A | 9/1993 | Lombari et al. |
| 6,530,944 B2 | 3/2003 | West et al. |

(Continued)

FOREIGN PATENT DOCUMENTS

| WO | WO-97/08315 A1 | 3/1997 |
| WO | WO-03/056297 A2 | 7/2003 |

(Continued)

OTHER PUBLICATIONS

Written Opinion for PCT/US2012/068046, 9 pages (dated Sep. 17, 2013).

(Continued)

*Primary Examiner* — William R Alexander
*Assistant Examiner* — Henry Duong
(74) *Attorney, Agent, or Firm* — Quarles & Brady LLP

(57) ABSTRACT

The present invention provides silk photonic crystals that can be used to enhance light-induced effects. Also disclosed are biocompatible, functionalized, all-protein inverse opals and related methods.

31 Claims, 23 Drawing Sheets

Specification includes a Sequence Listing.

(52) U.S. Cl.
CPC ...... *B29K 2089/00* (2013.01); *B29K 2833/12* (2013.01); *B29K 2995/0018* (2013.01); *B82Y 20/00* (2013.01); *Y10S 977/773* (2013.01)

(58) Field of Classification Search
CPC .......... H04B 10/25133; B29D 11/0074; B29D 11/00788; B82Y 20/00; Y10S 977/773; B29K 2089/00; B29K 2833/12; B29K 2995/0018
USPC ........................................................ 359/577
See application file for complete search history.

(56) References Cited

U.S. PATENT DOCUMENTS

| | | | |
|---|---|---|---|
| 6,685,730 B2 | 2/2004 | West et al. | |
| 6,902,932 B2 | 6/2005 | Altman et al. | |
| 7,635,755 B2 | 12/2009 | Kaplan et al. | |
| 2002/0103517 A1* | 8/2002 | West ................... | A61K 41/0052 607/88 |
| 2007/0187862 A1 | 8/2007 | Kaplan et al. | |
| 2010/0046902 A1 | 2/2010 | Kaplan et al. | |
| 2010/0120116 A1 | 5/2010 | Kaplan et al. | |
| 2011/0285991 A1* | 11/2011 | Dal Negro ........... | G01N 21/253 356/301 |
| 2012/0218653 A1* | 8/2012 | Liu ........................ | G02B 1/005 359/868 |

FOREIGN PATENT DOCUMENTS

| | | |
|---|---|---|
| WO | WO-04/000915 A2 | 12/2003 |
| WO | WO-041062697 A2 | 7/2004 |
| WO | WO-05/000483 A1 | 1/2005 |
| WO | WO-05/012606 A2 | 2/2005 |
| WO | WO-05/123114 A2 | 12/2005 |
| WO | WO-2007/016524 A2 | 2/2007 |
| WO | WO-2008/118133 A2 | 10/2008 |
| WO | WO-2008/127401 A2 | 10/2008 |
| WO | WO-2008/127403 A2 | 10/2008 |
| WO | WO-2008/127405 A2 | 10/2008 |
| WO | WO-2008/140562 A2 | 11/2008 |
| WO | WO-2008/150861 A1 | 12/2008 |
| WO | WO-2009/061823 A1 | 5/2009 |
| WO | WO-2009/140588 A1 | 11/2009 |
| WO | WO-2010/065957 A2 | 6/2010 |
| WO | WO-2010/141133 A2 | 12/2010 |
| WO | WO-2011/006133 A2 | 1/2011 |
| WO | WO-2011/008842 A2 | 1/2011 |
| WO | WO-2011/130335 A2 | 10/2011 |
| WO | WO-2011150231 A2 | 12/2011 |

OTHER PUBLICATIONS

Swinerd et al, Silk Inverse Opals from Template-Directed B-Sheet Transformation of Regenerated Silk Fibroin, Soft Matter, 3(11):1377-1380 (2007).
International Search Report for PCT/US2012/068046, 3 pages (dated Sep. 17, 2013).
Alivisatos, P., The use of nanocrystals in biological detection, Nat. Biotechnol., 22(1):47-52 (2004).
Amsden, J.J. et al., Rapid nanoimprinting of silk fibroin films for biophotonic applications, Adv. Mater., 22(15):1746-9 (2010).
Amsden, J.J. et al., Spectral analysis of induced color change on periodically nanopatterned silk films, Opt. Express, 17(23):21271-9 (2009).
Bini, E. et al., Mapping domain structures in silks from insects and spiders related to protein assembly, Journal of Molecular Biology, 335(1):27-40 (2004).
Demura et al., Immobilization of peroxidase with a Bombyx mori silk fibroin membrane and its application to biophotosensors, J. Biotechnol., 10:113-120 (1989).
Domachuk, P. et al., Bioactive "self-sensing" optical systems, Applied Physics Letters, 95(25):253702 (2009).
Gupta, et al., Fabrication and Characterization of Silk Fibroin-derived Curcumin Nanoparticles for Cancer Therapy, International Journal for Nanomedicine, 4:115-122 (2009).
Hirsch, L.R. et al., Nanoshell-mediated near-infrared thermal therapy of tumors under magnetic resonance guidance, Proc. Natl. Acad. Sci. U S A., 100(23):13549-54 (2003).
Hsia, T.Y. et al., Novel minimally invasive, intrapericardial implantable cardioverter defibrillator coil system: a useful approach to arrhythmia therapy in children, Ann. Thorac. Surg., 87(4):1234-8 (2009).
Jaeger, G. et al., Two years follow-up study of the pain-relieveing effect of gold bead implantation in dogs with hip-joint arthritis, Acta Veterinaria Scandinavica, 49(9):pp. 1-7 (2007).
Jin, H.J. and Kaplan, D.L., Mechanism of silk processing in insects and spiders, Nature 424(6952):1057-1061 (2003).
Jin, H.J. et al., Water-Stable Silk Films with Reduced β-Sheet Content, Advanced Functional Materials, 15:1241-1247 (2005).
Kikuchi, Y. et al., Structure of the Bombyx mori fibroin light-chain-encoding gene: upstream sequence elements common to the light and heavy chain, Gene, 110(2)1 51-8 (1992).
Lawrence, B.D. et al., Bioactive silk protein biomaterial systems for optical devices, Biomacromolecules, 9:1214-1220 (2008).
Leal-Egana, A. and Scheibel, T., Silk-based materials for biomedical applications, Biotechnology and Applied Biochemistry, 55(3):155-167 (2010).
Lucas, F. et al., The Silk Fibroins, Silk Department, Shirley Institute, Manchester, England, 13:107-242 (1958).
Maisch, T. et al., The role of singlet oxygen and oxygen concentration in photodynamic inactivation of bacteria, Proc. Natl. Acad. Sci. U S A, 104(17):7223-8 (2007).
McAlister, F.A. et al., Cardiac resynchronization therapy and implantable cardiac defibrillators in left ventricular systolic dysfunction, Evid. Rep. Technol. Assess. (Full Rep)., (152):1-199 (2007).
Nazarov, et al., Porous 3-D Scaffolds from Regenerated Silk Fibroin, Biomacromolecules, 5:718-726 (2004).
Omenetto, F. and Kaplan, D., A new route for silk, Nature Photonics, 2:641-643 (2008).
Omenetto, F.G. and Kaplan, D.L., New Opportunities for an Ancient Material, Science, 329:528-531 (2010).
Parker, S. et al., Biocompatible Silk Printed Optical Waveguides, Advanced Materials, 21:1-5 (2009).
Perry, H. et al., Nano- and Micropatterning of Optically Transparent, Mechanically Robust, Biocompatible Sillk Fibroin Films, Advanced Materials, 20:3070-3072 (2008).
Scheibel, T., Spider silks: recombinant synthesis, assembly, spinning, and engineering of synthetic proteins, Microb. Cell Fact., 3(1):14 (2004).
Stewart, M.E. et al., Quantitative multispectral biosensing and 1D imaging using quasi-3D plasmonic crystals, Proc. Natl. Acad. Sci. U S A., 103(46):17143-8 (2006).
Takei, F. et al., Further Evidence for Importance of the Subunit Combination of Silk Fibroin in its Efficient secretion from the Posterior Silk Gland Cells, J Cell Biol. 105: 175-180 (1987).
Tan, Y. et al., Gold-nanoparticle-infiltrated polystyrene inversopals: A Three-dimensional platform for generating combined optical properties. Chem. Mater 18(15): 3385-3389 (2006).
Tanaka, K. et al., Determination of the site of disulfide linkage between heavy and light chains of silk fibroin produced by Bombyx mori, Biochimica et Biophysica Acta, 1432:92-103 (1999).
Tanaka, K. et al., Immunological identification of the major disulfide-linked light component of silk fibroin, Journal of Biochemistry, 114(1):1-4 (1993).
Valluzzi, R., et al., Orientation of silk III at the air-water interface, Int. J. Biol. Macromol., 24(2-3): 237-242 (1999).
Wijnhoven, J.E.G.J. and Vos, W.L., Preparation of photonic crystals made of air spheres in titania, Science, 281(5378):802-4 (1998).
Yablonovitch, E. et al., Inhibited spontaneous emission in solid-state physics and electronics, Phys. Rev. Lett., 58(20):2059-2062 (1987).
Zhang, Y-Q et al., Formation of silk fibroin nanoparticles in water-miscible organic solvent and their characterization, Journal of Nanoparticle Research, 9:885-900 (2007).

(56) References Cited

OTHER PUBLICATIONS

Zhou, C.Z. et al, Fine organization of Bombyx mori fibroin heavy chain gene, Nucleic Acids Research, 28(12):2413-2419 (2000).
Asher, S.A. et al., Polymerized crystalline colloidal array chemical-sensing materials for detection of lead in body fluids, Anal. Bioanal. Chem., 373(7):632-8 (2002).
Bonifacio, L.D. et al., Towards the photonic nose: a novel platform for molecule and bacteria identification, Adv. Mater., 22(12):1351-4 (2010).
Chung, P.Y. et al., Multispectral Refractive Index Sensing Using Surface Plasmon Resonance on Gold Nanoslits, Mater. Res. Soc. Sym. Proc., vol. 1253, 1253-K10-26, 6 pages (2010).
Dahlin, A. et al., Localized surface plasmon resonance sensing of lipid-membrane-mediated biorecognition events, J. Am. Chem. Soc., 127(14):5043-8 (2005).
Ding, B. et al., Three-dimensional photonic crystals with an active surface: Gold film terminated opals, Phys. Rev. B, 82: 035119, 9 pages (2010).
Dong et al., Biogenic synthesis of hierarchical hybrid nanocomposites and patterning of silver nanoparticles, Mats. Chem. Phys., 110:160 (2008).
Elman, N.M., et al., An implantable MEMS drug delivery device for rapid delivery in ambulatory emergency care, Biomed. Microdevices, 11(3):625-31 (2009).
Florescu, M. et al., Thermal emission and absorption of radiation in finite inverted-opal photonic crystals, Phys. Rev. A, 72: 033821 (2005).
Ganesh, N. et al., Near ultraviolet-wavelength photonic-crystal biosensor with enhanced surface-to-bulk sensitvity ratio, Appl. Phys. Lett., 89: 023901 (2006).
Hamblin, M.R. and Demidova, T.N., Mechanisms of low level light therapy, Proc. SPIE 6140, Mechanisms for Low-Light Therapy, 614001 (Feb. 10, 2006).
Hilt, J.Z. and Peppas, N.A., Microfabricated drug delivery devices, Int. J. Pharm., 306(1-2):15-23 (2005).
Jain, P.K. et al., Noble metals on the nanoscale: optical and photothermal properties and some applications in imaging, sensing, biology, and medicine, Acc. Chem. Res., 41(12):1578-86 (2008).
Jaremko, J. and Rorstad, O., Advances toward the implantable artificial pancreas for treatment of diabetes, Diabetes Care., 21(3):444-50 (1998).
Kim, S. et al., Fiber-coupled surface-emitting photonic crystal band edge laser for biochemical sensor applications. Appl. Phys. Lett. 94: 133503 (2009).
Kim, S. et al., Silk inverse opals. Nature Photon. 6: 818-823 (2012).
Kim, S.-H. et al., Self-assembled colloidal structures for photonics, NPG Asia Mater., 3:25-33 (2011).
Kim, U-J. et al., Structure and Properties of Silk Hydrogels, Biomacromol., 5:786-792 (2004).
Lal, S. et al., Nanoshell-enabled photothermal cancer therapy: impending clinical impact, Acc. Chem. Res., 41(12):1842-51 (2008).
Lu, Q. et al., Stabilization and release of enzymes from silk films, Macromol. Biosci., 10(4):359-68 (2010).
Lu, X. et al., Chemical synthesis of novel plasmonic nanoparticles, Annu. Rev. Phys. Chem., 60:167-92 (2009).
Lu, Y. and Chen, S.C., Micro and nano-fabrication of biodegradable polymers for drug delivery, Adv. Drug. Deliv. Rev., 56(11):1621-33 (2004).
Mobbs, R.J. et al., Peripheral nerve stimulation for the treatment of chronic pain, J. Clin. Neurosci., 14(3):216-21; discussion 222-3 (2007).
Morandi, C. et al., Light localization effect on the optical properties of opals doped gold nanoparticles, J. Phys. Chem. C., 112:6293-6298 (2008).
Narazaki, G. and Yamashita, J.K., Creations of biological Pacemaker, Inflammation and Regeneration, 29(2):123-127 (2009).
Offermans, P. et al., Universal scaling of the figure of merit of plasmonic sensors, ACS Nano., 5(6):5151-7 (2011).
Oskooi, A. F. et al., MEEP: A flexible free-software package for electromagnetic simulations by the FDTD method, Camp. Phys. Commun., 181:687-702 (2010).
Pan, G. et al., Polarization dependence of crystalline colloidal array diffraction, J. Appl. Phys., 84:83-86 (1998).
Prodan, E. et al., Electronic Structure and Optical Properties of Gold Nanoshells, Nano Letters, 3(10):1411-1415 (2003).
Qin, Z. and Bischof, J.C., Thermophysical and biological responses of gold nanoparticle laser heating, Chem. Soc. Rev., 41(3):1191-217 (2012).
Schroden, R.C. et al., Optical Properties of Inverse Opal Photonic Crystals, Chem. Mater., 14:3305-3315 (2002).
Singh, N. et al., Advances in the treatment of Parkinson's disease, Progress in Neurobiology, 81:29-44 (2007).
Stolik, S. et al., Measurement of the penetration depths of red and near infrared light in human "ex vivo" tissues, J. Photochem. Photobiol. B., 57(2-3):90-3 (2000).
Sánchez-Sobrado, O. et al., Interplay of resonant cavity modes with localized surface plasmons: optical absorption properties of Bragg stacks integrating gold nanoparticles, Adv. Mater., 23(18):2108-12 (2011).
Tarhan, I.I. and Watson, G.H, Photonic band Structure of fcc colloidal crystals, Phys. Rev. Lett. 76(2): 315-318 (1996).
Vos, W.L. et al., Strong effects of photonic band structures on the diffraction of colloidal crystals, Phys. Rev. B. Condens. Matter., 53(24):16231-16235 (1996).
Xia, Y. et al., Monodispersed colloidal spheres: old materials with new applications, Adv. Mater., 12:693-713 (2000).
Jain, P.K. et al, Calculated Absorption and Scattering Properties of Gold Nanoparticles of Different Size, Shape, and Composition: Applications in Biological Imaging and Biomedicine, J. Phys. Chem. B., 110(14): 7238-7248 (2006).
Kharlampieva, E. et al., Silk-based Mechanically Robust Ultrathin Nanocomposites with Tailored Optical Properties, Polymeric Materials: Science & Engineering, 101:1059 (2009).
Maria, J. et al., Optimization of 3D Plasmonic Crystal Structures for Refractive Index Sensing, J. Phys. Chem. C, 113:10493-10499 (2009).
Oldenburg, S. J. et al., Infrared extinction properties of gold nanoshells, Appl. Phys. Lett., 75(19): 2897-2899 (1999).
Oldenburg, S. J. et al., Nanoengineering of optical resonances, Chemical Physics Letters, 288: 234-247 (1998).
Staples, M. et al., Application of Micro- and Nano-Electromechanical Devices to Drug Delivery, Pharm. Res., 23(5):847-63 (2006).

\* cited by examiner

US 10,126,467 B2

SIGNAL ENHANCEMENT BY SILK PHOTONIC CRYSTALS

RELATED APPLICATIONS

This application claims the benefit of and priority to U.S. Provisional Application No. 61/567,114 filed Dec. 5, 2011, this application is a 35 U.S.C. § 371 National Stage of International Application No. PCT/US2012/068046, filed Dec. 5, 2012, entitled "Signal Enhancement by Silk Photonic Crystals", the entire contents of each of which are herein incorporated by reference.

GOVERNMENT SUPPORT

This invention was made with government support under grant W911NF-07-1-0618 awarded by the United States Army, Army Research Office. The U.S. government has certain rights in the invention.

BACKGROUND

Photonic crystals include periodically repeating internal regions of high and low dielectric constants. Photons propagate through the structure based upon the wavelength of the photons. Photons with wavelengths of light that are allowed to propagate through the structure are called "modes," while photons with wavelengths of light that are not allowed to propagate are called "photonic band gaps." The structure of the photonic crystals define allowed and forbidden electronic energy bands, resulting in spectral selectivity of light.

SUMMARY

The present invention relates to silk-based engineering of structural colors and encompasses the recognition that photonic crystals made from silk fibroin can be used to enhance a wide array of light-induced phenomena. Among other things, the present application provides evidence that silk-based photonic crystals can be combined with one or more functional components that are reactive to light stimulation and augment light-induced effects, including, for example, plasmonic resonance, photosensitive reactions, light emission by quantum dots and fluorescent entities, and so on.

Structural colors are colors caused by interference effects rather than by pigments. Structural color is caused by the interaction of light with structures of nanoscale periodic structure, with geometries on the order of magnitude of visible light wavelengths. Light that encounters these minute structures is subject to optical phenomena including thin film interference, multilayer interference, diffraction grating effects, photonic crystal effects, and light scattering. These phenomena lead to selective reflection of particular light wavelengths through constructive and destructive interference. Among other things, the present application encompasses the recognition that silk materials can be structurally manipulated to diffract light of particular wavelengths, resulting in perceived color. For example, a silk film can be formed around materials arranged in a lattice. The materials of the lattice can be removed, thereby leaving voids in the silk film (e.g., inverse "mould"). In some embodiments, solvents, such as organic solvents, may be used to remove the materials from the silk "mould." The resulting silk matrix (e.g., silk film) can diffract light whose wavelengths depend upon, among other things, characteristics of the voids in the lattice. In some embodiments, such silk matrix (e.g., silk film) can diffract light of different wavelengths when immersed in a substance, such as acetone. As silk can be biocompatible and/or biodegradable, silk-based materials such as silk films as disclosed herein can be used in applications requiring colorant without the introduction of potential harmful or reactive dyes.

Among other things, the present application encompasses the recognition that silk materials capable of exhibiting structural colors can be manipulated to respond to light projected onto a surface of the silk materials with an increase in signals/signal sensing induced by photons. Data presented in the present application provide evidence that silk photonic crystal can be used to augment photon-based functionalization of devices. Applications for such signal augmentation effectuated by silk photonic crystals are not limited to particular use. Rather, the invention is useful for a wide variety of applications that involve photon-based phenomena, such as light-induced signals and reactions. For instance, light-induced signals may comprise generating heat (increased temperature), activation of photosensitive reactions, and so on.

In some embodiments, such functionalization includes light-induced heat generation by the use of a plasmonic component incorporated on and/or in silk photonic crystals. Exemplary embodiments include a silk fibroin solution with, for example, gold nanoparticles dispersed therein can be used to form a silk film around materials arranged in a lattice. The materials arranged in a lattice can be removed, thereby leaving voids in the silk film. The resulting structure of the silk film (i.e., silk photonic crystal) can enhance the absorption of energy by the gold nanoparticles. In some examples, such silk films can be placed on or within a living organism (e.g., the human body), and light can be projected onto the silk film to produce heat in vivo. Such technology provides a wide variety of applications, including clinical applications, such as laser-based thermal therapy.

The invention also encompasses the recognition that silk photonic crystals (e.g., SIO) can be manipulated to respond to light projected onto a surface of the silk materials resulting in enhanced effects of photosensitive compounds (e.g., photosensitizers), such as porphyrins. The invention thus includes a means of light-induced cell killing effectuated by silk photonic crystals coupled to photosensitive compounds that produce reactive oxygen species in response to light.

One aspect of the invention relates to a method for fabricating silk crystal photonics. The method may include preparing a silk fibroin solution. The method may comprise nano-sized particles assembled into a lattice. In some embodiments, the method includes inducing a plurality of poly(methyl methacrylate) units to self-assemble into a lattice. The method may include applying the silk fibroin solution to the lattice such that the silk fibroin solution fills voids between the a plurality of nano-sized particles, such as poly(methyl methacrylate) units. The method may include drying the silk fibroin solution into a silk matrix (e.g., silk film). The method may include removing the plurality of nano-sized particles, such as poly(methyl methacrylate) units, such that the dried silk matrix that filled the voids remain, forming a silk photonic crystal.

In some embodiments, inducing a plurality of poly(methyl methacrylate) units to self-assemble into the lattice may include casting a solution with the a plurality of poly(methyl methacrylate) units onto a substrate. In some embodiments, substrate may be a silicon wafer. In some embodiments, where silicon wafer is used as a substrate, the process may include applying heat to the silicon wafer. In some embodiments, applying the heat to the silicon wafer may include setting a hot plate to apply heat at 90° C. to the silicon wafer. In some embodiments, drying the silk fibroin solution into the silk film may include drying the silk fibroin solution for twenty four hours at room temperature. In some embodiments, removing the plurality of poly(methyl methacrylate) units may include soaking the silk film and the lattice of the plurality of poly(methyl methacrylate) units in a solvent that dissolve the lattice material. In some embodiments, useful solvents include organic solvents. In some embodiments, useful organic solvents include ketone-based solvents, such as acetone.

In some embodiments, the method may include preparing an aqueous solution with plasmonic nanoparticles. In some embodiments, useful plasmonic nanoparticles include gold nanoparticles, and combining the silk fibroin solution with the aqueous solution with the gold nanoparticles. In some embodiments, the method may include immersing the silk film in a substance to alter the photonic band gap of the apparatus.

Thus, the inclusion of plasmonic nanoparticles in a silk matrix (e.g., silk fibroin matrix) as described herein provides additional utility and opportunities for silk fibroin-based bio-electronics and photonics devices through temperature/heat control. Importantly, silk fibroin can be loaded with higher concentrations of plasmonic nanoparticles than other currently existing polymers, thus allowing more heat generation. Additionally, silk fibroin is a superior dispersion medium, avoiding nanoparticle aggregation that is often problematic in other systems. Advantageously, the silk fibroin-based photothermal element can be entirely or partially biodegradable and biocompatible.

One aspect of the invention relates to an apparatus. The apparatus may include a silk matrix (e.g., silk film) with "spherical" voids arranged in a lattice. It should be appreciated that the term "spherical" as used in the context of the structure of a lattice or silk-matrix described herein is not intended to mean necessarily geometrically spherical. Rather, for example, "spherical voids" are aligned pattern of spaces generated by lattice formation. The silk film may exhibit structural color by reflecting light of frequencies within a photonic bandgap of the apparatus. The spherical voids may be arranged in a face-centered cubic structure. The spherical voids may each have a diameter ranging between about 200 nm and 400 nm. In some embodiments, spherical voids may each have a diameter of about 240 nm, about 250 nm, about 280 nm, about 300 nm, about 320 nm, or about 350 nm. The lattice may have a lattice constant of about 240 nm or about 300 nm.

One aspect of the invention relates to a method for fabricating functionalized silk photonic crystal. The method may include a step of preparing a silk fibroin solution. The method may include a step of preparing a solution with plasmonic nanoparticles. In some embodiments, the method includes a step of preparing a solution with gold nanoparticles. The method may include a step of combining the silk fibroin solution with the solution with the plasmonic nanoparticles, such as gold nanoparticles, to produce a silk fibroin solution with the nanoparticles. The method may include inducing a plurality of poly(methyl methacrylate) units to self-assemble into a lattice. The method may include applying the silk fibroin solution with the nanoparticles to the lattice such that the solution fills voids between the plurality of poly(methyl methacrylate) units. The method may include drying the silk fibroin solution with the nanoparticles into a silk film, which forms an inverse mould. The method may include removing the poly(methyl methacrylate) units.

The method may include a step of projecting a laser light onto the silk film to induce heat within the silk film. The laser light may induce an increase in temperature of about 2-50° C., about 3-45° C., about 4-30° C., about 5-20° C., about 6-10° C., about 6-8° C., about 7° C. Projecting the laser light onto the silk film may include projecting light at a wavelength of about 520 nm to about 560 nm. In some embodiments, suitable wavelength is about 532 nm. Projecting the laser light onto the silk film may include projecting light at a wavelength of about 546 nm.

BRIEF DESCRIPTION OF THE DRAWING

The following figures depict certain illustrative implementations of the methods and systems described herein, where like reference numerals refer to like elements. Each depicted implementation is illustrative of the methods and systems and should not be construed to be limiting.

DETAILED DESCRIPTION OF CERTAIN EMBODIMENTS

Figure 1:
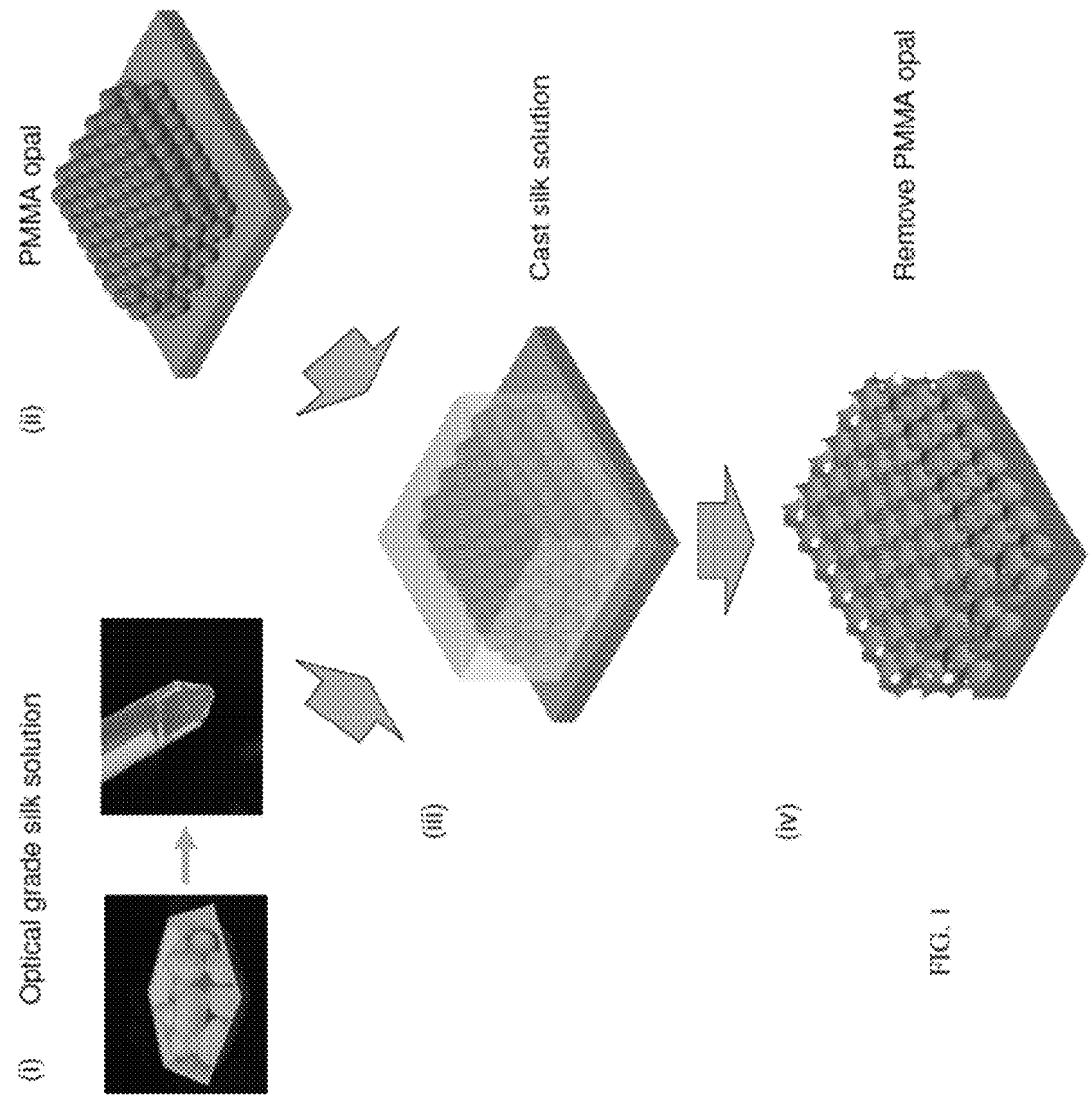
FIG. 1 depicts exemplary fabrication steps of a silk inverse opal (SIO) film. (i) Optical grade silk fibroin solution is obtained from the cocoons of the *Bombyx mori* silkworm. (ii) A PMMA opal, with sphere diameters of 250, 320, and 350 nm, is generated on silicon substrate. (iii) The opal on silicon is infiltrated with the silk fibroin solution (iv) After drying, silk film is removed from the silicon wafer. The PMMA spheres in the free-standing silk film are dissolved in acetone. A nitrogen blower is used to remove the acetone in the voids in obtained SIO film.

The present invention relates to engineering of silk photonic crystals that exhibit structural colors. In particular, the invention describes silk photonic crystals characterize by having inverse opal lattice (i.e., "silk inverse opal," or SIO). Structural colors are colors caused by interference effects rather than by pigments. The invention is drawn to the use of silk materials to fashion silk photonic crystals having structural colors, and applications thereof. In particular, as described in more detail below, silk photonic crystals described herein can be effectively employed to augment a wide range of photonic phenomenon and detection thereof. Thus, silk photonic crystals described in the present application are useful for a number of applications where it is desirable to enhance or amplify light-induced effects.

Based at least in part on this recognition, one aspect of the invention includes apparatus that incorporates light-enhancing features of silk photonic crystals. Thus, silk photonic crystals are employed to functionally enhance a light-induced effect of a light-responsive entities/elements. In the context of the present application, "light-induced effect" may mean any optic or photonic phenomena, events and/or reactions triggered by electromagnetic radiation (e.g., light). "Enhancement" means that a light-induced effect (e.g., reaction, event, phenomenon, etc.) elicited by a light-responsive component of the apparatus is amplified or augmented when coupled to the silk photonic crystals described herein, In some embodiments, light-induced effects include but are not limited to: absorption, excitation, emission, refraction, reflection, diffraction, heat generation, as well as light-sensitive chemical reactions.

Accordingly, in some embodiments, provided apparatus comprises a silk photonic crystal structurally coupled to a component that is a light responsive entity.

As used herein, the phrase "light-responsive (or 'photo-responsive') entities (or 'elements')" refer to any entities that, in response to a light stimulation (e.g., photon), elicit a light-induced effect, i.e., particular response or effect in a light-dependent fashion. The terms "light-sensitive" entities and "photosensitive" entities (or elements) may also be used interchangeably.

In some embodiments, light-responsive entities include materials that exhibit surface plasmon resonance. These materials may be refer to as plasmonic materials (e.g., plasmonic crystals). The plasmonic material typically comprises at least one metal. In some embodiments, a useful plasmonic material is typically a metal or an alloy, or is doped with at least one metal or an alloy. Such metal can be any art-recognized metal in that excitation of surface plasmon can be induced by light. In some embodiments, the metal can be a noble metal, including, but not limited to, gold, silver, ruthenium, rhodium, palladium, osmium, iridium, and platinum. Depending on the application, in some embodiments, the noble metal can possibly be mercury. In some embodiments, useful metal can be a non-noble metal, such as titanium, aluminum, nickel, fluorine, cerium, tin, bismuth, antimony, molybdenum, chromium, cobalt, zinc, tungsten, polonium, rhenium and copper. In some embodiments, the plasmonic materials can comprise oxides of noble or non-noble metals. In some embodiments, the plasmonic materials can comprise alloys of noble metals and/or non-noble metals, or nonhomogeneous mixtures of such metals. In some embodiments, the plasmonic materials can comprise silica or silk fibroin doped with rare earth emitters, such as Pr+3, Er+3, or Nd+3. See, e.g., U.S. Pat. No. 6,530,944. It should be understood that any of the above provided plasmonic materials may be in a form of oxides.

It should be noted that such plasmonic materials, used as light-responsive entities in the context of the present application, may be in a variety of structural forms. For example, in some embodiments, useful plasmonic materials are in a form of plasmonic nanoparticles. In some embodiments, useful plasmonic materials are in a form of thin films. In some embodiments, a thin film comprises a plurality of nanoparticles that are evenly distributed to form the thin film. In some embodiments, useful plasmonic materials are in a form of three-dimensional structures.

In any of the above described embodiments that involve plasmonic materials used as light-responsive entities of provided apparatus described herein, it may be desirable to design such an apparatus such that a band edge of the silk photonic crystal substantially overlaps (or matches) with a range of wavelengths that induces a light-induced effect in the light responsive entity. In this way, it is possible to optimize signal enhancement rendered by silk photonic crystals.

In some embodiments, light-responsive entities are so-called photosensitizers, which broadly encompass light-activated compounds. Photosensitizers typically include porphyrins, chlorophylls and dyes. Examples include, but are not limited to: aminolevulinic acid (ALA), Silicon Phthalocyanine Pc 4, m-tetrahydroxyphenylchlorin (mTHPC), and mono-L-aspartyl chlorin e6 (NPe6). Several photosensitizers are commercially available for clinical use, such as Allumera, Photofrin, Visudyne, Levulan, Foscan, Metvix, Hexvix, Cysview, and Laserphyrin, with others in development, e.g., Antrin, Photochlor, Photosens, Photrex, Lumacan, Cevira, Visonac, BF-200 ALA, Amphinex, and Azadipyrromethenes.

In any of the embodiments that involve photosensitizers used as light-responsive entities of provided apparatus described herein, it may be desirable to design such an apparatus such that a band edge of the silk photonic crystal substantially overlaps (or matches) with a range of wavelengths that induces a light-induced effect in the light responsive entity. In this way, it is possible to optimize signal enhancement rendered by silk photonic crystals.

In the context of the present invention, "coupling" of silk photonic crystals with a light-responsive element/entity refers to the structural integration of silk photonic crystals with the light-responsive entity such that a light-induced effect of the light-responsive entity may be enhanced by the silk photonic crystals. Thus, the structural integration effectuates functional augmentation. Such integration or coupling may be achieved by any known means. In some embodiments, a light-responsive element is incorporated within a silk photonic crystal structure. This may be achieved by, for example, doping of silk materials with the light-responsive element to form silk photonic crystals that incorporate the light-responsive entity. For example, plasmonic nanoparticles and/or photo-sensitive compounds may be incorporated into silk photonic crystals. Alternatively or additionally, in some embodiments, a light-responsive element is overlaid upon silk photonic crystal so as to be in close proximity (e.g., in contact) with one another. For example, in some embodiments, a thin layer of light-responsive materials such as plasmonic materials can be used to "coat" silk photonic crystals. In some embodiments, a thin layer of light-responsive materials comprises a plurality of nanoparticles that are light-responsive.

As explained in further detail herein, functional integration or coupling of silk photonic crystals and a light-responsive element (or entities) can be tuned to provide optimal enhancement of light-induced effect (e.g., signals) by adjusting effective wavelengths of incident light to the nanostructures of the photonic crystals.

According to the present invention, useful silk photonic crystals are provided in a form of silk lattice matrices. In some embodiments, such matrices comprise silk inverse opal ("SIO"). In some embodiments, SIO is a three-dimensional lattice matrix.

In some embodiments, SIO described in the present application exhibit a green structural color, in and around the range of about 500-550 nm in wavelength, e.g., about 500 nm, about 505 nm, about 510 nm, about 515 nm, about 520 nm, about 525 nm, about 530 nm, about 532 nm, about 535 nm, about 540 nm, about 545 nm, about 550 nm.

In some embodiments, lattice constant of useful SIO described in the present application is in a range of about 50 nm to about 1000 nm, e.g., about 200 nm to about 800 nm. For example, lattice constant may be between about 50 nm and about 200 nm, between about 200 nm and about 300 nm, between about 200 nm and about 400 nm, between about 300 nm and about 600 nm, between about 400 nm and about 700 nm, between about 400 nm and about 800 nm, between about 500 nm and about 700 nm, between about 500 nm and about 600 nm, between about 450 nm and about 650 nm, between about 300 nm and about 1000 nm, between about 500 nm and about 1000 nm.

Exemplary methods for the fabrication of useful SIO are provided herein. In some embodiments, silk solutions are used to cast over a lattice of material units aligned to produce structural colors, thereby forming an inverse mould of the lattice structure. Upon removal of the lattice from the silk, the resulting silk film (e.g., SIO) provides structural colors.

According to the invention, purified silk proteins (e.g., silk fibroin) provide desirable materials features. Silk, the natural protein produced by spiders and caterpillars, has unique and outstanding material properties. Due to its biocompatibility and capability for water-based processing, silk can be useful for biomedical applications.

Fibroin is a type of structural protein produced by certain spider and insect species that produce silk. In addition to its outstanding biocompatibility, silk fibroin matrices have excellent mechanical and optical properties, which make these materials well suited for a variety of implantable medical devices (IMDs). See, for example, Omenetto & Kaplan, 2 Nature Photonics 641 (2008). Silk fibers, such as those produced by silkworms or spiders, can be processed into silk fibroin which can then be processed into various forms including silk solutions (Jin & Kaplan, 424 Nature 1057 (2003)), gels (Jim et al., 5 Biomacromol. 786 (2004)), foams (Nazarov et al., 5 Biomacromol. 718 (2004)), and films (Jin et al., 15 Adv. Functional Mats. 1241 (2005);

Amsden et al., 17 Optics Express 21271 (2009)). Various processing options enable its use as a supporting and packaging material for implanted micro medical devices. Additionally, silk films can be patterned (in both 2D and 3D) to realize a number of optical elements such as diffractive gratings (Amsden et al., 22 Adv. Mats. 1746 (2010)), and wave guides (Parker et al., 21 Adv. Mats. 1 (2009)), within the IMDs.

Furthermore, silk films provide a biologically favorable microenvironment that allow to entrain various biological and/or chemical dopants and maintain their functionality. Proteins (Bini et al., 335 J. Mol. Bio. 27 (2004)), enzymes (Lu et al., 10 Macromol. Biosci. 359 (2010)) and small organics (Lawrence et al., 9 Biomacromol. 1214 (2008)), have been incorporated into silk films for various biochemical functionalities.

The term "biocompatible" as used herein refers in general to materials that are not harmful to the environment or to the subject: the environment can be an in vivo environment or an environment outside the body, for example, in a crop field.

As used herein, the term "biodegradable" refers in general to materials that have a chemical structure that can be altered by common environmental chemistries (e.g., enzymes, pH, and naturally-occurring compounds), including the physiological environment within a human, to yield elements or simple chemical structures, without harm thereto. Biodegradable materials can also be bioerodible.

By the term "bioerodible" means that the material is biodegradable, digestible, or erodible or otherwise dissolvable or degradable in the environment to a form where the material is diminished in size, for example, by chemical, biological (e.g., enzymatic), physical dissolution, or solubilization, to allow elimination of the material from the environment without substantial harm. In some embodiments, the term "biodegradable" as used herein, also encompasses the term "bioresorbable", which generally describes a material that decomposes under physiological conditions to break-down products that can undergo bioresorption into the host subject, e.g., becoming metabolites of the biochemical systems of the host subject. Thus, in some embodiments, the silk fibroin-based IMDs of the present invention need not be retrieved, because they are capable of degrading or eroding into materials or components that are not harmful to the subject.

Additionally, silk fibroin can be prepared in an all-aqueous process, further expanding its compatibility with biologics and the environment.

As used herein, the term "silk fibroin" includes silkworm fibroin and insect or spider silk protein. See e.g., Lucas et al., 13 Adv. Protein Chem. 107 (1958). For example, silk fibroin useful for the present invention may be that produced by a number of species, including, without limitation: *Antheraea mylitta; Antheraea pernyi; Antheraea yamamai; Galleria mellonella; Bombyx mori; Bombyx mandarins; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata;* and *Nephila madagascariensis.*

In general, silk for use in accordance with the present invention may be produced by any such organism, or may be prepared through an artificial process, for example, involving genetic engineering of cells or organisms to produce a silk protein and/or chemical synthesis. In some embodiments of the present invention, silk is produced by the silkworm, *Bombyx mori.*

As is known in the art, silks are modular in design, with large internal repeats flanked by shorter (~100 amino acid) terminal domains (N and C termini). Silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. An exemplary list of silk-producing species and corresponding silk proteins may be found in International Patent Publication Number WO 2011/130335, the entire contents of which are incorporated herein by reference.

Cocoon silk produced by the silkworm, *Bombyx mori,* is of particular interest because it offers low-cost, bulk-scale production suitable for a number of commercial applications, such as textile. Silkworm cocoon silk contains two structural proteins, the fibroin heavy chain (~350k Da) and the fibroin light chain (~25k Da), which are associated with a family of nonstructural proteins termed sericin, which glue the fibroin brings together in forming the cocoon. The heavy and light chains of fibroin are linked by a disulfide bond at the C-terminus of the two subunits (Takei, F., Kikuchi, Y., Kikuchi, A., Mizuno, S. and Shimura, K. (1987) J. Cell Biol., 105, 175-180; Tanaka, K., Mori, K. and Mizuno, S. (1993) J. Biochem. (Tokyo), 114, 1-4; Tanaka, K., Kajiyama, N., Ishikura, K., Waga, S., Kikuchi, A., Ohtomo, K., Takagi, T. and Mizuno, S. (1999) Biochim. Biophys. Acta, 1432, 92-103; Y Kikuchi, K Mori, S Suzuki, K Yamaguchi and S Mizuno, Structure of the *Bombyx mori* fibroin light-chain-encoding gene: upstream sequence elements common to the light and heavy chain, Gene 110 (1992), pp. 151-158). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" embraces silk fibroin protein, whether produced by silkworm, spider, or other insect, or otherwise generated (Lucas et al., Adv. Protein Chem., 13: 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori.* In some embodiments, spider silk fibroins are obtained, for example, from *Nephila clavipes.* In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" hydrophobic blocks are typically separated by segments of amino acids with bulky side-groups (e.g., hydrophilic spacers).

In some embodiments, core repeat sequences of the hydrophobic blocks of fibroin are represented by the following amino acid sequences and/or formulae: $(GAGAGS)_{5-15}$ (SEQ ID NO: 1); $(GX)_{5-15}$ (X=V, I, A) (SEQ ID NO: 2); GAAS (SEQ ID NO: 3); $(S_{1-2}A_{11-13})$ (SEQ ID NO: 4); $GX_{1-4}$ GGX (SEQ ID NO: 5); GGGX (X=A, S, Y, R, D V, W, R, D) (SEQ ID NO: 6); $(S1-2A1-4)_{1-2}$ (SEQ ID NO: 7); GLGGLG (SEQ ID NO: 8); GXGGXG (X=L, I, V, P) (SEQ ID NO: 9); GPX (X=L, Y, I); $(GP(GGX)_{1-4}Y)_{1-4}$ (X=Y, V, S, A) (SEQ ID NO: 10); GRGGAn (SEQ ID NO: 11); GGXn (X=A, T, V, S); $GAG(A)_{6-7}GGA$ (SEQ ID NO: 12); and GGX GX GXX (X=Q, Y, L, A, S, R) (SEQ ID NO: 13).

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks. In some embodiments of the invention, a fibroin peptide comprises at least one hydrophilic spacer sequence ("hydrophilic block") that is about 4-50 amino acids in length. Non-limiting examples of the hydrophilic spacer sequences include:

```
                            (SEQ ID NO: 14)
        TGSSGFGPYVNGGYSG;

(SEQ ID NO: 15)
        YEYAWSSE;

(SEQ ID NO: 16)
        SDFGTGS;

(SEQ ID NO: 17)
        RRAGYDR;

(SEQ ID NO: 18)
        EVIVIDDR;

(SEQ ID NO: 19)
        TTIIEDLDITIDGADGPI
        and (SEQ ID NO: 20)
        TISEELTI.
```

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

In some embodiments, a fibroin peptide suitable for the present invention contains no spacer.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and polyalanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arrangement are intimately tied with the end material properties of silk-based materials (reviewed in Omenetto and Kaplan (2010) Science 329: 528-531).

It has been observed that the beta-sheets of fibroin proteins stack to form crystals, whereas the other segments form amorphous domains. It is the interplay between the hard crystalline segments, and the strained elastic semi amorphous regions, that gives silk its extraordinary properties. Non-limiting examples of repeat sequences and spacer sequences from various silk-producing species are provided in An exemplary list of hydrophobic and hydrophilic components of fibroin sequences may be found in International Patent Publication Number WO 2011/130335, the entire contents of which are incorporated herein by reference.

The particular silk materials explicitly exemplified herein were typically prepared from material spun by silkworm, *B. Mori*. Typically, cocoons are boiled for ~30 min in an aqueous solution of 0.02M $Na_2CO_3$, then rinsed thoroughly with water to extract the glue-like sericin proteins. The extracted silk is then dissolved in LiBr (such as 9.3 M) solution at room temperature, yielding a 20% (wt.) solution. The resulting silk fibroin solution can then be further processed for a variety of applications as described elsewhere herein. Those of ordinary skill in the art understand other sources may also be appropriate.

The complete sequence of the *Bombyx mori* fibroin gene has been determined (C.-Z Zhou, F Confalonieri, N Medina, Y Zivanovic, C Esnault and T Yang et al., Fine organization of *Bombyx mori* fibroin heavy chain gene, Nucl. Acids Res. 28 (2000), pp. 2413-2419). The fibroin coding sequence presents a spectacular organization, with a highly repetitive and G-rich (~45%) core flanked by non-repetitive 5' and 3' ends. This repetitive core is composed of alternate arrays of 12 repetitive and 11 amorphous domains. The sequences of the amorphous domains are evolutionarily conserved and the repetitive domains differ from each other in length by a variety of tandem repeats of subdomains of ~208 bp.

The silkworm fibroin protein consists of layers of anti-parallel beta sheets whose primary structure mainly consists of the recurrent amino acid sequence (Gly-Ser-Gly-Ala-Gly-Ala)n (SEQ ID NO: 21). The beta-sheet configuration of fibroin is largely responsible for the tensile strength of the material due to hydrogen bonds formed in these regions. In addition to being stronger than Kevlar, fibroin is known to be highly elastic. Historically, these attributes have made it a material with applications in several areas, including textile manufacture.

Fibroin is known to arrange itself in three structures at the macromolecular level, termed silk I, silk II, and silk III, the first two being the primary structures observed in nature. The silk II structure generally refers to the beta-sheet conformation of fibroin. Silk I, which is the other main crystal structure of silk fibroin, is a hydrated structure and is considered to be a necessary intermediate for the preorganization or prealignment of silk fibroin molecules. In the nature, silk I structure is transformed into silk II structure after spinning process. For example, silk I is the natural form of fibroin, as emitted from the *Bombyx mori* silk glands. Silk II refers to the arrangement of fibroin molecules in spun silk, which has greater strength and is often used commercially in various applications. As noted above, the amino-acid sequence of the β-sheet forming crystalline region of fibroin is dominated by the hydrophobic sequence. Silk fibre formation involves shear and elongational stress acting on the fibroin solution (up to 30% wt/vol.) in the gland, causing fibroin in solution to crystallize. The process involves a lyotropic liquid crystal phase, which is transformed from a gel to a sol state during spinning—that is, a liquid crystal spinning process. Elongational flow orients the fibroin chains, and the liquid is converted into filaments.

Silk III is a newly discovered structure of fibroin (Valluzzi, Regina; Gido, Samuel P.; Muller, Wayne; Kaplan, David L. (1999). "Orientation of silk III at the air-water interface". International Journal of Biological Macromolecules 24: 237-242). Silk III is formed principally in solutions of fibroin at an interface (i.e. air-water interface, water-oil interface, etc.). Silk can assemble, and in fact can self-assemble, into crystalline structures. Silk fibroin can be fabricated into desired shapes and conformations, such as silk hydrogels (WO2005/012606; PCT/US08/65076), ultra-thin films (WO2007/016524), thick films, conformal coatings (WO2005/000483; WO2005/123114), foams (WO 2005/012606), electrospun mats (WO 2004/000915), microspheres (PCT/US2007/020789), 3D porous matrices (WO2004/062697), solid blocks (WO2003/056297), microfluidic devices (PCT/US07/83646; PCT/US07/83634), electro-optical devices (PCT/US07/83639), and fibers with diameters ranging from the nanoscale (WO2004/000915) to several centimeters (U.S. Pat. No. 6,902,932). The above mentioned applications and patents are incorporated herein by reference in their entirety. For example, silk fibroin can be processed into thin, mechanically robust films with excellent surface quality and optical transparency, which provides an ideal substrate acting as a mechanical support for high-technology materials, such as thin metal layers and contacts, semiconductor films, dielectric powders, nanoparticles, and the like.

These unique physiochemical properties of silk allows its use in a variety of applications such as those described herein. Furthermore, useful silk materials can be prepared through processes that can be carried out at room temperature and are water-based. Therefore, bio-molecules of interest can be readily incorporated into silk materials.

While a number of types of silk fibroin, such as those exemplified above, may be used to practice the claimed invention, silk fibroin produced by silkworms, such as *Bombyx mori*, is the most common and represents an earth-friendly, renewable resource. For instance, silk fibroin may be attained by extracting sericin from the cocoons of *B. mori*. Organic silkworm cocoons are also commercially available. There are many different silks, however, including spider silk (e.g., obtained from Nephila clavipes), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that may be used. As already noted, an aqueous silk fibroin solution may be prepared using techniques known in the art. Suitable processes for preparing silk fibroin solution are disclosed, for example, in U.S. patent application Ser. No. 11/247,358; WO/2005/012606; and WO/2008/127401. The silk aqueous solution can then be processed into silk matrix such as silk films, conformal coatings or layers, or 3-dimensional scaffolds, or electrospun fibers. A microfiltration step may be used herein. For example, the prepared silk fibroin solution may be processed further by centrifugation and syringe based microfiltration before further processing into silk matrix.

Purified silk can be used for technological applications by, for example, serving as a support for planar microelectronics or being used as a constituent of micro- and/or nano-scale photonic devices. Three-dimensional nanostructuring combined with the protein's material properties and versatile functionalization can open further opportunities in device applications. In the present disclosure, among other things, a silk inverse opal (SIO) that exhibits a photonic band-gap in the visible spectrum region is provided. Non-limiting embodiment is provided in the Exemplification herein.

Enhanced Heat Generation

According to the invention, it is further contemplated that devices that comprise a heating element provide a wide range of biomedical and clinical applications, such as thermal therapy. In particular, light-activated heating elements are of great interest for a number of applications, including photothermal therapy, in which electromagnetic radiation is employed to treat various medical conditions. Because silk can be doped with a variety of materials, the invention described herein can be used to design a silk-based lattice or mould (e.g., silk film) comprising a light-activated heating element when combined with plasmonic nanoparticles. Such combination can produce photothermal device of superior features, as compared to those previously described in the art.

In some embodiments, the invention provides a silk inverse opal doped with one or more types of plasmonic nanoparticles. Accordingly, aspects of the present invention provide photothermal elements that comprise a plurality of plasmonic nanoparticles that generate heat when exposed to electromagnetic radiation, and a silk fibroin matrix, within which the plurality of plasmonic nanoparticles is distributed.

In some embodiments, a silk inverse opal with gold nanoparticles (e.g., a (Au-NP) SIO) can be created. The gold nanoparticles' absorption of energy can be enhanced at the band-edge frequency, which can present patterned heating mediated by the photonic structure.

As a basis for generating heat useful for the present invention, certain nano-scale heating elements, such as plasmonic nanoparticles (e.g., GNP and gold nanoshells (GNS)), may be used. The art is familiar with plasmonic nanoparticles. Briefly, plasmonic nanoparticles resonantly absorb incident light at certain wavelengths and convert it to heat. To date, plasmonic particles have been used in photothermal therapy techniques for in vivo medical applications, such as tumor killing (Hirsch et al., 100 PNAS 13549 (2003)) and pain relief (Jaeger et al., Acta Vet. Scanda. 1 (2007)).

Thus, aspects of the present invention provide for a photothermal element comprising plasmonic nanoparticles incorporated into or distributed within a silk fibroin matrix, such that the plasmonic nanoparticles absorb at least a portion of incident radiation to generate heat when the element is exposed to the electromagnetic radiation. In some embodiments, photothermal elements described herein may be adapted to conform to a surface upon contact with the surface. In some embodiments, such surfaces include biological surfaces, such as cells and tissues.

Metal-based nanophotonics (plasmonics) is a field concerned with manipulating and focusing light on nanoscale structures that are much smaller than conventional optical components. These optically heatable nanoparticles are capable of converting at least a portion of incident radiation into heat energy when such nanoparticles are exposed to the electromagnetic radiation. Plasmonic technology has the potential to be used in applications such as nanoscale optical interconnects for high performance computer chips, highly efficient thin-film solar cells, and extremely sensitive biomolecular sensors. As described in further detail herein, the plasmonic nanoparticles of the present embodiments can be engineered to achieve peak resonance at a given wavelength of light.

According to the invention, the "plasmonic nanoparticles" useful for the present invention are plasmon resonant nanoparticles, typically metallic particles or metal-incorporated particles, that respond to electromagnetic radiation. Without wishing to be bound by a particular theory, the plasmonic nanoparticles respond to electromagnetic radiation because the conduction electrons in the metal undergo a collective resonance called a surface plasmon resonance. The magnitude, peak wavelength and spectral bandwidth of the plasmon resonance associated with a particular plasmonic nanoparticle may be dependent on the nanoparticle's size, shape, and/or material composition, as well as its local dielectric environment. See, e.g., Lu et al., *Chemical Synthesis of Novel Plasmonic Nanoparticles*, 60 Ann. Rev. Phys. Chem. 167 (2009). These factors allow for predetermined control of a plasmonic nanoparticle's thermal activity in response to a specific wavelength of electromagnetic radiation.

The plasmonic nanoparticle typically comprises at least one metal. In some embodiments, a useful plasmonic nanoparticle is typically a metal or an alloy, or is doped with at least one metal or an alloy. Such metal can be any art-recognized metal in that excitation of surface plasmon can be induced by light. In some embodiments, the metal can be a noble metal, including, but not limited to, gold, silver, ruthenium, rhodium, palladium, osmium, iridium, and platinum. Depending on the application, in some embodiments, the noble metal can possibly be mercury. In some embodiments, useful metal can be a non-noble metal, such as titanium, aluminum, nickel, fluorine, cerium, tin, bismuth, antimony, molybdenum, chromium, cobalt, zinc, tungsten, polonium, rhenium and copper. In some embodiments, the plasmonic nanoparticles can comprise oxides of noble or non-noble metals. In some embodiments, the plasmonic nanoparticles can comprise alloys of noble metals and/or non-noble metals, or nonhomogeneous mixtures of such metals. In some embodiments, the plasmonic nanoparticles can comprise silica or silk fibroin doped with rare earth emitters, such as Pr+3, Er+3, or Nd+3. See, e.g., U.S. Pat. No. 6,530,944. In one embodiment, the plasmonic nanoparticles comprise gold. In one embodiment, the plasmonic nanoparticles are gold nanoparticles.

The size of the plasmonic nanoparticles can be adapted to resonantly absorb a specific wavelength of light at a desirable absorbance level when the plasmonic nanoparticles are exposed to electromagnetic radiation. In some embodiments, the plasmonic nanoparticles can have a diameter of about 1 nm to about 1000 nm, about 5 nm to about 500 nm, about 5 nm to about 250 nm, or about 5 nm to about 100 nm, or about 5 nm to about 50 nm. In some embodiments, the plasmonic nanoparticles have a diameter of about 5 nm to about 25 nm. As used herein, the term "diameter" in reference to a population of plasmonic nanoparticles means the average diameter of the population. In some embodiments, the term "diameter" can refer to the maximum size of the plasmonic particle within the population. In other embodiments, the term "diameter" can refer to the minimum size of the plasmonic particle within the population. If the population is homogenous in size, the term "diameter" can also refer to the diameter of each individual particle.

In some embodiments, a population of plasmonic nanoparticles is a heterogeneous population, such that the population contains particles of varying diameters. In some embodiments, such variation in diameters within a population of nanoparticles is within +/−100%, 90%, 80%, 70%, 60%, 50%, 40%, 30%, 20%, 15%, 10%, 5%, 2%, or less.

It is known in the art that, at the nanoscale, bulk (e.g., solid) metals exhibit optical resonances of their surface plasmons. In colloidal form, these metals typically absorb and scatter light strongly at a characteristic wavelength (plasmon resonance) in the visible region of the spectrum. The ability to work with wavelengths in the near infrared (NIR) region of the spectrum may be for certain applications clinically meaningful because light penetrates deep within tissue (up to several centimeters) at these wavelengths. Indeed, certain geometries (spheres, rods and shells) of metal nanoparticles have optical plasmon resonances that can be tuned to the NIR region (Oldenburg et al. 1999). While gold nanospheres and nanorods are made of solid gold, nanoshells consist of a dielectric core (e.g. silica) surrounded by a thin gold shell. Nanospheres exhibit resonances around 540 nm without much tunability of this peak whereas nanoshells and nanorods have peak resonances that can be tuned throughout the NIR spectrum (Jain et al. 2006; Oldenburg et al. 1998). Nanoshells are tuned via their core-to-shell ratio while nanorods are tunable through their aspect ratio (i.e. ratio of the length to diameter). For instance, gold nanoshells comprised of an aminated colloidal silica (120 nm diameter) core with a 14-nm-thick shell of gold colloid adsorbed onto it as sequential nucleating sites result in an absorption peak between 780 and 800 nm.

Thus, unique properties of silk-based materials allow a broader range of utilities for plasmonic nanoparticles, which provide increased tonability (e.g., control) and precision. Unlike conventional devices that incorporate plasmonic nanoparticles, silk-based devices provide biocompatibility, biodegradability and conformability.

In the context of the present invention, the plasmonic nanoparticles can be distributed within or on the silk fibroin matrix in great variation to optimize photothermal activity for a particular use. In some embodiments, the plasmonic nanoparticles can be evenly distributed within or on the surface of the silk fibroin matrix. In some embodiments, the plasmonic nanoparticles can be distributed in a gradient within or on the silk fibroin matrix, e.g., more plasmonic nanoparticles can be selectively distributed within or on one portion of the silk fibroin matrix. In some embodiments, the plasmonic nanoparticles can be distributed in a pattern such as an optical pattern, a micropattern, or a nanopattern. See, e.g., Dong et al., *Biogenic synthesis of hierarchical hybrid nanocomposites and patterning of silver nanoparticles*, 110 Mats. Chem. Phys. 160 (2008). The pattern can be achieved by any known technique, such as nanoprinting or etching, and allows for corresponding patterned photothermal or photothermal-electric generation. Such gradients or patterns provide for control of photothermal or thermo-electric energy in a predetermined fashion. In other words, dosages and locations of energy delivery can be designed and integrated into the silk fibroin matrix by selective distributing or patterning of the plasmonic nanoparticles.

As mentioned, the invention described herein is useful for implantable medical devices (IMDs) that monitor and treat physiological conditions within a human body. IMDs broadly have attracted tremendous interest from biologists, physicians, and engineers around the globe. IMDs are utilized to manage a broad range of ailments, including, but not limited to, diabetes (Jaremko & Rorstad, 21 Diabetes Care 444 (1998)), arrhythmia (Hsia et al., 87 Annals Thoracic Surg. 124 (2009)), and Parkinson's disease (Singh et al., 81 Adv. Treat. Parkinson's Dis. 29 (2007)). The need for miniature, low power, wireless IMDs has surged, and progress has been made in the past two decades encompassing micro- and nano-technologies. See Staples et al., 23 Pharm. Res. 847 (2006); Lu & Chen, 56 Adv. Drug Deliv. Rev. 1621 (2004); Hilt & Peppas, 306 Intl. J. Pharm. 15 (2005). Despite these advances, improvements are still needed in the long-term stability and functionality of IMDs, especially for active devices that need power for their appropriate operation. The necessary improvements, addressed herein, involve advancing the biocompatibility of the construction and encapsulation materials for those devices, as well as power source solutions. In some embodiments, these IMDs can incorporate the aspects of the present invention based on the instant specification. Exemplary IMDs include, but are not limited to, pacemakers (Narazaki & Yamashita, 29 Inflammation & Regeneration 123 (2009)); cardiac defibrillators (McAlister et al., 152 Evidence Report/Tech. Assessment 1 (2007)); nerve stimulators (Mobbs et al., 14 J. Clin. Neurosci. 216 (2007)); and drug delivery systems (Elman et al., 11 Biomedical Microdevices 1387 (2009)).

For implantation utility, absorption, as exemplified in the Examples, peaks at wavelengths close to 532 nm by tissue chromophores, such as hemoglobin and melanin, may create limitations on the penetration depth of the laser when coupled with these tissue chromophores. In order to reach an implant deeper than approximately 0.5 mm, the power would need to be increased to unsafe levels, which may cause tissue damage or burns. Hamlin & Demidova, 6140 Proc. SPIE 1 (2006). In addition, water can act as a chromophore at wavelengths longer than 1150 nm, thus leaving an available "optical window" between about 600 nm and about 1150 nm with low levels of absorption. Id. Accordingly, in some embodiments, the plasmonic nanoparticles of the invention can be tuned to be resonant at any wavelength between about 600 nm and about 1150 nm. In some embodiments, the plasmonic nanoparticles can be tuned to be resonant at longer wavelengths, such as about 670 nm, about 830 nm, or about 1064 nm. Stolik et al., 57 J. Photochem. Photobio. B: Bio. 90 (2000). This can be accomplished, for example, by changing the diameter of the plasmonic nanoparticles or using nanoshells for longer penetration depths. Prodan et al., 3 Nano Lett. 1411 (2003). At these wavelengths, the absorption rate of body tissues will be relatively low, so that safe power levels will be possible even for deeply implanted devices.

In some embodiments, plasmonic nanoparticles can further comprise an additional material. The additional material can be selected based upon the choice of the metal used in the plasmonic nanoparticles, the desirable wavelength of the resonant peak, the absorbance magnitude, the spectrum bandwidth, and/or other desirable properties of the plasmonic particles, e.g., magnetic properties. In some embodiments, the additional material can be silk fibroin. Silk fibroin nanoparticles can be produced as taught, for example, in Zhang et al., *Formation of silk fibroin nanoparticles in water-miscible organic solvent and their characterization*, 9 J. Nanoparticle Res. 885 (2007); Gupta et al., 4 Intl. J. Nanomed. 117 (2009); Kharlampieva et al., *Silk-based Mechanically-robust LbL Nano-composites with Tailored Optical Properties*, 101 PMSE Preprints 1059 (2009).

In some embodiments, photothermal elements described herein can include at least one active agent, e.g., within the silk fibroin matrix and/or in the plasmonic nanoparticles. Examples of the active agent include, without limitations, organic materials such as horseradish peroxidase, phenolsulfonphthalein, oligonucleotides, nucleic acids, aptamers, antibodies or antibody-like molecules (e.g., fragments of antibodies, single-chain antibodies (scFv), single domain antibodies, chimeric antibodies, and diabodies), enzymes (for example, peroxidase, lipase, amylose, organophosphate dehydrogenase, ligases, restriction endonucleases, ribonucleases, RNA or DNA polymerases, glucose oxidase, and lactase), cells (including red blood cells and stem cells), viruses, other proteins, or peptides, peptidomimetics, small molecules (e.g., drugs, dyes, amino acids, vitamins, antioxidants), biosimilars, biologics, lipids, carbohydrates, chromophores, light emitting organic compounds (such as luciferin, carotenes) and light emitting inorganic compounds (e.g., chemical dyes and/or contrast enhancing agents such as indocyanine green), antibiotics, antifungals, antivirals, light-harvesting compounds such as chlorophyll, bacteriorhodopsin, proteorhodopsin, and porphyrins and related electronically active compounds, or pro-drugs, analogs, and any combinations of any of the foregoing. See, e.g., WO 2011/006133, Bioengineered Silk Protein-Based Nucleic Acid Delivery Systems; WO 2010/141133, Silk Fibroin Systems for Antibiotic Delivery; WO 2009/140588, Silk Polymer-Based Adenosine Release: Therapeutic Potential for Epilepsy; WO 2008/118133, Silk Microspheres for Encapsulation & Controlled Release; WO 2005/123114, Silk-Based Drug Delivery System.

In some embodiments where the photothermal element is used for treating tissues, the silk fibroin can include at least one factor that can facilitate treatment of tissues, e.g., wound healing. Such factors include, without limitations, albumin, fibrinogen, collagen, elastin, fibronectin, laminin, chitosan, fibroblast growth factor, vascular endothelial cell growth factor, platelet-derived growth factor, epidermal growth factor, insulin-like growth factor, and any combinations thereof. In some embodiments, the active agents or factors described herein can be further encapsulated into a different silk fibroin carrier, e.g., microparticles, nanoparticles, films or porous sponges, that can regulate the release of the active agent or the factor, before distributed in the silk fibroin matrix of the photothermal element. See e.g., WO 2008/118133; WO 2009/140588; WO 2011/008842, Electrospun Silk Material Systems for Wound Healing. In some embodiments where a specific tissue or organism is targeted, at least a portion of the silk fibroin matrix, the plasmonic nanoparticles, and/or the silk fibroin carriers can be further bound to one or more targeting moieties. Exemplary targeting moieties include, but are not limited to, an antibody, fragments of antibodies, ligands for specific receptors or proteins that can bind specifically to the organism, cell, or tissue. See, e.g., U.S. Pat. Nos. 6,685,730; 6,530,944.

Accordingly, the present invention provides for methods for the localized delivery of heat and the localized imaging of biological materials, e.g., cells and/or tissues. The delivery can be in vitro or in vivo, and is useful for the localized treatment of a disease or disorder, e.g., cancer, inflammation, or other disorders involving over-proliferation of tissue.

The method involves localized induction of heat to a cell or tissue by delivering to said cell or tissue a conformal silk fibroin matrix comprising plasmonic nanoparticles and exposing the plasmonic nanoparticles to an excitation source under conditions wherein they emit heat. One embodiment of the invention includes a method for inducing localized heat to a cell or tissue. The method includes delivering the photothermal element described herein to cells or tissue; and exposing said photothermal element to electromagnetic radiation, such as ultraviolet, visible, infrared, or any combination thereof, wherein the plasmonic nanoparticles emit heat upon exposure to said electromagnetic radiation. The method can also be useful for diagnostic imaging alone, or in combination with photothermal therapy. See Hirsch et al., 100 PNAS 13549 (2003).

Additionally, in some embodiments of the present invention, the photothermal element provides for a system that can modulate in vivo delivery of an agent. The system includes a plurality of plasmonic nanoparticles, capable of converting incident radiation into heat energy when the nanoparticles are irradiated with electromagnetic radiation, contained in a silk fibroin matrix that can further comprise at least one active agent distributed therein. By way of example, when the temperature of the silk fibroin matrix or portion thereof is at a first temperature (e.g., 37° C.), the active agent is retained within the silk fibroin matrix. When the silk fibroin matrix or a portion thereof is raised to a second, higher temperature (e.g., ~40° C.-45° C.), i.e., heat generated by plasmonic particles exposed to electromagnetic radiation, at least a portion of the active agent can be released from the silk fibroin matrix into the body. Optionally, embodiments of the invention can include a biosensor system, e.g., for providing information about in vivo status to assist in making treatment decisions. An advantage of the system is the ability to locally change the temperature of a thermally-responsive IMD by exposure to light targeted for absorption and conversion to heat by plasmonic nanoparticles (including, e.g., metal nanoshells). This allows implantation of a drug delivery device with multiple dosages, and provides for an external control over the dosage profiles by regulating exposure of the drug delivery device to an appropriate light source.

Another aspect of the invention relates to a method of photothermally modulating in vivo delivery of an active agent. The method includes implanting into the body of a subject in need of treatment, a composition or a device containing one or more plasmonic nanoparticles and at least one active agent in a silk fibroin matrix. The active agent can be substantially retained by the silk fibroin matrix when the temperature of the composition is at about normal body temperature of the subject. At least a portion of the active agent can be substantially released from the silk fibroin matrix into the body of the subject when the temperature of the composition, or a portion thereof, is raised. The method includes applying electromagnetic radiation, such as near-infrared radiation, to the implanted composition or device from outside the body. The electromagnetic radiation can be applied through an optical grid. The amount and duration of electromagnetic radiation can be applied until it is sufficient to raise the temperature of the plasmonic nanoparticles such that the silk fibroin matrix, or a portion thereof, can cause release of the agent to commence. Alternatively, application of the electromagnetic radiation can be continued until a desired amount of the active agent has been released from the implant into the body. After the desired amount of the agent has been delivered, the composition can be allowed to return to normal body temperature, whereupon drug delivery is reduced or ceased, as desired. In some embodiments, the application of electromagnetic radiation can be repeated at a later time, if multiple dosing is desired. In some embodiments, the treatment method can further comprise applying ultrasound, magnetic fields, electric fields, or any combinations thereof, to the implanted composition or device from outside the body. The silk fibroin matrix is biocompatible and biodegradable, and does not require subsequent removal. The implantation can be subcutaneous or parenteral.

Another embodiment of the invention provides for a method of enhancing wound healing, such as tissue welding. For example, laser tissue welding refers to techniques by which tissues can be joined in response to exposure to light and the subsequent generation of heat. The goal of these techniques is the rapid joining of tissues with high tensile strength across the union, a tissue union throughout the depth of the targeted tissue, a minimum of scar tissue formation, and minimal damage to surrounding tissue. These techniques can also be beneficial in a number of minimally invasive surgical techniques. Laser tissue repair has application in many surgical disciplines for procedures such as closure of skin wounds, vascular anastomosis, ocular repair, nerve repair, cartilage repair, and liver repair. Currently, laser tissue repair is accomplished either through welding, apposing two tissue surfaces and then exposing to laser radiation to heat the tissues sufficiently to join them, or through soldering, wherein an exogenous material such as a protein or synthetic polymer is placed between two tissue surfaces to enhance joining of the tissues upon exposure to laser radiation. Temperatures greater than 50° C. can induce tissue union, which can be likely induced by the denaturation of proteins and the subsequent entanglement of adjacent protein chains. See, e.g., U.S. Pat. No. 6,685,730. In accordance with methods of the invention, the conformal photothermal element as described herein can be contacted with the tissue, and irradiated to transfer heat to the target tissue. See also WO 2010/065957, Vascularized Living Skin Constructs & Methods of Use Thereof, WO 2011, Electrospun Silk Material Systems for Wound Healing.

Accordingly, plasmonic nanoparticle-doped silk fibroin matrix may be used to achieve heat-based bonding of a wound. Thus, the invention includes silk-based "stitchless sutures" which can be controlled by illumination of a target wound site so as to generate lightactivated heat which aids in bonding or welding of a wound or tissue. For example, useful embodiments of the invention for the contemplated utility include a composition comprising silk-based "inverse mould" having structural colors, comprising plasmonic nanoparticles for controllable heat generation suitable for in vivo applications.

Accordingly, plasmonic nanoparticle-doped silk fibroin matrix may be used to achieve heat-based bonding of a wound. Thus, the invention includes silk-based "stitchless sutures" which can be controlled by illumination of a target wound site so as to generate lightactivated heat which aids in bonding or welding of a wound or tissue. For example, useful embodiments of the invention for the contemplated utility include a composition comprising photothermal plasmonic nanoparticles dispersed within a silk-based material, such as a gel and film, so as to form plasmonic nanoparticle-dosed silk matrix. Such a plasmonic nanoparticledosed silk matrix can be applied to a site of would or tissue to be repaired, e.g., along the edges of an open wound or tissues to be bonded. The site is then illuminated with a suitable light source to induce heat generation, with little or no adverse effects to surrounding tissues.

Improved Sensing of Refractive Index

Label free photonic sensors are of great interest because of their ability to analyze biomolecules with high sensitivity and in the absence of marker molecules. The most conventional sensors are based on surface plasmon polariton phenomena, whereby a prism is used to couple light to excite a surface plasmonic resonance (SPR) mode on a flat metal film. The sensor, however, is composed of a bulky optical set-up, so it is difficult to integrate this system into small devices for rapid measurements of mass-limited samples. Recent work shows that micro/nano photonic structures, such as photonic crystals (PhCs) and SPR-based metal nanostructures, can be used as label free sensors via compact and simple optical measurements. An additional degree of utility is provided by using biocompatible materials as the material constituents to extend sensor applications to in vivo and in vitro experimentation. Silk, the natural protein extracted from the *Bombyx mori* caterpillar, is an attractive material for applications in biophotonics due to its biocompatibility and unique mechanical and optical characteristics. Enzymes and drugs can be incorporated into the silk matrix under an all aqueous and mild processing workflow. Additionally, a series of studies on micro- and nanofabrication have introduced the use of silk films a platform for bioapplications.

PhCs and SPR structures have independently contributed to demonstrate micro/nano photonic devices with marvelous capability and novel functionality. Recently, hybrid structures integrating PhC and SPR structures have been investigated with the expectation of novel characteristics arising from the interplay between these phenomena.

In optics, the refractive index (or index of refraction) of a substance (optical medium) is a dimensionless number that describes how light, or any other radiation, propagates through that medium. The refractive index, which may vary with wavelength, may generally be defined as the factor by which the wavelength and the velocity of the radiation are reduced with respect to their vacuum values. Most transparent media have refractive indices between 1 and 2, at least for visible light.

Figure 18:
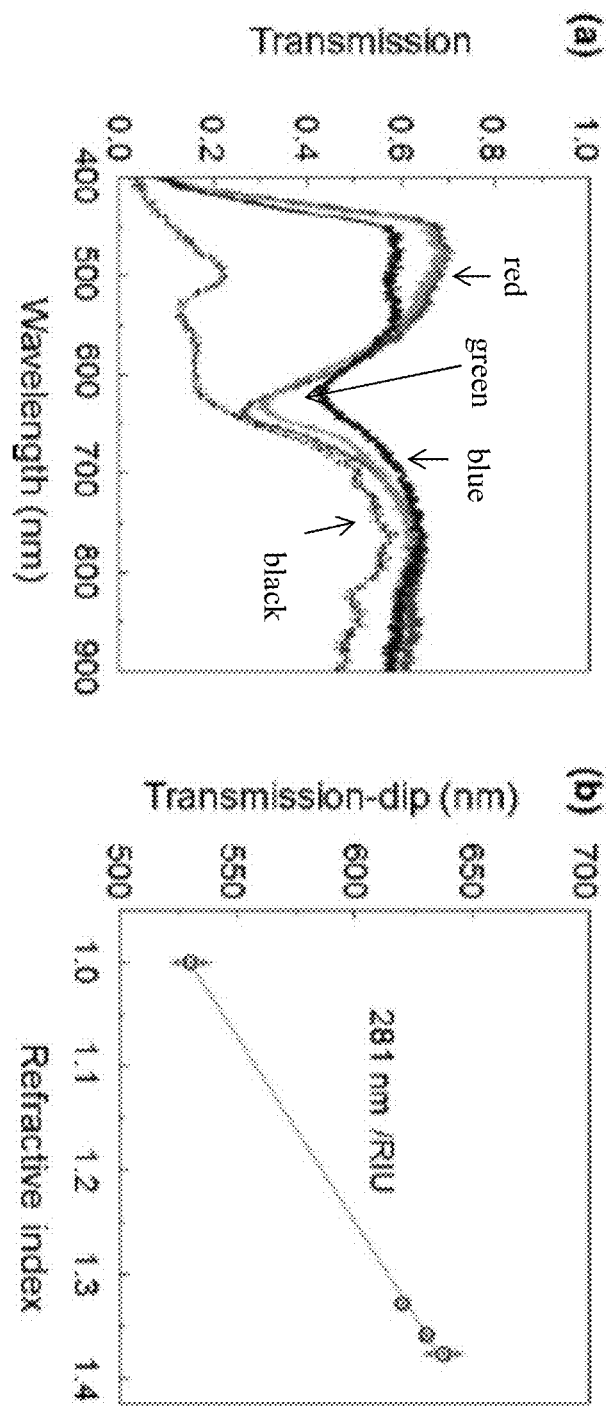
FIG. 18(a) depicts transmission spectra in different environment medium: air (black), methanol (blue), acetone (green), IPA (red).
FIG. 18(b) depicts a plot of wavelength of transmission-dip as a function of refractive index.

The silk-HPPC RI sensor may be sensitive (and may show substantially linear response between the transmission and the refractive index) to detect and/or measure a wide range of refractive indices. In some embodiments, silk-HPPC RI sensor is capable of responding to a wide range of RI, which allows detection and/or identification of various media (e.g., materials) having different RI values. Silk-HPPC RI described herein have a wider linear range of sensing ability as compared to a number of sensors available in the art, including other RI sensor technologies, which are generally disfavored in most applications due to their limited range and/or relatively low sensitivity. For example, embodiments of the Silk-HPPC RI sensor may be able to detect and/or identify detection a range of refractive indices from 1.0 to 2.0, from 1.0 to 1.5, from 1.0 to 1.6, from 1.0 to 1.7, from 1.0 to 1.8, from 1.0 to 1.9, from 1.2 to 1.7, from 1.2 to 1.8, from 1.2 to 1.9, from 1.2 to 2.0, from 1.3 to 1.9, from 1.3 to 1.8, from 1.3 to 1.7, from 1.3 to 1.6, from 1.5 to 1.9, from 1.5 to 1.8, or from 1.5 to 2.0. The Silk-HPPC RI sensor may have substantially linear relationship between transmission measured as a function of refractive index (as shown in the example of FIG. 18) within each of these ranges.

Enhancement of Fluorescent Measurement

In some embodiments, a light-responsive entity is capable of absorbing a photon, entering an excited state, and/or emitting a photon. In some embodiments, a light-responsive entity contains electrons which can absorb a photon and briefly enter an excited state before either dispersing the energy non-radiatively or emitting it as a photon, but with a lower energy, i.e., at a longer wavelength (wavelength and energy are inversely proportional). Such light-responsive entities useful for the present invention may include entities comprising a fluorophores(s), such as fluorescent compounds and fluorescent particles (e.g., fluorescent dyes and quantum dots).

Fluorescence is used in the life sciences generally as a non-destructive way of tracking or analysing biological molecules by means of fluorescence. Some proteins or small molecules in cells are naturally fluorescent, which is called intrinsic fluorescence or autofluorescence (such as NADH, tryptophan or endogenous Chlorophyll, Phycoerythrin or green fluorescent protein). Alternatively, specific or general proteins, nucleic acids, lipids or small molecules can be "labeled" with an extrinsic fluorophore, a fluorescent dye which can be a small molecule, protein or quantum dot. Several techniques exist to exploit additional properties of fluorophores, such as fluorescence resonance energy transfer, where the energy is passed non-radiatively to a particular neighbouring dye, allowing proximity or protein activation to be detected; another is the change in proprieties, such as intensity, of certain dyes depending on their environment allowing their use in structural studies. Given wide use of fluorophores in a variety of applications, the present invention is broadly applicable where augmentation of fluorescent signal is desired. While the invention described herein is not limited by specific types of light-responsive entities, examples of fluorophores are provided below.

Fluorescent dyes include, but are not limited to:
Acridine orange; Acridine yellow; Alexa Fluor; 7-Aminoactinomycin D; 8-Anilinonaphthalene-1-sulfonic acid; ATTO dyes; Auramine O; Auramine-rhodamine stain; Benzanthrone; Bimane; 9,10-Bis(phenylethynyl)anthracene; 5,12-Bis(phenylethynyl)naphthacene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl)anthracene; 2-Chloro-9,10-diphenylanthracene; Coumarin; Cresyl violet; Cyanine; DAPI; Dark quencher; Dichlorofluorescein; DiI; DiOC6; DyLight Fluor; Eosin; Eosin B; Eosin Y; Erythrosine; Ethidium bromide; Fluo-3; Fluo-4; FluoProbes; Fluorescein; Fluorescein amidite; Fluorescein isothiocyanate; Fluoro-Jade stain; Fura-2; Fura-2-acetoxymethyl ester; Green fluorescent protein; Heptamethine dyes; Hoechst stain; Indian yellow; Indo-1; Lucifer yellow; Luciferin; MCherry; Merbromin; Merocyanine; Nile blue; Nile red; Optical brightener; Perylene; Phloxine; Phycobilin; Phycoerythrin; Phycoerythrobilin; Propidium iodide; Pyranine; Rhodamine; Rhodamine 123; Rhodamine 6G; Rhodamine B; RiboGreen; RoGFP; Rubrene; (E)-Stilbene; (Z)-Stilbene; Sulforhodamine 101; Sulforhodamine B; SYBR Green I; Synapto-pHluorin; Tetraphenyl butadiene; Tetrasodium; tris (bathophenanthroline disulfonate)ruthenium(II); Texas Red; Titan yellow; TSQ; Umbelliferone; Yellow fluorescent protein; and any combinations thereof.

Reactive fluorescent dyes are widely used to modify amino acids, peptides, proteins (in particular, antibodies), oligonucleotides, nucleic acids, carbohydrates and other biological molecules. Among the reactive dyes, amine-reactive dyes are most often used to prepare various bioconjugates for immunochemistry, histochemistry, fluorescence in situ hybridization (FISH), cell tracing, receptor binding and other biological applications since amino groups are either abundant or easily introduced into biomolecules. In general, thiol-reactive reagents are frequently used to develop probes for investigating some particular protein structures and functions. Additionally, some amine-containing fluorescent reagents are also used to modify biomolecules, in particular, to label glycoproteins. Compared to amino and thiol groups, hydroxy and carboxy groups are less frequently used to label biopolymers. Non-limiting examples of useful reactive fluorescent dyes may be selected from the following:

1-Aminomethylpyrene, hydrochloride; 1-Pyrenebutanoic acid; 1-Pyrenebutanoic acid, hydrazide; 1-Pyrenebutanoic acid, succinimidyl ester; 1-Pyrenesulfonyl chloride; 2,6-TNS 2-(p-Toluidinyl)naphthalene-6-sulfonic acid, sodium salt; 2-Aminoacridone; 5(6)-CR110 [5- (and -6)-Carboxyrhodamine 110, hydrochloride]; 5(6)-CR110, SE 5- (and -6)-Carboxyrhodamine 110, succinimidyl ester; 5(6)-CR110, NHS ester; 5(6)-CR6G [5- (and -6)-Carboxyrhodamine 6G, hydrochloride]; 5(6)-CR6G, SE [5- (and -6)-Carboxyrhodamine 6G, succinimidyl ester; 5(6)-CR6G, NHS ester]; 5(6)-FAM [5- (and -6)-Carboxyfluorescein]; 5(6)-FAM [5- (and -6)-Carboxyfluorescein]; 5(6)-FAM [5- (and -6)-Carboxyfluorescein]; 5(6)-FAM [5- (and -6)-Carboxyfluorescein]; 5(6)-FAM, SE 5- (and -6)-Carboxyfluorescein, succinimidyl ester; 5(6)-FAM, NHS ester; 5(6)-FAM, SE [5- (and -6)-Carboxyfluorescein, succinimidyl ester; 5(6)-FAM, NHS ester]; 5(6)-FAM, SE [5- (and -6)-Carboxyfluorescein, succinimidyl ester; 5(6)-FAM, NHS ester]; 5(6)-ROX [5- (and -6)-Carboxy-X-rhodamine]; 5(6)-ROX, SE [5- (and -6)-Carboxy-X-rhodamine, succinimidyl ester]; 5(6)-ROX, NHS ester; 5(6)-TAMRA cadaverine [Tetramethylrhodamine 5- (and -6)-carboxamide cadaverine]; 5(6)-TAMRA, SE [5- (and -6)-Carboxytetramethylrhodamine, succinimidyl ester; 5(6)-TAMRA, NHS ester]; 5(6)-TAMRA, SE [5- (and -6)-Carboxytetramethylrhodamine, succinimidyl ester; 5(6)-TAMRA, NHS ester]; 5(6)-TAMRA, SE [5- (and -6)-Carboxytetramethylrhodamine, succinimidyl ester; 5(6)-TAMRA, NHS ester]; 5(6)-TAMRA, Special Formulation [5- (and -6)-Carboxytetramethylrhodamine]; 5(6)-TAMRA, Special Formulation [5- (and -6)-Carboxytetramethylrhodamine]; 5(6)-TAMRA, Special Formulation [5- (and -6)-Carboxytetramethylrhodamine]; 5(6)-TAMRA, Special Formulation [5- (and -6)-Carboxytetramethylrhodamine]; 5(6)-TAMRA, Special Formulation [5- (and -6)-Carboxytetramethylrhodamine]; 5(6)-TAMRA-X, SE [6-(Tetramethylrhodamine-5- (and -6)-carboxamido) hexanoic acid, succinimidyl ester; 5(6)-TAMRA-X, NHS ester]; 5(6)-TRITC [Tetramethylrhodamine-5- (and -6)-isothiocyanate]; 5- (and -6)-Carboxy-2',7'-dichlorofluorescein; 5- (and -6)-Carboxy-2',7'-dichlorofluorescein, succinimidyl ester; 5-CR110[5-Carboxyrhodamine 110, hydrochloride]; 5-CR110, SE [5-Carboxyrhodamine 110, succinimidyl ester; 5-CR110, NHS ester]; 5-CR6G [5-Carboxyrhodamine 6G, hydrochloride]; 5-CR6G, SE [5-Carboxyrhodamine 6G, succinimidyl ester; 5-CR6G, NHS ester]; 5-DTAF [5-(4,6-Dichlorotriazinyl)aminofluorescein]; 5-FAM [5-Carboxyfluorescein]; 5-FAM [5-Carboxyfluorescein]; 5-FAM [5-Carboxyfluorescein]; 5-FAM [5-Carboxyfluorescein]; 5-FAM cadaverine [Fluorescein-5-carboxamide cadaverine]; 5-FAM LYS [Fluorescein-5-carboxamide lysine]; 5-FAM, SE [5-Carboxyfluorescein, succinimidyl ester; 5-FAM, NHS ester]; 5-FAM-X, SE [6-(Fluorescein-5-carboxamido)hexanoic acid, succinimidyl ester; 5-FAM-X, NHS ester]; 5-FITC [5-FITC; fluorescein-5-isothiocyanate]; 5-FITC cadaverine [5-((5-Aminopentyl)thioureidyl)fluorescein]; 5-FTSC [Fluorescein-5-thiosemicarbazide]; 5-IAF [5-Iodoacetamidofluorescein]; 5-ROX [5-Carboxy-X-rhodamine]; 5-ROX, SE [5-Carboxy-X-rhodamine, succinimidyl ester; 5-ROX, NHS ester]; 5-TAMRA cadaverine [Tetramethylrhodamine-5-carboxamide cadaverine]; 5-TAMRA Lysine [Tetramethylrhodamine-5-carboxamide lysine]; 5-TAMRA, SE [5-Carboxytetramethylrhodamine, succinimidyl ester; 5-TAMRA, NHS ester]; 5-TAMRA [5-Carboxytetramethylrhodamine]; 5-TMRIA [5-TAMRA; Tetramethylrhodamine-5-iodoacetamide]; 5-TRITC, G isomer [Tetramethylrhodamine-5-isothiocyanate]; 6-CR110 [6-Carboxyrhodamine 110, hydrochloride]; 6-CR110, SE [6-Carboxyrhodamine 110, succinimidyl ester; 6-CR110, NHS ester]; 6-CR6G [6-Carboxyrhodamine 6G, hydrochloride]; 6-CR6G, SE [6-Carboxyrhodamine 6G, succinimidyl ester; 6-CR6G, NHS ester]; 6-DTAF [6-(4,6-Dichlorotriazinyl)aminofluorescein]; 6-FAM [6-Carboxyfluorescein]; 6-FAM, SE [6-Carboxyfluorescein, succinimidyl ester; 6-FAM, NHS ester]; 6-FITC [6-FITC, fluorescein-6-isothiocyanate]; 6-HEX, acid [6-carboxy-2',4,4',5',7,7'-hexachlorofluorescein]; 6-HEX, SE [6-carboxy-2',4,4',5',7,7'-hexachlorofluorescein, succinimidyl ester; 6-HEX, NHS ester]; 6-IAF [6-Iodoacetamidofluorescein]; 6-JOE, SE [6-Carboxy-4',5'-dichloro-2',7'-dimethoxyfluorescein, succinimidyl ester; 6-JOE, NHS ester]; 6-ROX [6-Carboxy-X-rhodamine]; 6-ROX, SE [6-Carboxy-X-rhodamine, succinimidyl ester; 6-ROX, NHS ester]; 6-TAMRA cadaverine [Tetramethylrhodamine 6-carboxamide cadaverine]; 6-TAMRA, SE [6-Carboxytetramethylrhodamine, succinimidyl ester; 6-TAMRA, NHS ester]; 6-TAMRA [6-Carboxytetramethylrhodamine]; 6-TET, acid [6-Carboxy-2]; 6-TET, SE [6-Carboxy-2; 6-TET, NHS ester]; 6-TRITC, R isomer [Tetramethylrhodamine-6-isothiocyanate]; 7-Hydroxy-4-methylcoumarin-3-acetic acid; 7-Hydroxy-4-methylcoumarin-3-acetic acid, succinimidyl ester; 7-Hydroxycoumarin-3-carboxylic acid; 7-Hydroxycoumarin-3-carboxylic acid, succinimidyl ester; 7-Methoxycoumarin-3-carbonyl azide; 7-Methoxycoumarin-3-carboxylic acid; 7-Methoxycoumarin-3-carboxylic acid, succinimidyl ester; ABD-F [4-Fluoro-7-aminosulfonylbenzofurazan]; AFC [7-Amino-4-(trifluoromethyl)coumarin]; AMC [7-Amino-4-methylcoumarin]; AMCA-X [6-((7-Amino-4-methylcoumarin-3-acetyl)amino)hexanoic acid]; AMCA-X, SE [6-((7-Amino-4-methylcoumarin-3-acetyl)amino) hexanoic acid, succinimidyl ester]; AMCA-X, NHS ester; AMF [4'-(Aminomethyl)fluorescein, hydrochloride]; ANDS [7-Aminonaphthalene-1,3-disulfonic acid, potassium salt]; Badan [6-Bromoacetyl-2-dimethylaminonaphthalene]; bBBr [Dibromobimane]; DACIA [N-(7-Dimethylamino-4-methylcoumarin-3-yl)iodoacetamide]; DACITC [7-Dimethylamino-4-methylcoumarin-3-isothiocyanate]; DACM [N-(7-Dimethylamino-4-methylcoumarin-3-yl)maleimide]; Dansyl cadaverine [5-Dimethylaminonaphthalene-1-(N-(5-aminopentyl))sulfonamide]; Dansyl chloride [5-Dimethylaminonaphthalene-1-sulfonyl chloride]; Dansyl-X, acid; Dansyl-X, SE; Dansyl-X, NHS ester; DCIA [7-Diethylamino-3-((4'-(iodoacetyl)amino)phenyl)-4-methylcoumarin]; DEAC, acid [7-Diethylaminocoumarin-3-carboxylic acid]; DEAC, SE [7-Diethylaminocoumarin-3-carboxylic acid, succinimidyl ester]; DMACA [7-Dimethylaminocoumarin-4-acetic acid]; DMACA, SE [7-Dimethylaminocoumarin-4-acetic acid, succinimidyl ester; DMACA, NHS ester]; EDANS; 5-[(2-aminoethyl)amino]naphthalene-1-sulfonic acid; EDANS C2 maleimide; EDANS Iodoacetamide [5-((((2-Iodoacetyl)amino)ethyl) amino)naphthalene-1-sulfonic acid]; EDANS, acid [5-((2-Aminoethyl)amino)naphthalene-1-sulfonic acid]; EDANS, sodium salt [5-((2-Aminoethyl)amino)naphthalene-1-sulfonic acid, sodium salt]; Fluorescamine; Fluorescein-5-maleimide; HiLyte Fluor™ 405 acid; HiLyte Fluor™ 405 acid, SE; HiLyte Fluor™ 405 acid, NHS ester; HiLyte Fluor™ 405 acid, SE; HiLyte Fluor™ 405 acid, NHS ester; HiLyte Fluor™ 405 amine TFA salt; HiLyte Fluor™ 405 C2 maleimide; HiLyte Fluor™ 405 hydrazide; HiLyte Fluor™

488 acid; HiLyte Fluor™ 488 acid, SE; HiLyte Fluor™ 488 acid, NHS ester; HiLyte Fluor™ 488 acid, SE; HiLyte Fluor™ 488 acid, NHS ester; HiLyte Fluor™ 488 amine, TFA Salt; HiLyte Fluor™ 488 C2 maleimide; HiLyte Fluor™ 488 hydrazide; HiLyte Fluor™ 555 acid; HiLyte Fluor™ 555 acid, SE; HiLyte Fluor™ 555 acid, NHS ester; HiLyte Fluor™ 555 amine; HiLyte Fluor™ 555 C2 maleimide; HiLyte Fluor™ 555 hydrazide; HiLyte Fluor™ 594 acid; HiLyte Fluor™ 594 acid, SE; HiLyte Fluor™ 594 acid, NHS ester; HiLyte Fluor™ 594 acid, SE; HiLyte Fluor™ 594 acid, NHS ester; HiLyte Fluor™ 594 amine TFA salt; HiLyte Fluor™ 594 C2 maleimide; HiLyte Fluor™ 594 hydrazide-TFA Salt; HiLyte Fluor™ 647 acid; HiLyte Fluor™ 647 acid, SE; HiLyte Fluor™ 647 acid, NHS ester; HiLyte Fluor™ 647 amine; HiLyte Fluor™ 647 C2 maleimide; HiLyte Fluor™ 647 hydrazide; HiLyte Fluor™ 680 acid; HiLyte Fluor™ 680 acid, SE; HiLyte Fluor™ 680 acid, NHS ester; HiLyte Fluor™ 680 amine; HiLyte Fluor™ 680 C2 maleimide; HiLyte Fluor™ 680 hydrazide; HiLyte Fluor™ 750 acid; HiLyte Fluor™ 750 acid, SE; HiLyte Fluor™ 750 acid, NHS ester; HiLyte Fluor™750 amine; HiLyte Fluor™ 750 Bis-NHS ester, isomer II TEA salt; HiLyte Fluor™ 750 C2 maleimide; HiLyte Fluor™ 750 hydrazide; HiLytePlus™ 555 acid; HiLytePlus™ 555 succinimidyl ester; HiLytePlus™ 647 acid; HiLytePlus™ 647 amine; HiLytePlus™ 647 succinimidyl ester; LRB-EDA [Lissamine™ rhodamine B ethylenediamine-TFA salt]; LRB-SC [Lissamine™ rhodamine B sulfonyl chloride]; LRB-SC [Lissamine™ rhodamine B sulfonyl chloride]; mBBr [Monobromobimane]; Mca; 7-Methoxycoumarin-4-acetic acid; N-(1-Pyrene)maleimide; NBD-Cl [4-Chloro-7-nitrobenzofurazan]; NBD-F [4-Fluoro-7-nitrobenzofurazan]; NBD-X [6-(N-(7-Nitrobenz-2-oxa-1,3-diazol-4-yl)amino)hexanoic acid]; NBD-X, SE; Succinimidyl 6-(N-(7-nitrobenz-2-oxa-1,3-diazol-4-yl)amino)hexanoate; NBD-X, NHS ester; PMIA; N-(1-Pyrenemethyl)iodoacetamide; SBF-Cl [4-Chloro-7-sulfobenzofurazan, ammonium salt]; SBF-F [4-Fluoro-7-sulfobenzofurazan, ammonium salt]; Sulforhodamine 101 C2 maleimide; Sulforhodamine 101 cadaverine; Sulforhodamine 101 lysine; Sulforhodamine 101 sulfonyl chloride; Tetramethylrhodamine-5 C2 maleimide; Tetramethylrhodamine-5- (and -6) C2 maleimide; Tetramethylrhodamine-5- (and -6) C2 maleimide; Tetramethylrhodamine-5- (and -6)-maleimide; Tetramethylrhodamine-5-maleimide; Tetramethylrhodamine-6 C2 maleimide; Tetramethylrhodamine-6-maleimide; and any combinations thereof.

Reactive and conjugated probes include but are not limited to:
Hydroxycoumarin; Aminocoumarin; Methoxycoumarin; Cascade Blue; Pacific Blue; Pacific Orange; Lucifer yellow; NBD; R-Phycoerythrin (PE); PE-Cy5 conjugates; PE-Cy7 conjugates; Red 613; PerCP; TruRed; Fluor X; Fluorescein; BODIPY-FL; Cy2; Cy3; Cy3B; Cy3.5; Cy5; Cy5.5; Cy7; TRITC; X-Rhodamine; Lissamine; Rhodamine B; Texas Red; Allophycocyanin (APC); APC-Cy7 conjugates; and any combinations thereof.

Nucleic acid probes include but are not limited to:
Hoechst 33342; DAPI; Hoechst 33258; SYTOX Blue; Chromomycin A3; Mithramycin; YOYO-1; Ethidium Bromide; Acridine Orange; SYTOX Green; TOTO-1, TO-PRO-1; TO-PRO: Cyanine Monomer; Thiazole Orange; Propidium Iodide (PI); LDS 751; 7-AAD; SYTOX Orange; TOTO-3, TO-PRO-3; DRAQ5; and any combinations thereof.

Cell function probes include but are not limited to:
Indo-1; Fluo-3; Fluo-4; DCFH; DHR; SNARF; and any combinations thereof.

Fluorescent proteins include but are not limited to:
Y66H; Y66F; EBFP; EBFP2; Azurite; GFPuv; T-Sapphire; Cerulean; mCFP; ECFP; CyPet; Y66W; mKeima-Red; TagCFP; AmCyanI; mTFP1; S65A; Midoriishi Cyan; Wild Type GFP; S65C; TurboGFP; TagGFP; S65L; Emerald; S65T; EGFP; Azami Green; ZsGreenl; TagYFP; EYFP; Topaz; Venus; mCitrine; YPet; TurboYFP; ZsYellowl; Kusabira Orange; mOrange; Allophycocyanin (APC); mKO; TurboRFP; tdTomato; TagRFP; DsRed monomer; DsRed2 ("RFP"); mStrawberry; TurboFP602; AsRed2; mRFP1; J-Red; R-phycoerythrin (RPE); B-phycoerythrin (BPE); mCherry; HcRedl; Katusha; P3; Peridinin Chlorophyll (PerCP); mKate (TagFP635); TurboFP635; mPlum; mRaspberry; and any combinations thereof.

A subclass of fluorescent particles includes quantum dots. Quantum dots are fluorescent semiconductor nanoparticles, whose electronic characteristics are closely related to the size and shape of the individual crystal. Generally, the smaller the size of the crystal, the larger the band gap, the greater the difference in energy between the highest valence band and the lowest conduction band becomes, therefore more energy is needed to excite the dot, and concurrently, more energy is released when the crystal returns to its resting state. For example, in fluorescent dye applications, this equates to higher frequencies of light emitted after excitation of the dot as the crystal size grows smaller, resulting in a color shift from red to blue in the light emitted. In addition to such tuning, a main advantage with quantum dots is that, because of the high level of control possible over the size of the crystals produced, it is possible to have very precise control over the conductive properties of the material. For example, quantum dots of different sizes can be assembled into a gradient multi-layer nanofilm.

Enhanced Effects of Photo-Induced Reactions—Generation of Reactive Species

As noted above, porphyrins constitutes a class of photosensitizers. Porphyrins are a group of organic compounds, many naturally occurring. One of the best-known porphyrins is heme, the pigment in red blood cells; heme is a cofactor of the protein hemoglobin. Porphyrins are heterocyclic macrocycles composed of four modified pyrrole subunits interconnected at their a carbon atoms via methine bridges (=CH—). Porphyrins are aromatic. That is, they obey Hückel's rule for aromaticity, possessing $4n+2\pi$ electrons (n=4 for the shortest cyclic path) delocalized over the macrocycle. Thus porphyrin macrocycles are highly conjugated systems. As a consequence, they typically have very intense absorption bands in the visible region and may be deeply colored. Porphyrins are the conjugate acids of ligands that bind metals to form complexes. The metal ion usually has a charge of 2+ or 3+. Several other heterocycles are related to porphyrins. These include corrins, chlorins, bacteriochlorophylls, and corphins Chlorins (2,3-dihydroporphyrin) are more reduced, contain more hydrogen than porphyrins, and feature a pyrroline subunit. This structure occurs in a chlorophyll molecule. Replacement of two of the four pyrrolic subunits with pyrrolinic subunits results in either a bacteriochlorin (as found in some photosynthetic bacteria) or an isobacteriochlorin, depending on the relative positions of the reduced rings. Some porphyrin derivatives follow Hückel's rule, but most do not.

Certain chemical compounds, including certain photosensitizers, are known to produce reactive oxygen species upon electromagnetic stimulation. Porphyrins, for example, can generate singlet oxygen upon light-induced excitation. Singlet oxygen (or $^1O_2$) is the common name used for an electronically excited state of molecular oxygen ($O_2$), which is less stable than the normal triplet oxygen. Because of its unusual properties, singlet oxygen can persist for over an hour at room temperature, depending on the environment. Because of differences in their electron shells, singlet and triplet oxygen differ in their chemical properties. Singlet oxygen is in the same quantum state as most molecules and thus reacts readily with them, thus making singlet oxygen highly reactive. Singlet oxygen is usually generated with a photosensitizer pigment. The damaging effects of sunlight on many organic materials (polymers, etc.) are often attributed to the effects of singlet oxygen. In photodynamic therapy, however, singlet oxygen is produced to kill cells, including cancer cells.

In addition, data presented herein demonstrate that the reactive nature of singlet oxygen produced by photosensitizers such as porphyrins can be used as an anti-microbial agent (e.g., antibiotic), and furthermore, such antibiotic effects can be enhanced when photosensitizers capable of generating reactive oxygen species are coupled to silk photonic crystals described herein. Data provided in the Exemplification below demonstrate enhanced photodynamic killing of bacteria using silk photonic crystals with porphyrin.

In some embodiments, the invention is useful for killing unwanted cells. In some embodiments, unwanted cells include microbes, such as bacteria and other pathogens. Such antibiotic agents may be used for a number of clinical applications. In some embodiments, silk photonic crystals coupled with a photosensitizer (such as porphyrin) are used for treating skin conditions. In some embodiments, such embodiments are useful for treating or preventing an infection. For example, topical formulations comprising silk photonic crystals coupled with a photosensitizer (such as porphyrin) can be used to treat and/or prevent infection on the skin. Such use is effective for treating skin wounds, such as laceration and burn. Topical formulations may be incorporated into a dressing (e.g., bandages). In some embodiments, silk photonic crystals coupled with a photosensitizer (such as porphyrin) are formulated into creams, ointments, lotions, sprays, emulsions, powders, and so on.

In some embodiments, silk photonic crystals coupled with a photosensitizer (such as porphyrin) may be used for sterilization to achieve asepsis. For instance, in healthcare environments, such embodiments may be used for sterilizing hands, clothing, equipment, etc. without concern for harmful effects of UV light, for example. It can be used before, during and/or after a surgical procedure or other medical and laboratory procedure.

In some embodiments, silk photonic crystals coupled with a photosensitizer (such as porphyrin) are useful for photodynamic therapy (PDT). The art is familiar with a wide array of photosensitizers for PDT, including but are not limited to: porphyrins, chlorophylls and dyes. Some examples include aminolevulinic acid (ALA), Silicon Phthalocyanine Pc 4, m-tetrahydroxyphenylchlorin (mTHPC), and mono-L-aspartyl chlorin e6 (NPe6). Several photosensitizers are commercially available for clinical use, such as Allumera, Photofrin, Visudyne, Levulan, Foscan, Metvix, Hexvix, Cysview, and Laserphyrin, with others in development, e.g. Antrin, Photochlor, Photosens, Photrex, Lumacan, Cevira, Visonac, BF-200 ALA, Amphinex, and Azadipyrromethenes. Although these photosensitizers can be used for wildly different treatments, they generally aim to achieve certain characteristics. Desirable characteristics include high absorption at long wavelengths, because tissue is much more transparent at longer wavelengths (~700-850 nm); therefore, absorbing at longer wavelengths would allow the light to penetrate deeper, and allow the treatment of larger tumors. Other desirable features include: high singlet oxygen quantum yield; low photobleaching; high chemical stability; low dark toxicity.

For PDT applications, the photosensitizer should not be harmful to the target tissue until the treatment beam is applied. It is also desirable that preferential uptake in target tissue can be achieved. The major difference between different types of photosensitizers is in the parts of the cell that they target. Unlike in radiation therapy, where damage is done by targeting cell DNA, most photosensitizers target other cell structures. For example, mTHPC has been shown to localize in the nuclear envelope and do its damage there. In contrast, ALA has been found to localize in the mitochondria and Methylene Blue in the lysosomes. Generally, to allow treatment of deeper tumors some researchers are using internal chemiluminescence to activate the photosensitiser. In any such PDT applications, silk photonic crystals described herein can be used to enhance effects.

Accordingly, in some embodiments, unwanted cells include cancer cells (e.g., malignant tumor cells) and/or blood vessel cells, such as endothelial cells, that supply blood to solid tumors, including during tumor angiogenesis. Embodiments described herein may also be used to target unwanted cells or tissues using specific targeting moiety or moieties known in the art. These include targeting moieties that bind to tumor-specific antigens, including those expressed on the surface of tumor cells. In that way, tumor cells or tissues may be specifically targeted for light-induced killing.

EXEMPLIFICATION

The following section is provided to illustrate non-limiting embodiments of the present invention and is not to be construed to be limiting in any way.

Example 1

SIO Coupled to Thermogenic Plasmonic Nanoparticles

Since the beginning of human civilization, natural materials have served as an extraordinary source for medical application such as using nacre for dental implants in Mayan cultures and spider webs as wound dressing in Greeks and Romans times[1,2]. Silk, a highly desired and used textile spread around the World through the Silk-road from ancient China over the past five millennia, can be retooled to provide new opportunities in biomedical application at the overlap of technology and biology owing to its excellent mechanical and optical properties along with biocompatibility, and biodegradability[3,4]. In some embodiments, silk fibroin obtained from the *Bombyx mori* caterpillar can have outstanding properties as a transparent optical material[5]. These properties can facilitate the creation of a variety of optical components such as microlens arrays[6], waveguides[7], and diffraction gratings[8] by simple patterning of silk films. In some embodiments, silk fibroin can be a biologically favorable carrier that enables bio-dopants to maintain their functionalities[9,10].

Photonic micro- and nano structures can provide the opportunity to manipulate photons within small volumes for biophotonic applications[11-15]. Photonic crystals (PhC) can be useful to control the density of photon states by creating a medium with artificially designed periodic structures in one, two, and three dimension[16]. In the present disclosure, among other things, the manufacturing of free-standing three dimensional PhCs with different lattice constants in the structural form of an inverse opal entirely composed of silk fibroin (a silk inverse opal or SIO) is shown and described. These 3D-nanostructured samples can exhibit structural color. Theoretical calculations of the photonic bandgap (PBG) can be paired with experimental characterization of the device's spectral responses. In some embodiments, the colorimetric response of the SIOs can be tuned by immersing the SIOs in a liquid. In some embodiments, by employing gold nanoparticles (Au-NPs) in the SIOs, the absorption by the Au-NPs can be enhanced by the SIOs. Such embodiments can contemplate the possibility of laser-heating therapy applications.

Figure 2:
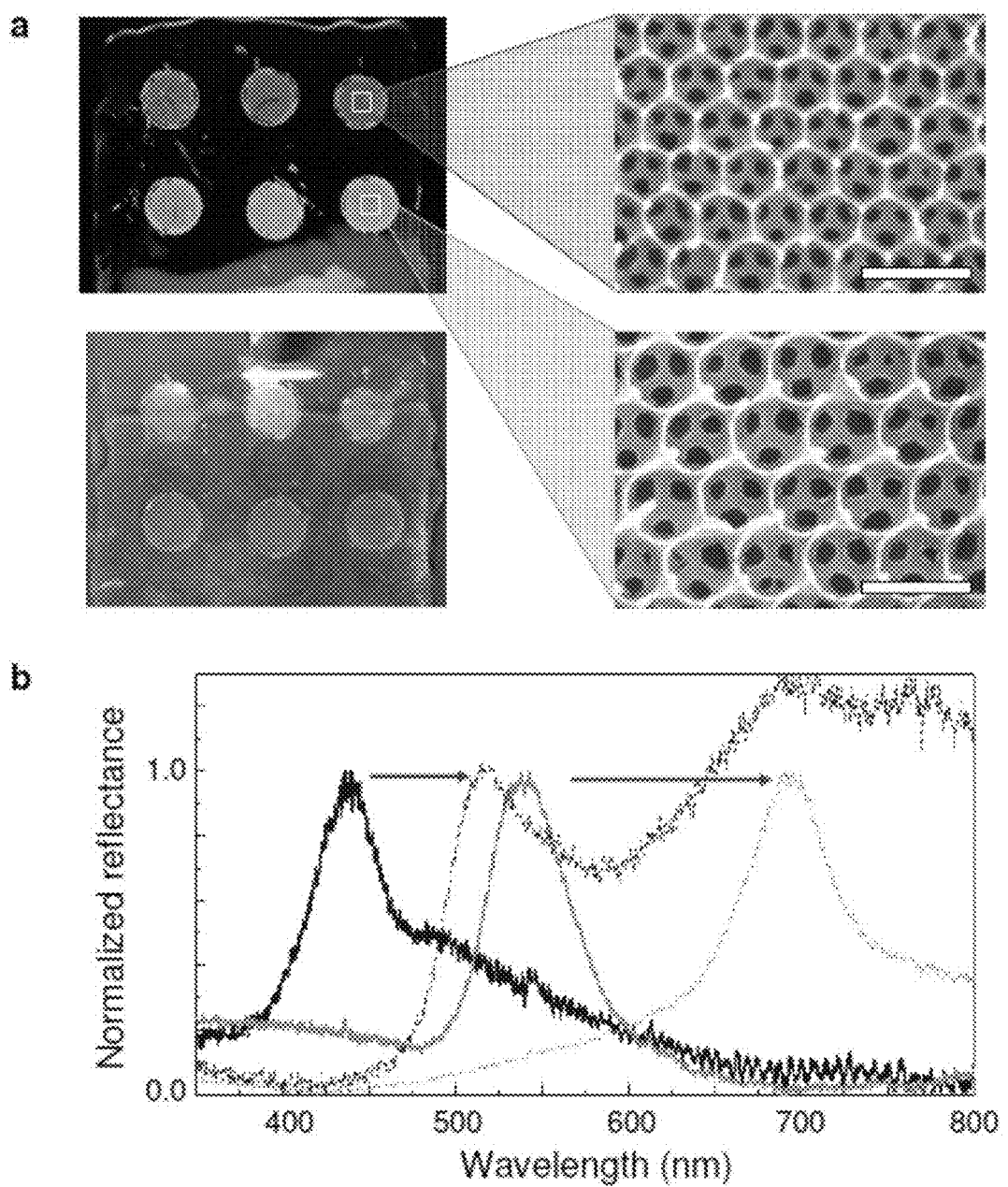
FIG. 2 depicts exemplary optical responses of SIO films. a) Photography-image taken under white light illumination in air (top left) and acetone (bottom left), showing clear structural color change. And SEM image of blue (top right) and green opal (bottom right) in the SIO film. All scale bares represent 500 nm. All images are captured in the direction perpendicular to the SIO film. b) Reflectance spectra obtained from blue (blue solid curve) and green opal (green solid curve) in air. Reflectance peaks are red-shifted when the SIO is immerged in acetone (dashed curve).

A template-method based on the use of poly(methyl methacrylate) (PMMA) submicron spheres can be used to fabricate the SIO[17]. The fabrication procedures are described in FIG. 1, and can begin with PMMA submicron-spheres layers. The spheres can have diameters of 250, 320, or 350 nm and can be stacked with a face-centered cubic (FCC) structure, onto a silicon substrate An aqueous solution of fibroin extracted from *B. Mori* silkworm cocoons can be poured to fill the template and allowed to solidify into an amorphous free standing silk film. To obtain the inverse silk opal structure, the silk film can be detached from the silicon substrate and immersed into acetone, thereby dissolving the PMMA spheres. The process can be accompanied by the appearance of structural color within the transparent silk film. The resulting free standing silk film with the inverse opal structures is also shown in FIG. 2(*a*). A scanning electron microscope (SEM) image of a section of the sample in FIG. 2(*a*) shows the nanostructure with the ordered voids resulting from the PMMA spheres template for both green and blue iridescences. Inspection of the SEM images reveals a slight contraction of the lattice constant with measured center-to-center (CTC) distances of the air-void diameters that appear to have become smaller (240, 280, and 300 nm) than the diameter of PMMA spheres. In some embodiments, the diameters of the voids can be smaller than the diameters of the PMMA spheres due to contraction of the silk film in response to prolonged exposure to acetone.

Figure 3:
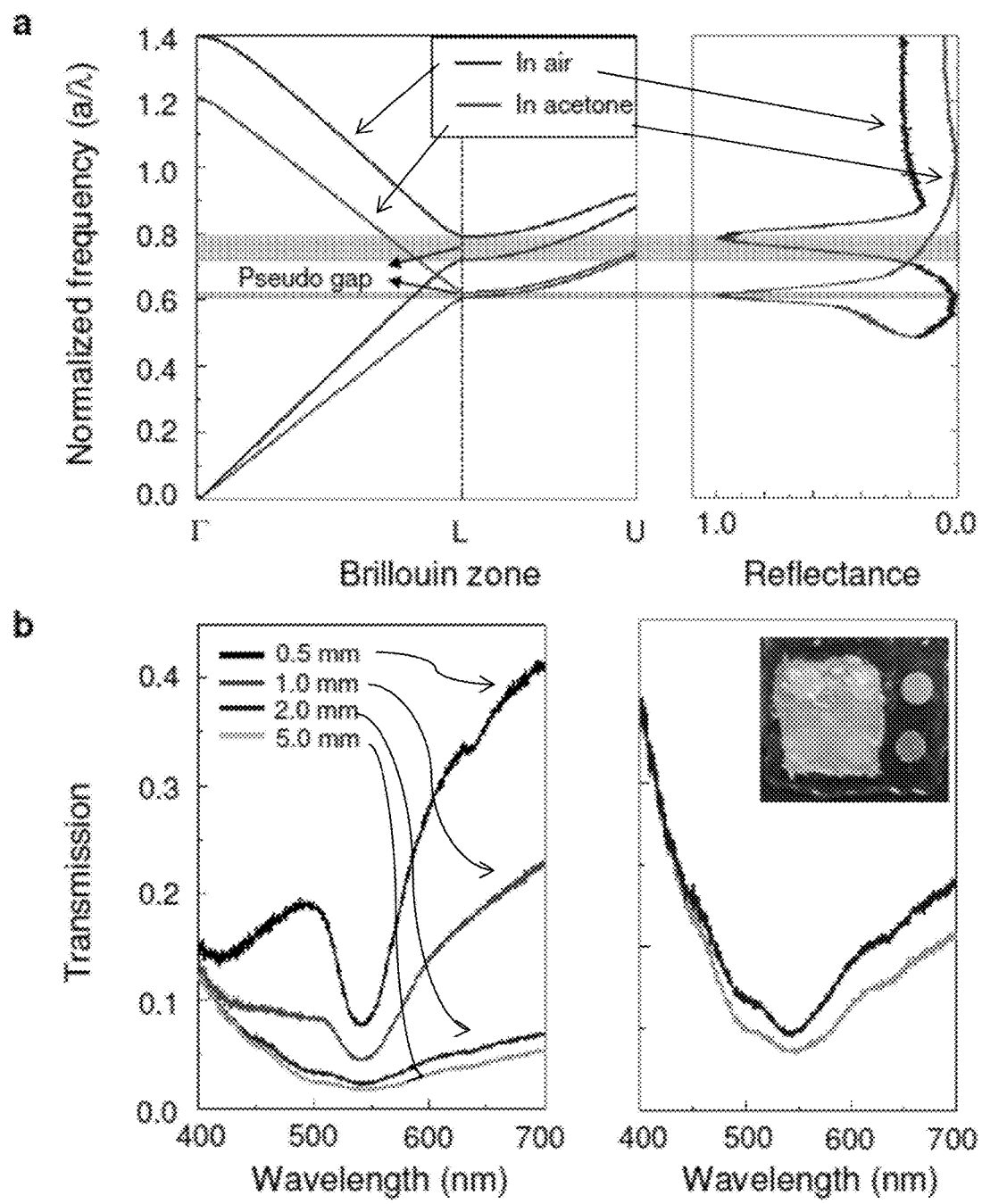
FIG. 3 depicts exemplary optical responses of SIO films. a) Photonic band-structure of the SIO in air (blue) and acetone (red) calculated using the plane-wave expansion method. Refractive index used in the simulation is 1.54 for silk, 1.00 for air, and 1.36 for acetone. Frequency-domain reflectance spectra for the SIO with the lattice constant of 300 nm are plotted to compare with the band-structure. b) Transmission spectra for the SIO with 300 nm which is under tissue-slices with different thicknesses. To emphasize a transmission dip in thick tissue, magnified spectra is plotted in right side. The inset is a photography-image of the SIO film underneath thin biological tissue (0.5 mm thick). To protect the SIOs, a cover glass was inserted between the tissue and the SIOs.

Without wishing to be bound by theory, the observed structural color can be due to the diffraction of incident light induced by the silk nanostructured lattice. In some embodiments, the diffraction can be quantified theoretically by calculating the photonic band gap (PBG) associated to the lattice geometry and index of refraction[18, 19] and by the diffraction theory (called the Bragg-Snell formula). The silk inverse opals presented here are three dimensional face-centered cubic (FCC) photonic crystal with a pseudo-PBG in the L-point, [111] crystal direction, of the FCC lattice, which corresponds to the vertical direction of the SIO film. Due to the existence of the pseudo-PBG in the silk inverse opal, vertically incident light with frequencies that fall within the PBG can be reflected by the SIO. The frequency of the PBG can be controlled by changing the lattice constant of the opal, accomplished by using different diameter PMMA spheres, which in turn can change the center-to-center distance of the voids in the inverse opal, or the index contrast of the structure, accomplished either by doping the silk or by filling the structure. Two structural colors and their corresponding measured spectral response under white light illumination, blue centered at $\lambda=438$ nm with a SIO lattice constant $\lambda=240$ nm and green centered at $\lambda=540$ nm with a SIO lattice constant $\lambda=300$ nm, are shown in FIG. 2(*b*). These colors can be red-shifted when the SIO is immersed in acetone thereby lowering the index contrast (FIG. 2(*a*)). As shown in the calculated band-structure in FIG. 3(*a*), the PBG can be shifted to higher frequency as the refractive index of environment increases. The spectral responses for white light were experimentally evaluated using an optical set-up, collecting visible-NIR reflectance spectra. In FIG. 2(*b*), the peaks of reflectance spectra are clearly shown, and are red-shifted as changing to refractive index of acetone. The positions of the peaks and the shift are in agreement with the theoretical estimation from the PBG calculation.

The ability to manufacture a 3D PBG structure out of silk offers additional opportunities because of, the biocompatible and implantable attributes of the material. An example of possible application is to engineer structural color that can be implanted to provide spectral signatures that are non-endogenous and can be used as a contrast agent without resorting to dyes or chemicals. This can be validated by performing an in-vitro experiment in which the SIO is placed under slices of scattering tissue (chicken breast) of variable thickness. The results shown in FIG. 3(*b*) show the ability to detect the spectral response due to the PBG underneath 5 mm of tissue.

Figure 4:
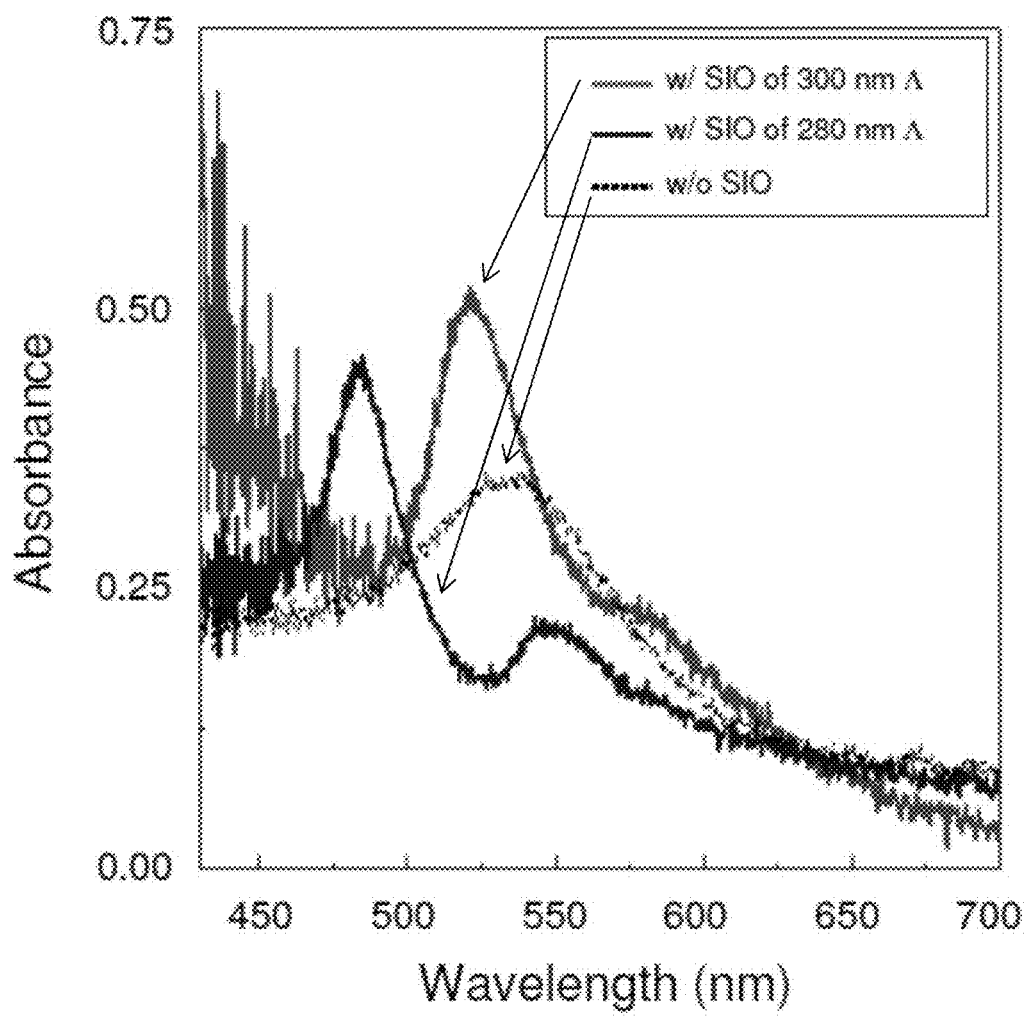
FIG. 4 depicts exemplary absorption enhancements by the photonic band-edge. Absorption spectra obtained from the Au-NP-doped SIO film, with a lattice constant of 280 nm (blue solid line) and 300 nm (red solid line). For a comparison, an absorption spectrum of the Au-NP-doped silk without opal structure is taken (black dot line). The film without opal that has 4 times higher doping concentration (0.16 wt %) than the SIOs was used to show the clear surface plasmonic absorption peak.

The ease with which silk can be doped can enable the manufacturing of functional opals and extend the application space provided by this fabrication technique. For example, a gold nanoparticle doped silk can be used to manufacture a functional SIO. By matching the PBG of the opal to the surface plasmon absorption of the Au-NPs, surface plasmon absorption of the Au-NPs can be enhanced. The Au-NP-doped SIO can be manufactured similarly to other techniques described herein. The Au-NP-SIOs integrated in the film can have slightly different PBG, in which the reflectance peaks are at found to occur at $\lambda=512$ nm and $\lambda=546$ nm. As shown in FIG. 4, the measured absorption-spectra of the Au-NP-SIOs can have two shoulders, appearing near the wavelength of the reflectance peaks signifying that Au-NP absorption is enhanced by the photonic band-edge. As described in previous studies[20-22], at the photonic band-edge, an energy flow of photons can slowly propagate through the photonic crystal so that the interaction between the photon flow and the bulk material can be maximized. Even if the filling fraction of the SIOs (determined by, e.g., the fraction of space occupied by the SIO in unit cell of FCC structure) is only 0.26, the localized photons at the band-edge suggest that the structure can increase the coupling efficiency between the light and the Au-NPs, along with the increased optical path due to scattering.

Figure 5:
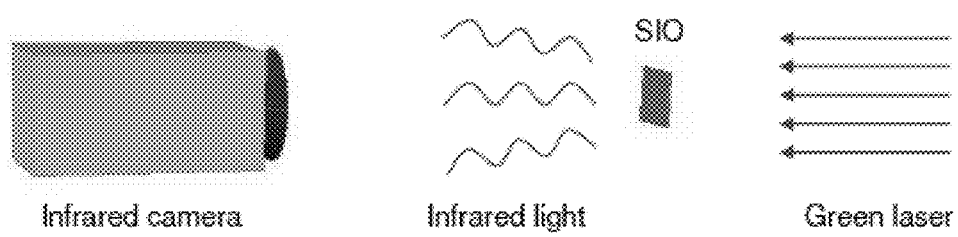
FIG. 5 depicts exemplary thermal properties laser-heated SIO films. a) Schematic diagram of laser heating experiment on the Au-NP-doped SIO film. b) Temperature profile of the SIO film when the sample is illuminated on entire film with the power density of 1.05 W/cm2. The silk film and each SIO are indicated by dashed line. c) Temperature profiles on the silk film for unpatterned (left), blue opal (middle), and green opal (right) under the illumination on spot with 2.25 mm diameter. All scale bars represent 2 cm.
Figure 5:
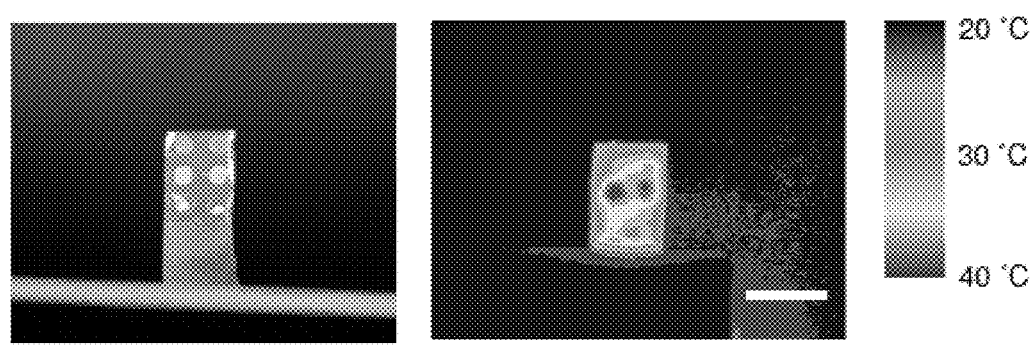
Figure 5:
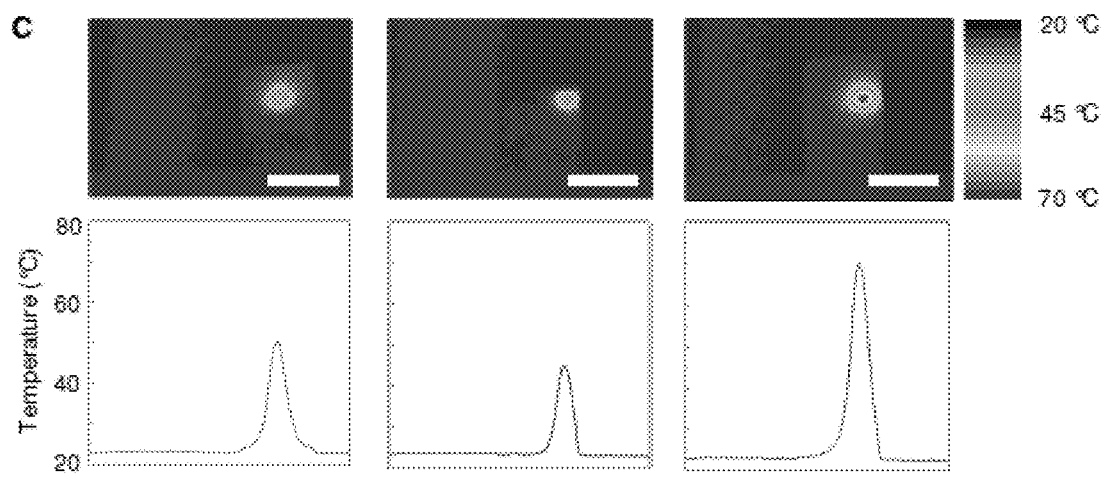
Figure 6:
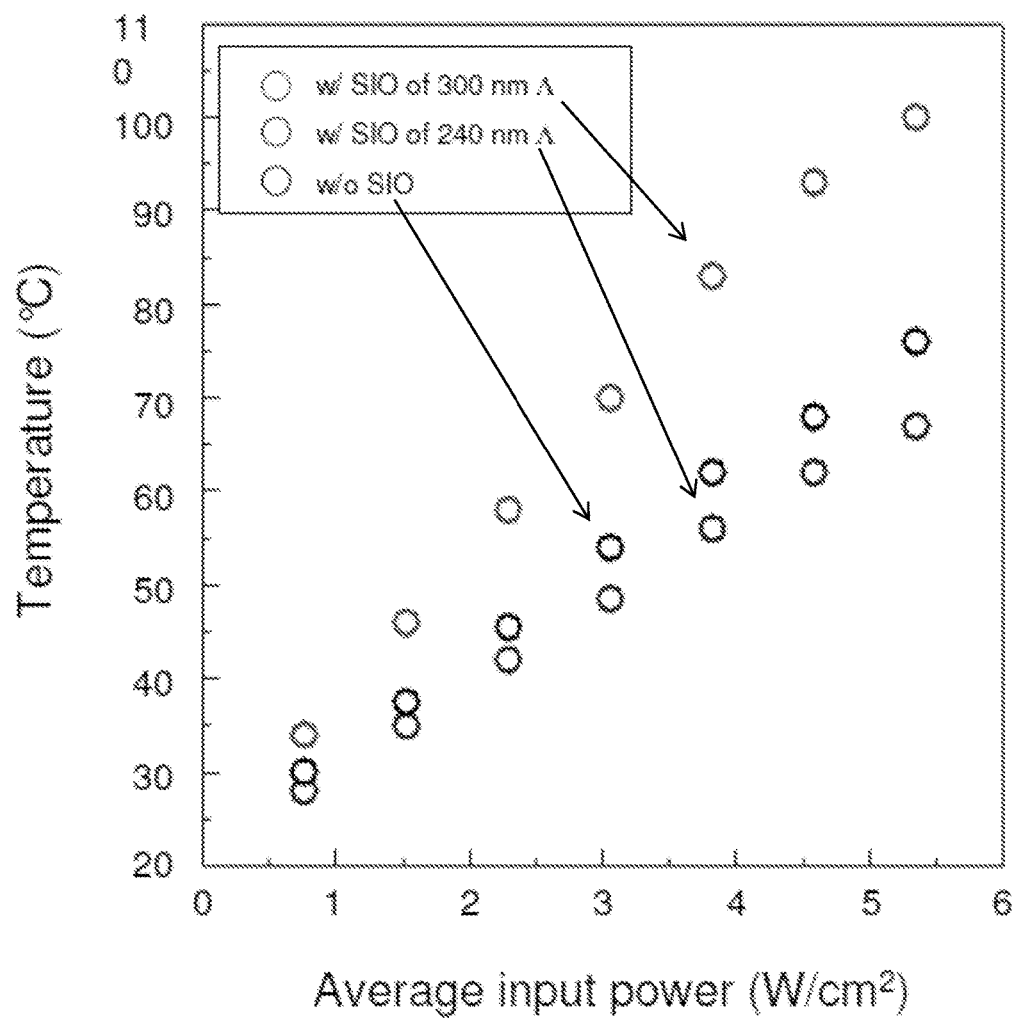
FIG. 6 depicts exemplary temperature increases for silk inverse opals with different lattice constants.

The combination of form (through the photonic lattice) and function (through the Au-NP doping) can add utility to photonic lattices through the activation of its constituent material. The inclusion of Au-NPs can allow for laser plasmon resonance induced heating. This effect can be used in biomedical applications to target and eliminate diseased tissues[23-25]. An Au-NP PhC can allow enhancing absorption and potentially reducing the amount of laser radiation needed to induce the necessary temperature differential. FIG. 5(*a*) shows an exemplary schematic diagram for laser-heating Au-NP-doped SIOs. An exemplary sample can be illuminated with green laser light at a wavelength with $\lambda=532$ nm wavelength and 1.05 W/cm² incident power, the average laser power that is divided by a beam diameter. The laser beam can be expanded to 2 cm diameter to cover the entire sample which was illuminated for 5 minutes to reach a measurable equilibrium temperature (see Methods). FIG. 5(*b*) illustrates an exemplary temperature distribution in the sample acquired with a thermal camera. The SIO engineered to have a PBG centered at $\lambda=546$ nm can match closely the absorption peak of the Au-NP and shows a measured increase in temperature of 7° C. when compared with the unpatterned silk film and with the structured portion of the film with the engineered bandgap in the blue. As shown in FIG. 4, the 532 nm wavelength can overlap onto the enhanced absorption spectrum, and the absorption of the Au-NPs can be enhanced by the effect of the photonic band-edge providing evidence that the structured lattice can help increase the efficiency of laser-heating.

The temperature increase for the individual SIOs can be tested using a collimated laser beam directed onto the lattices, and the collimated laser beam can be used to investigate the effect of the band-edge. FIG. 5(c) depicts exemplary temperature maps for unpatterned, blue, and green lattices when each sample was illuminated by the green laser with 3.06 W/cm² incident power with a 2.25 mm beam diameter. The temperature on the green silk opal can increase to about 70° C., about 20° C. higher than that in blue opal and unpatterned film. Comparisons between the blue and green SIOs can provide evidence that the main cause for temperature rising is not poor thermal conductivity of air voids, but the enhancement of absorption at the band-edge.

SIO can suggest a novel scheme of bioapplication with unique and outstanding characteristics in the material aspect of silk and the photonic aspect of inverse opal and SPR. High quality SIO film can be fabricated by a cheap and easy way based on the PMMA spheres template, and be confirmed by the clear structural colors and the measurement of the reflectance including the comparison with the photonic band-structure calculation. Efficient laser-heating can be achieved by, for example, the combination of the roles of the photonic band-edge and SPR. The SIO can be an applicable building block in biophotonic chip to biomedical applications such as laser-heating therapy, sensing, and drug delivery.

By the incorporation of biological molecules in the PhC, it can be possible to control the rates and directions in which molecule emit light. A biomolecule binding within the PhC can produce a change in the spacing of the composites or in the refractive index of the surrounding medium. These schemes can lead to efficient and novel functionalities in biological detection.

Methods

Silk Fibroin Solution Preparation

Cocoons of the *Bombyx mori* silkworm can be boiled for 30 minutes in a solution of 0.02M $Na_2CO_3$ to remove the sericin protein[6-8]. The extracted fibroin can be rinsed with distilled water and then dried in ambient air for 12 hours. After drying, the fibroin can be dissolved in a 9.3M LiBr solution at 60° C. for 4 hours, yielding a 20 wt % aqueous solution, and subsequently the solution can be dialyzed against distilled water using a dialysis cassette (Slide-a-Lyzer, Pierce, MWCO 3.5K) at room temperature for 48 hours until the solution reaches a concentration of 8 wt %. The obtained solution can be purified using a centrifuge and a 0.8 m syringe filter.

SIO Fabrication

PMMA submicron spheres can be purchased to fabricate an opal template (1% concentration dispersed in water, Phosphorex Inc., Fall River Mass.). The PMMA solution can be dropped onto silicon wafer and then the wafer can be heated on hot-plate at 90° C. to self-assembly generate the PMMA opal induced by water-evaporation. Silk solution can be added to the PMMA opal and can fill the air voids by capillary infiltration. Film can be set to dry for 24 hours at room temperature and standard humidity. The silk film can be detached from the silicon wafer and soaked in acetone for 24 hours to remove the PMMA spheres. To incorporate Au-NPs in the silk film, the Au-NPs solution (5 nm diameter NPs, Microspheres-Nanospheres) can be mixed with the silk solution before the casting. The concentration of the Au-NPs can be 0.04 wt %, by way of example.

Simulation

The photonic band-structure which was simulated by a plane-wave expansion method was achieved using the MPB software package developed at MIT. Three dimensional simulations were performed to calculate 6 bands. In the simulation, each lattice vector was divided into 32 computational grids. Refractive index is 1.54 for silk and 1.36 for acetone. The lattice constant in the simulated band-structure is defined as the CTC distance multiplied by $\sqrt{2}$.

Measurement

Spectra can be measured using a VIS/NIR fiber optic spectrometer (USB-2000, Ocean Optics). White light can be propagated through the fiber to illuminate the SIOs. The reflected signal can be coupled into same fiber tip and projected into the spectrometer. The distance between the fiber tip and sample can be fixed at 500 m. A reference signal can be collected using an aluminum mirror. In the transmission measurement, white light can be illuminated from back-side of the SIOs, and fiber tip collected the transmitted signal from the front-side of the SIOs. In some embodiments, the fiber has a 0.22 numerical aperture and a 400 m core diameter.

Laser-Heating

The frequency-doubled Nd; Vanadate (Nd; YVO4) laser that provides single-frequency green (532 nm) output (Verdi V-10, Coherent) can be used for laser-heating experiment. To illuminate an entire area of the SIO film, a convex lens which has a focal length of 10 cm can expand the laser beam to 2 cm diameter. The beam diameter which can be determined by the circle with a half intensity of Gaussian-beam shape can be acquired from a translate-stage mounted fiber that is coupled to the spectrometer. For the investigation for the individual SIOs, in some examples, no optics are adapted. In some embodiments, the laser beam from Nd; YVO4 laser can directly illuminate the individual SIOs. Temperature distribution of the SIO film can be measured by the thermal camera (SC-600, FLIR). Data can be obtained after 5 minutes for the sample to reach the stable temperature. The laser power can be measured using a laser power meter (Molectron Power MAX 500D, Coherent).

Figure 7:
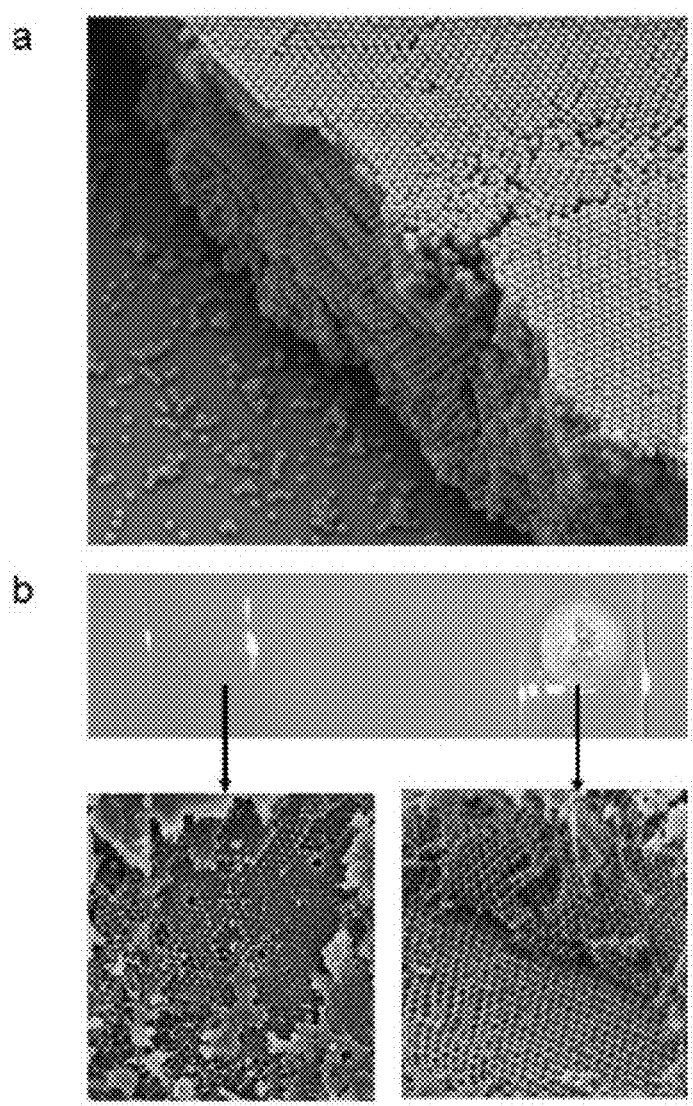
FIG. 7 depicts exemplary images of different PMMA opal structures.

Referring now to FIG. 7, SEM images of PMMA opal structures are shown and described. FIG. 7(a) depicts a PMMA opal structure. To observe the vertical profile, a small portion of the sample can be scraped out using a sharp razor blade. FIG. 7(b) depicts a PMMA opal structure before (left) and after (right) dissolving PMMA spheres in acetone. The left film is almost transparent due to small refractive index contrast between PMMA spheres ($n_{PMMA}$=1.49) and silk ($n_{silk}$=1.54). As the PMMA spheres dissolve, clear structural color can appear due to the diffraction by the SIO. SEM images (bottom) confirm the SIO does not contain PMMA spheres.

Diffraction Theory for the SIO

In some researches[26, 27], the phenomenon has been also analyzed using the Bragg-Snell formula, as follows:

$$m\lambda_{Bragg}=2D\sqrt{n_{eff}^2-sin^2\theta}, \quad (1)$$

where m is the diffraction order, D is the inter-planar spacing in the (111) direction which is perpendicular to the film, is the incidence angle from the normal, and $n_{eff}$ is the effective refractive index. This parameter can be theoretically calculated with the Lorentz-Lorentz formula for the effective medium:

$$\frac{n_{eff}^2 - 1}{n_{eff}^2 + 2} = f \frac{n_{sphere}^2 - 2}{n_{sphere}^2 + 2} + \frac{(1-f)(n_{void}^2 - 1)}{n_{void}^2 + 2}, \quad (2)$$

where $n_{sphere}$ and $n_{void}$ are the refractive index of the materials of the sphere and the void, respectively, and f is the filling factor of the spheres in the structure. The PBG theory and the Bragg-Snell formula can provide same interpretation only for the determination of reflectance peaks. Further information for the diffraction in the opal structure such as angles, intensities, and bandwidths, can be analyzed and understood using dynamical diffraction theory[28].

Calculation of the Filling Factor in FCC Structure

Figure 8:
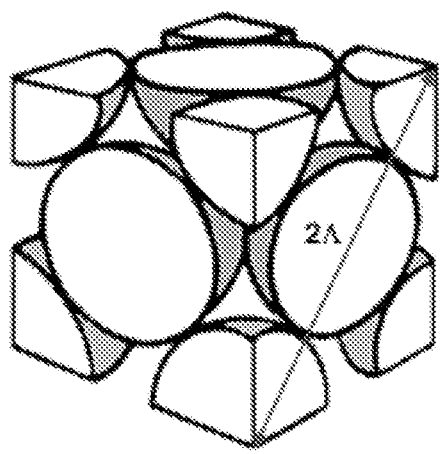
FIG. 8 depicts an exemplary graphic demonstrating the calculation of the filling factor. The schematic of the unit cell in a FCC crystal structure. is a lattice constant.

FIG. 8 describes an exemplary unit cell of FCC crystal. A volume of the unit cell) ($V_C$) is $2\sqrt{2}\Lambda^2$. In close-packed system, four spheres with a diameter of inside the unit cell. Thus, the total volume of the spheres ($V_S$) is $$\frac{2}{8}\pi\Lambda^2.$$

The filling factor of the spheres in FCC can be defined as $$\frac{V_S}{V_C} \approx 0.74.$$

Because the SIO has air-spheres, the filling factor of silk can be 0.26.

Absorption-Enhancement at the Photonic Band-Edge

Figure 9:
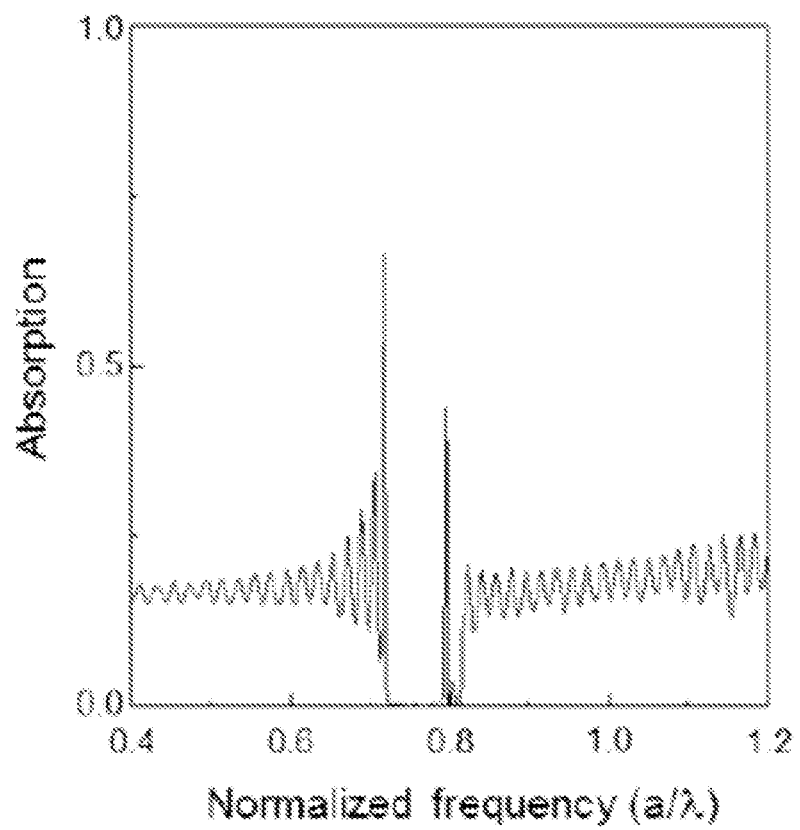
FIG. 9 depicts an exemplary graph of absorption-enhancement at the band-edge. Absorption spectrum can be simulated for the inverse silk opal with uniform loss ($\epsilon_{silk}=1.54^2+0.001i$).
Figure 10:
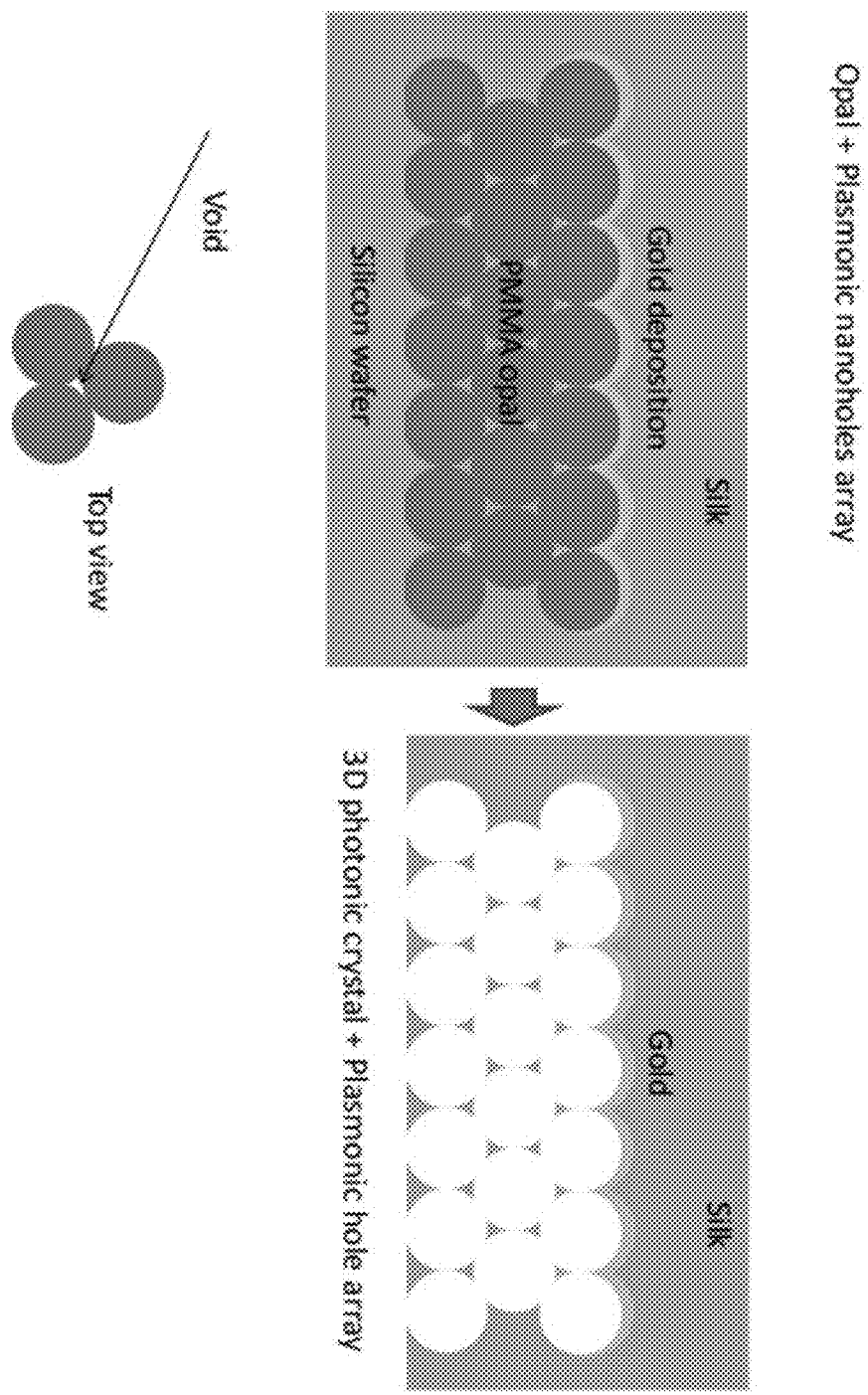
FIG. 10 depicts an exemplary method of fabricating a silk inverse opal (SIO).
Figure 11:
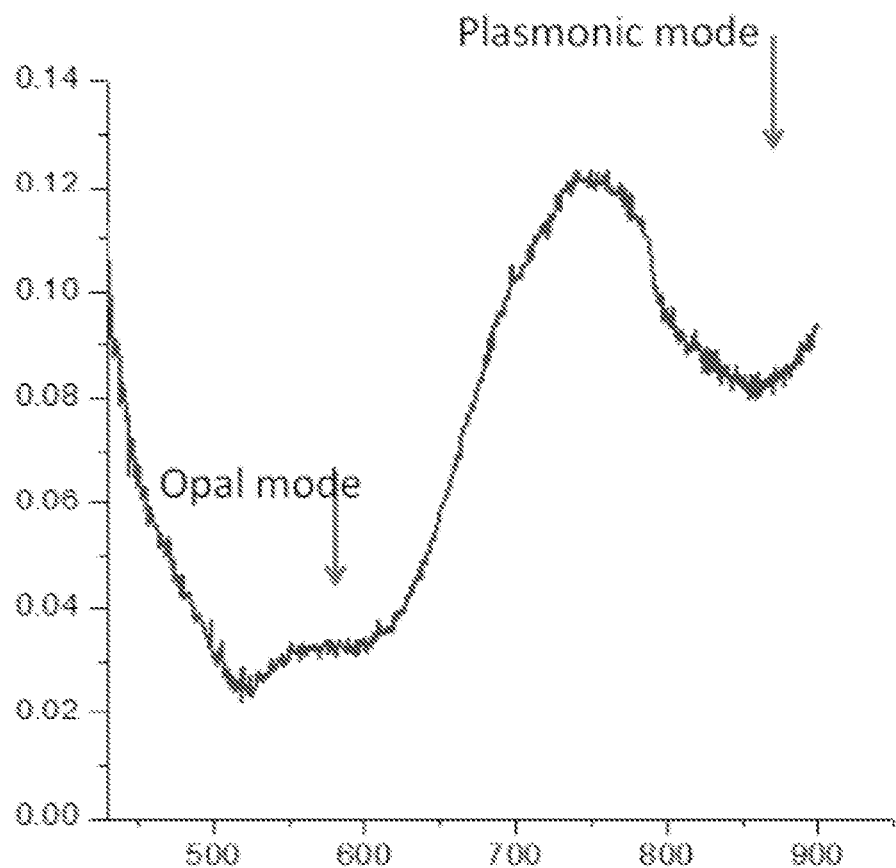
FIG. 11 depicts exemplary transmission data of a silk inverse opal in the opal and plasmonic modes.
Figure 12:
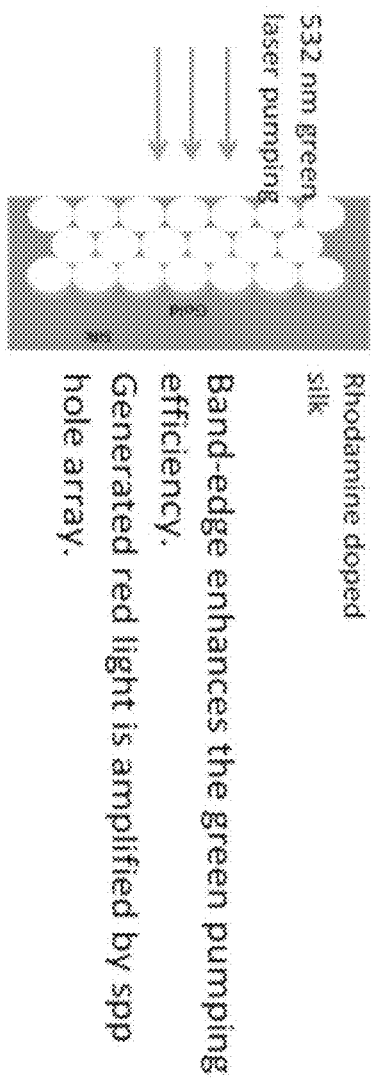
FIG. 12 depicts exemplary applications of silk materials with structural color.
Figure 12:
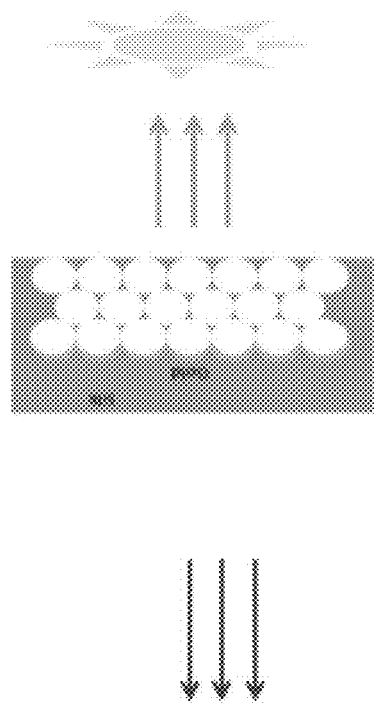
Figure 13:
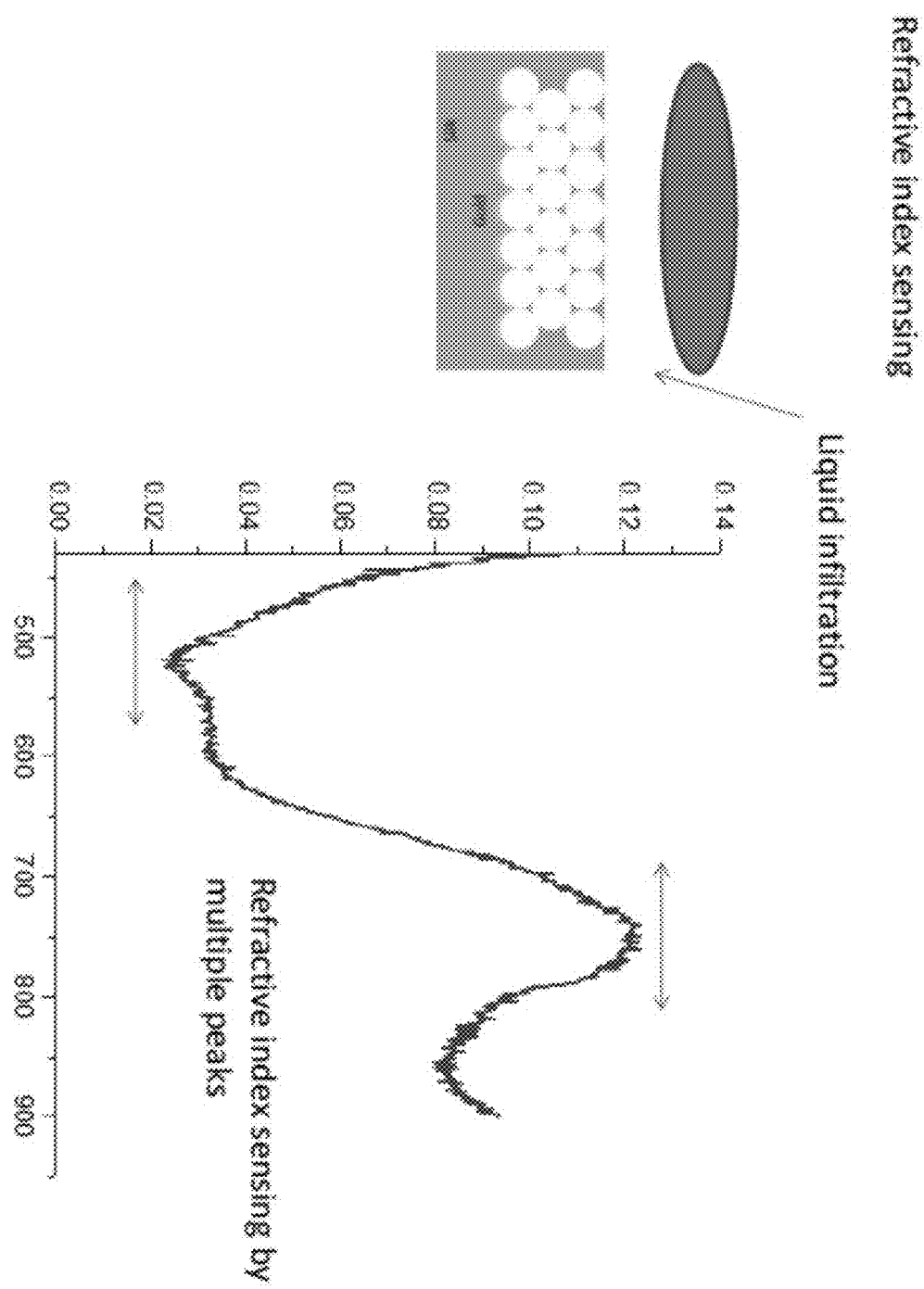
FIG. 13 depicts exemplary refractive index sensing data of a silk inverse opal (SIO).

The PhC can have a trait to control a flow of photons due to their periodicity. Without wishing to be bound by theory, the photons, for example, can be trapped in a tiny cavity at the frequency inside the PBG, or propagated through the medium with extremely slow group velocity at the photonic band-edge, the point with zero slopes in the photonic band-structure. When the PhC contains quantum elements, such as metal nanoparticle, quantum dot, and quantum well, it can provide a way to control their emission or absorption characteristics. The enhancement of absorption of the Au-NPs shown at the photonic band-edges, two ends that define the L-point PBG, can be investigated. To support the enhancement, a finite-differential time-domain (FDTD) simulation can be conducted using the MEEP, open source FDTD software distributed by MIT. A medium that has uniform loss (imaginary dielectric constant) can be employed instead of the Au-NPs. A plane-wave with TE polarization (parallel electric field to inverse opal film) can be incident from bottom of the structure and its flux in both top and bottom can be monitored to collect reflected and transmitted fluxes. FIG. 9 shows the calculated absorption-spectrum. The absorption was strongly enhanced at the band-edge location for the band-gap in the photonic structure[29]. Though ideal circumstances, like polarized plane-wave, uniform loss, and infinite lateral structure, were considered in the simulation, it would be a strong evidence to support the phenomena of the absorption-enhancement.

REFERENCES

1 Rather, B., Hoffman, A., Schoen, F. & Lemon, J. Biomaterials Science: an introduction to materials in medicine. (Academic Press, 2004).
2 Scheibel, T. Spider silks: recombinant synthesis, assembly, spinning, and engineering of synthetic proteins. Microb. Cell Fact. 3, 14-23 (2004).
3 Omenetto, F. G. & Kaplan, D. L. New opportunities for an ancient material. Science 329, 528-531 (2010).
4 Leal-Egana, A. & Scheibel, T. Silk-based materials for biomedical applications. Biotechnol. Appl. Biochem. 55, 155-167 (2010).
5 Omenetto, F. G. & Kaplan, D. L. A new route for silk. Nature Photon. 2, 641-643 (2008).
6 Lawrence, B. D., Cronin-Golomb, M., Georgakoudi, I., Kaplan, D. L. & Omenetto, F. G. Bioactive silk protein biomaterial systems for optical devices. Biomacromolecules 9. 1214-1220 (2008).
7 Parker, S. T., Domachuk, P., Amsden, J., Bressner, J., Lewis, J. A., Kaplan, D. L. & Omenetto F. G. Biocompatible silk printed optical waveguides. Adv. Mater. 21, 2411-2415 (2009).
8 Perry, H., Gopinath, A., Kaplan, D. L., Negro, L. D. & Omenetto F. G. Nano- and micropatterning of optically transparent, mechanically robust, biocompatible silk fibroin films. Adv. Mater. 20, 3070-3072 (2008).
9 Demura, M., Asakura, T., Nakamura, E. & Tamura, H. Immobilization of peroxidase with a Bombyx mori silk fibroin membrane and its application to biophotosensors. J. Biotech. 10, 113-119 (1989).
10 Domachuk, P., Perry, H., Amsden, J. J., Kaplan, D. L. & Omenetto, F. G. Bioactive "self-sensing" optical systems. Appl. Phys. Lett. 95, 253702 (2009).
11 Prasad, P. N. Introduction to biophotonics. (John Wiley, 2003).
12 Alivisatos, P. The use of nanocrystals in biological detection. Nature Biotech. 22, 47-52 (2004).
13 Kim, S. -H., Lee, S. Y., Yang, S. -M. & Yi, G. -R. Self-assembled colloidal structures for photonics. NPG Asia Mater. 3, 25-33 (2011).
14 Asher, S. A., Peteu, S. F., Reese, C. E., Lin, M. X. & Finegold, D. Polymerized crystalline colloidal array chemical-sensing materials for detection of lead in body fluids. Anal. Bioanal. Chem. 373, 632-638 (2002).
15 Bonifacio, L. D., Puzzo, D. P., Breslav, S., Willey, B. M., McGeer, A. & Ozin G. A. Towards the photonic nose: a novel platform for molecule and bacteria identification. Adv. Mater. 22, 1351-1354 (2010).
16 Yablonovitch, E. Inhibited spontaneous emission in solid-state physics and electronics. Phys. Rev. Lett. 58, 2059-2062 (1987).
17 Xia, Y., Gates, B., Yin, Y. & Lu. Y. Monodispersed colloidal spheres: old materials with new applications. Adv. Mater. 12, 693-713 (2000).
18 Wijnhoven, J. E. G. J. & Vos, W. L. Preparation of photonic crystals made of air spheres in titania. Science 281, 802-804 (1998).
19 Tarhan, I. I. & Watson, G. H. Photonic band structure of fcc colloidal crystals. Phys. Rev. Lett. 76, 315-318 (1996).
20 Kim, S., Lee, J., Jeon, H. & Kim. H. J. Fiber-coupled surface-emitting photonic crystal band edge laser for biochemical sensor applications. Appl. Phys. Lett. 94, 133503 (2009).
21 Tan, Y., Quan, W., Ding, S. & Wang, Y. Gold-nanoparticle-infiltrated polystyrene inverse opals: a three-dimensional platform for generating combined optical properties. Chem. Mater. 18, 3385-3389 (2006).
22 Sanchez-Sobrado, O., Lozano, G., Calvo, M. E., Sanchez-Iglesias, A., Liz-Marzan, L. M. & Miguez, H. Interplay of resonant cavity modes with localized surface plasmons: optical absorption properties of Bragg stack integrating gold nanoparticles. *Adv. Mater.* 23, 2108-2112 (2011).
23. Lal, S., Clare, S. E. & Halas, N. J. Nanoshell-enabled photothermal cancer therapy: Impending clinical impact. *Acc. Chem. Res.* 41, 1842-1851 (2008).
24. Qin, Z. & Bischof, J. C. Thermophysical and biological responses of gold nanoparticle laser heating. *Chem. Soc. Rev.* (Advance article).
25. Jain, P. K., Huang, X., El-Sayed, I. H. & El-Sayed, M. A. Noble metals on the nanoscale: optical and photothermal properties and some applications in imaging, sensing, biology, and medicine. *Acc. Chem. Res.* 41, 1578-1586 (2008).
26. Vos, W. L., Sprik, R., Blaaderen, A., Imhof, A., Lagendijk, A. & Wegdam, G. H. Strong effects of photonic band structures on the diffraction of colloidal crystals. *Phys. Rev. B* 53, 16231 (1996).
27. Morandi, C., Marabelli, F., Amendola, V., Meneghetti, M. & Comoretto, D. Light localization effect on the optical properties of opals doped gold nanoparticles. *J. Phys. Chem. C* 112, 6293-6298 (2008).
28. Pan, G., Sood, A. K. & Asher, S. A. Polarization dependence of crystalline colloidal array diffraction. *J. Appl. Phys.* 84, 83-86 (1998).
29. Florescu, M., Lee, H., Stimpson, A. J. & Dowling, J. Thermal emission and absorption of radiation in finite inverted-opal photonic crystals. Phys. Rev. A 72, 033821 (2005).

Example 2

Silk-Based Hybrid Photonic-Plasmonic Crystal with Improved Sensing Capability

Referring to FIGS. 14 to 17, a silk-based hybrid photonic-plasmonic crystal (HPPC) structure for use as a refractive index (RI) sensor was prepared. The hybrid structure is composed of a silk inverse opal (SIO) and a thin silver (Ag) film deposited on the structured surface of the inverse opal surface and was fabricated using a template method as described in S. Kim, A. N. Mitropoulos, J. D. Spitzberg, H. Tao, D. L. Kaplan, F. G. Omenetto, *Nature Photon.* (in press). The silk-HPPC is a hybrid photonic device composed of an inverse opal and a plasmonic crystal realized with a pure protein material substrate. In the transmission spectra, the silk-HPPC simultaneously exhibits both a pseudo-PBG and an extraordinary transmission (EOT). The SIO improves the response by the EOT as well as exhibiting a spectral response through the pseudo-PBG shift. Finite difference time domain (FDTD) simulations were performed to confirm the existence of the EOT of the HPPC structure. The response of the HPPC was experimentally evaluated by modulating the index contrast of the device with different refractive index fluids.

Figure 14:
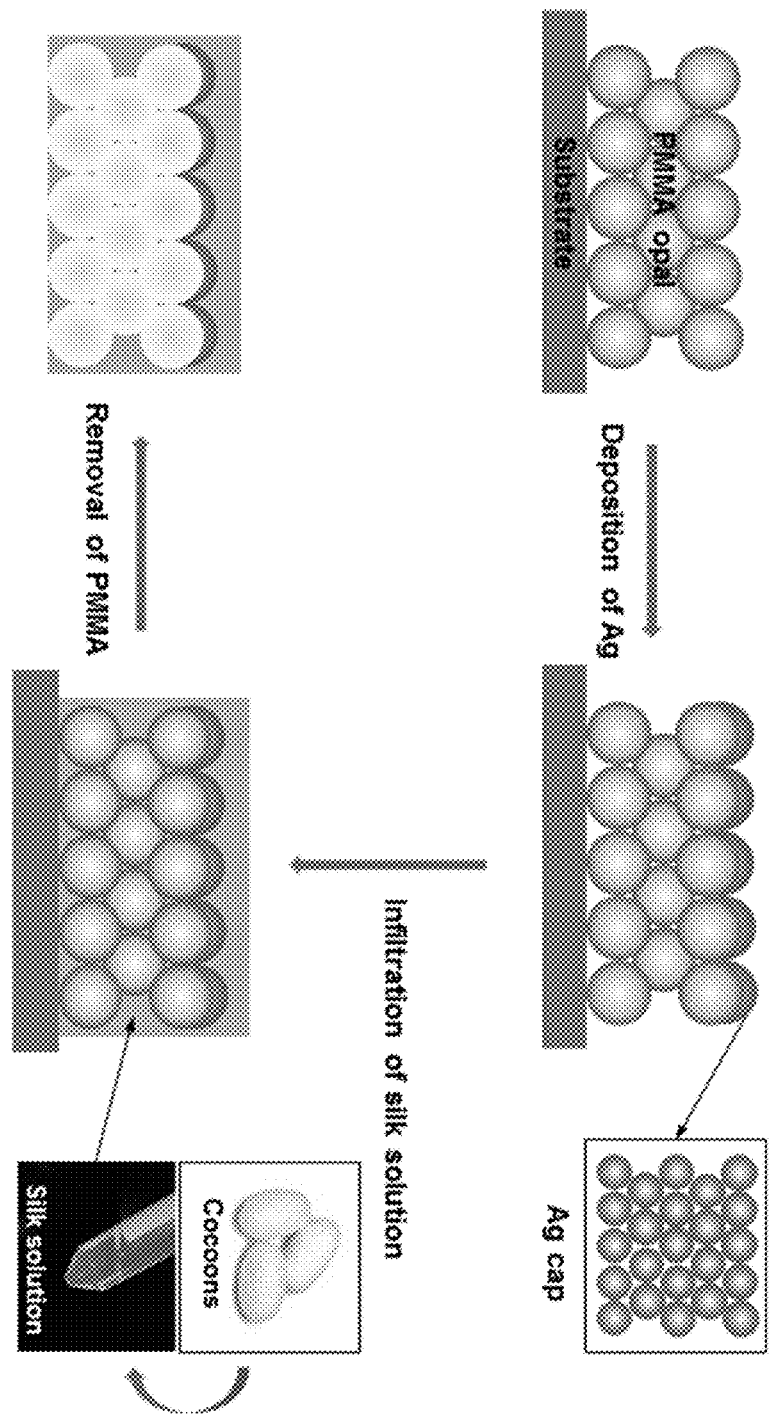
FIG. 14 provides a schematic illustration of the fabrication of hybrid photonic-plasmonic crystal (HPPC) composed of a biocompatible silk inverse opal (SIO) and a silver (Ag) cap.
Figure 15:
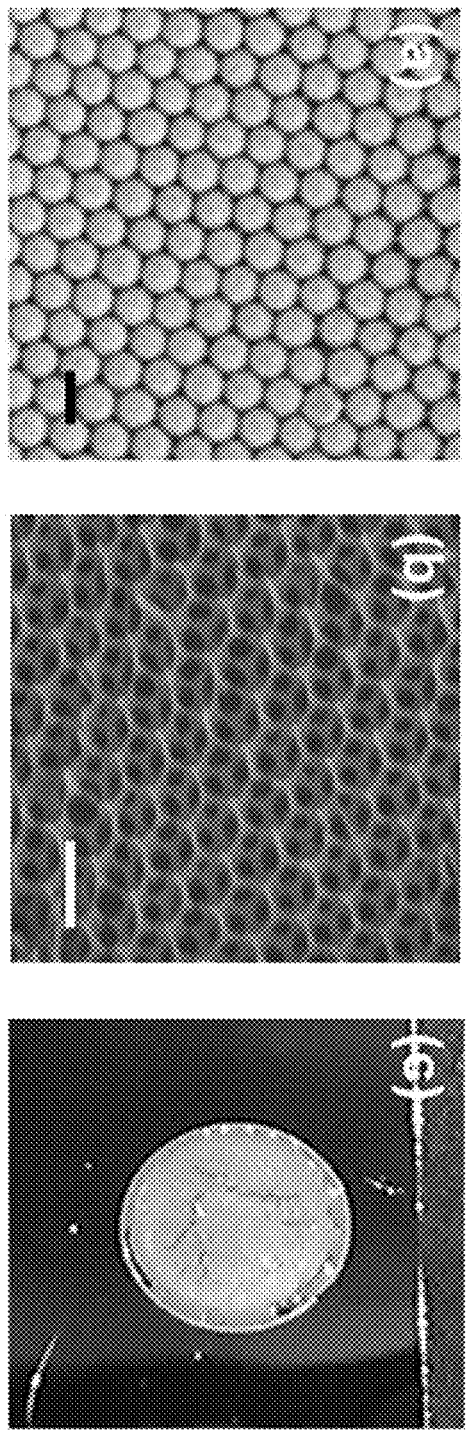
FIGS. 15 (a), (b) are SEM images of an Ag-deposited PMMA opal and an SIO; (c) is an optical image of the top view of the HPPC. Green irradiation originates from diffraction by the SIO. The scale bars in both (a) and (b) indicate 500 nm.
Figure 16:
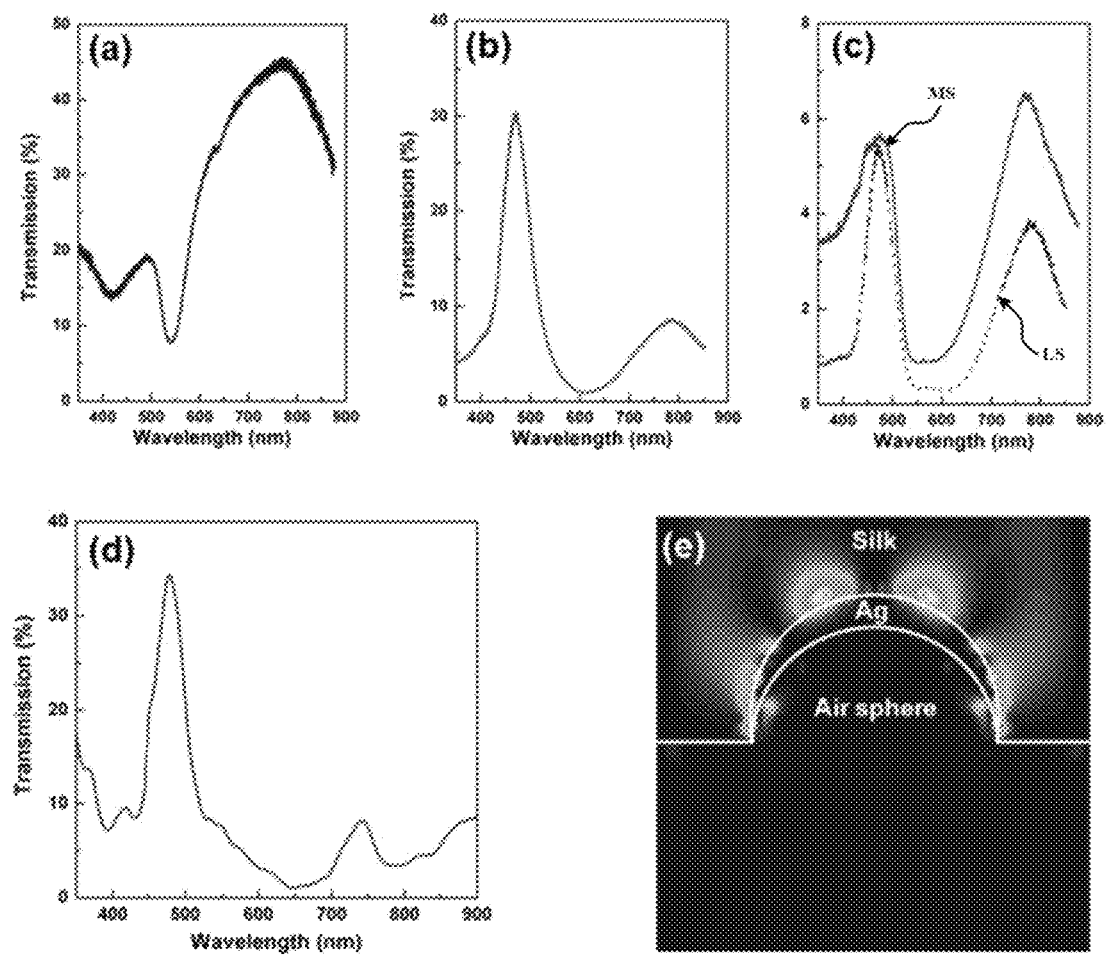
FIG. 16 depicts transmission spectra of (a) the bare opal, (b) the plasmonic crystal, and (c) the HPPC. By comparison, a linear superposition (black dots) of (b) and (c) is plotted in (c). (d) Calculated transmission spectrum for the plasmonic crystal. (e) Computed intensity of the magnetic field (perpendicular component to the image plane) associated with the resonance at 470 nm. The intensity is concentrated at the Ag/silk interface.
Figure 17:
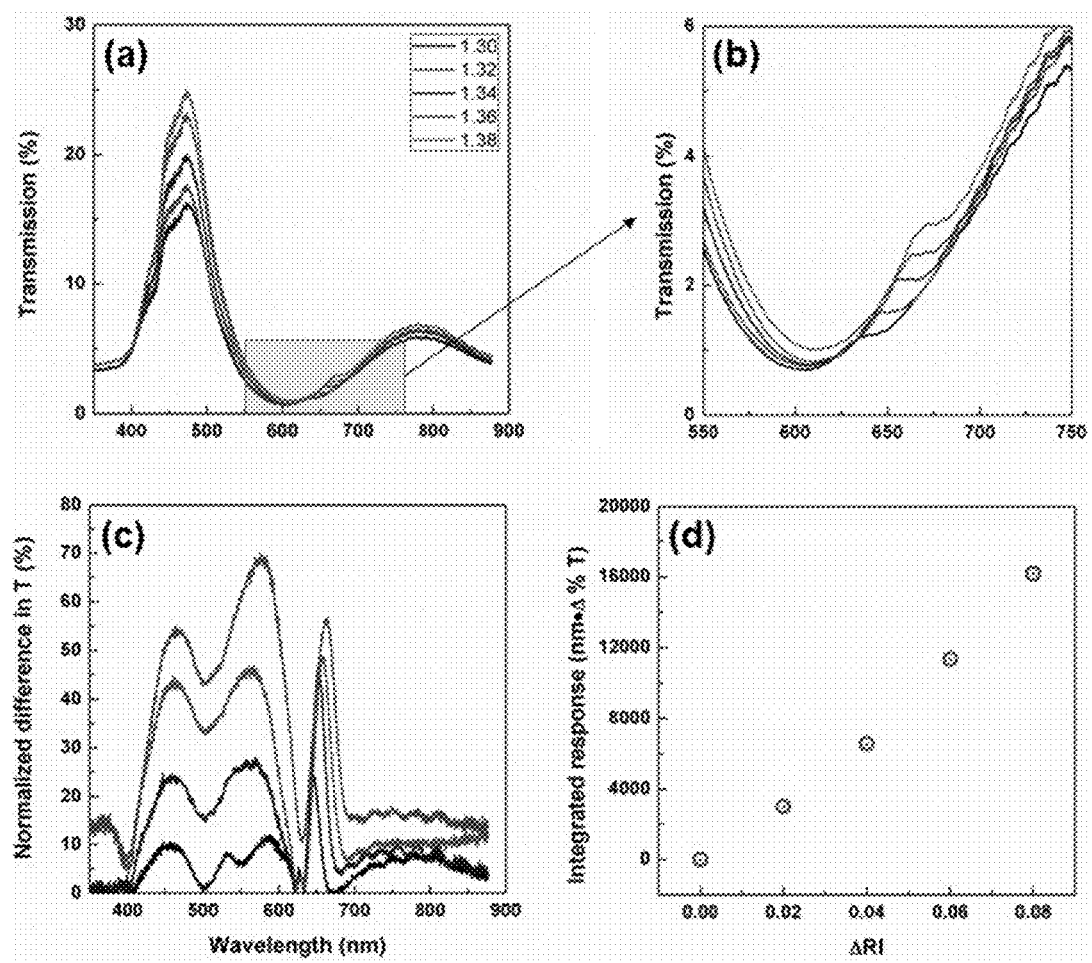
FIGS. 17(a-d) depict experimental results for RI sensing. (a) Transmission spectra of the HPPC structure immerged in analytes with different RI (inset) and (b) magnified spectra to appear a pseudo-PBG shift. (c) Normalized differences in transmission as a function of wavelength when the 1.30 of RI is base. The plot is evaluated at different RI; 1.32 (black), 1.34 (blue), 1.36 (cyan), and 1.38 (red). (d) Plot of the integrated response of the HPPC over a wavelength range of 350-850 nm as a function of the change in RI. From a linear fit of the plot in (b), the HPPC exhibits a sensitivity ≈200,000 nm·Δ% T/RIU (refractive index unit).

FIG. 14 shows the schematic diagram of the HPPC structure having a 3D SIO and a 2D plasmonic crystal. A PMMA-nanosphere opal with a diameter of 350-nm stacked on a silicon wafer was used as a template. A 70-nm-thick Ag film was subsequently deposited on the template thus coating one side of the photonic crystal. This process creates the plasmonic crystal by forming an array of nanoscale holes. Silk solution was then cast onto the metal-coated template yielding a free standing film. Finally, the PMMA nanospheres were removed by exposure to acetone. FIGS. 15(a) and 15(b) show scanning electron microscope (SEM) images that display the hexagonal array of voids in the metal layer and the ordered voids in the SIO. The SEM image of the SIO shows a slight contraction of the lattice constant that appears to have become smaller (300-nm) than the diameter of PMMA nanospheres. This is due to the prolonged exposure to acetone that induces contraction of the silk film. Green structural color corresponding to the pseudo PBG of the SIO appears in the finalized sample as shown in FIG. 15(c).

The spectral response of the transmission measurement was examined to analyze the photonic response of the HPPC. In order to address this, the transmission measurement of the bare SIO and the Ag-coated SIO (HPPC) in the visible and near-IR regions of the spectrum was conducted. FIG. 16(a) shows the transmission spectrum of the bare SIO. A dip at the wavelength of 542 nm corresponding to the PBG was clearly detected. According to the Bragg-Snell formula (further described in W. L. Vos, R. Sprik, A. Blaaderen, A. Imhof, A. Lagendijk, G. H. Wegdam, *Phys. Rev. B* 1996, 53, 16231, which is incorporated herein by reference in its entirety), the PBG position can be estimated through $$m\lambda_{Bragg}=2d_{111}\sqrt{n_{eff}^2-sin^2\theta}, \qquad (1)$$

where m is the diffraction order, $d_{111}$ is the inter-planar spacing in the (111) direction which is perpendicular to the film ($d_{111}$=0.8165D, D is the sphere's diameter), $\theta$ is the incidence angle from the normal, and $n_{eff}$ is the effective refractive index. The RI value of silk fibroin is used in the calculations is $n_{silk}$=1.54. The experimental result is in agreement with the PBG position estimated from Eq. 1. To investigate the response of the plasmonic crystal, the HPPC was infiltrated with fluid having index of refraction matched to the index of refraction of silk (e.g. n=1.54). By eliminating the RI contrast between the silk and air, the HPPC can be considered simply as a plasmonic crystal composed of the Ag-cap array. The measurement performed on the infiltrated HPPC shows the EOT peak induced by the silver nanohole array at 470 nm (FIG. 16(b)). The periodic metal structure creates spatially coherent plasmonic modes that induce a varied and complex response comprising Bloch wave SPR modes and Wood's anomalies.[24] The incident beam approaching the Ag film is diffracted by the 2D hexagonal grating in a series of SPR diffraction orders that can be described with the momentum conservation law (as set forth in B. Ding, M. E. Pemble, A. V. Korovin, U. Peschel, S. G. Romanov, *Phys. Rev. B* 2010, 82, 035119, which is incorporated herein by reference in its entirety):

$$k(\omega) = \pm\sqrt{k_{SPP}(\omega)^2 - \left\{\frac{2\pi}{\sqrt{2}\,a}(2j-i)\right\}^2} = \frac{2\pi j}{a}, \qquad (2)$$

$$(i, j) = 0, \pm 1, \pm 2, \ldots$$

where $$k_{SPP}(\omega) = \frac{2\pi}{\lambda}\sqrt{\frac{\varepsilon_d\varepsilon_m}{\varepsilon_d+\varepsilon_m}},$$

$\varepsilon_m$ and $\varepsilon_d$ are the dielectric constants of the Ag and the dielectric in contact with the Ag (e.g. silk and the material-filling air voids), a is the lattice constant of the nanoholes, and (i,j) are the SPR diffraction orders. The EOT wavelength corresponds to the (i, j)=($\bar{2}$, $\bar{1}$) diffraction order at the silk/Ag interface. FIG. 16(c) shows the measured spectrum (reference symbol MS) of the HPPC in air. By measuring the spectral response of the HPPC device, both EOT and PBG signatures were simultaneously detected. This measurement was also compared with the linear superposition (reference symbol LS) of the spectra taken from the photonic (FIG. 16(a)) and the plasmonic crystal (FIG. 16(b)). This comparison, shown in FIG. 16(c), illustrates that the response of the HPPC can be understood by considering the combined contributions of the photonic and plasmonic functions each components.

Three dimensional finite-difference time-domain (FDTD) simulations using MEEP were used to analyze the transmission and the electromagnetic field distribution in the plasmonic crystal (in accordance with methods set forth in A. F. Oskooi, D. Roundy, M. Ibanescu, P. Bermel, J. D. Joannopoulos, S. G. Johnson, Comp. Phys. Commun. 2010, 181, 687-702, which is incorporated herein by reference in its entirety). It is noted that the SIO has a smaller lattice constant than the plasmonic crystal because of slight contraction during processing, thus the unit cell in the simulation using the periodic boundary condition is an approximation that does not keep this mismatch into account. FIG. 16(d) shows the simulated transmission spectra of the plasmonic crystal. An especially strong transmission peak is found at λ=470 nm, which is in agreement with the EOT observed experimentally. The field profile supported at 470-nm corresponding to the EOT revealed high localization at the Ag/silk interface consistent with the results obtained from diffraction theory (FIG. 16(e)).

The spectral response is strongly influenced by changes in the refractive index of the surrounding environment. To characterize this, the HPPC structure was infiltrated with index matching fluids (1.30 to 1.38 with 0.02 differences). FIG. 17(a) shows the acquired transmission spectra for the HPPC as a function of different refractive indices. The measurement reveals two types of modes: red-shifting transmission-dips (FIG. 17(b)) around 650 nm that originate from a refractive index contrast modulation of the PBG of the SIO and increasing intensity of the EOT peaks at 470 nm. The EOT resonant wavelength is unaffected by changes in the analyte given the high field localization at the Ag/silk interface. However, changes in the analyte's index of refraction affect the transmitted intensity of the EOT, which was found to increase with increasing refractive index. The scattering loss of incident light is reduced due to the lower index contrast between the SIO and the analyte thereby increasing the intensity of the transmission spectra (in accordance with R. C. Schroden, M. Al-Daous, C. F. Blanford, A. Stein, Chem. Mater. 2002, 14, 3305-3315, which is incorporated herein by reference in its entirety). The combination of intensity increase of the EOT peak and wavelength shifts in the photonic bandgap affects the sensitivity of the device to refractive index changes.

Commonly used RI sensors typically monitor the response of a resonant spectral signature (see, e.g., A. Dahlin, M. Zach, T. Rindzevicius, M. Kall, D. S. Suterland F. Hook, J. Am. Chem. Soc. 2005, 127, 5043-5048; N. Ganesh, I. D. Block, B. T. Cunningham, Appl. Phys. Lett. 2006, 89, 023901; and P. Offermans, M. C. Schaafsma, S. R. K. Rodriguez, Y. Zhang, M. Crego-Calama, S. H. Brongersma, J. G. Rivas, J. G., ACS Nano 2011, 5, 5151-5157). However, a single peak analysis would not fully recapitulate the spectral response shown in the structure of the present example given the shifts and intensity-changes of the multiple resonant peaks that concomitantly occur in the HPPC. A multispectral analysis approach was adopted to account for this complex response with the ultimate intention of determining the sensitivity of the structure (in accordance with, e.g., M. E. Stewart, N. H. Mack, V. Malyarchuk, J. A. N. T. Soares, T. W. Lee, S. K. Gray, R. G. Nuzzo, J. A. Rogers, Proc. Nat. Acad. Soc., 2006, 103, 17143-17148, and J. Maria, T. T. Truong, J. Yao, T. W. Lee. R. G. Nuzzo, S. K. Gray, J. A. Rogers, J. Phys. Chem. C 2009, 113, 10493-10499, each of which is incorporated herein by reference in its entirety). The integrated response (R) over all wavelengths, including positive and negative differences in transmission spectra, can be defined by $$R = \int \left| \frac{T_{analyte} - T_{base}}{T_{base}} \right| d\lambda. \tag{3}$$

In Eq. 3, $T_{analyte}$ is the observed transmission from the HPPC when it is infiltrated with an index matching fluid, and $T_{base}$ is the transmission for the HPPC when the lowest RI fluid (e.g. n=1.30) is used. The integrand of Eq. 3 is the normalized difference in transmission relative to the base solution. The response R is directly related to the sensitivity of the device and would be actually improved by increasing the investigated bandwidth to cover resonances as many as the spectrometer allows, although there is a limitation that $T_{base}$ should have enough signal-intensity to be detected by the spectrometer with low signal-to-noise level since the extremely weak signal would induce large fluctuation in the integrand (see, e.g., J. Maria, T. T. Truong, J. Yao, T. W. Lee. R. G. Nuzzo, S. K. Gray, J. A. Rogers, J. Phys. Chem. C 2009, 113, 10493-10499, which is incorporated herein by reference in its entirety).

FIG. 17(c) shows the normalized transmission differences, obtained from the experimental transmission spectra. Note that the intensity changes at the EOT and the band-gap shifts induce strong transmission differences. The response R was integrated over a wavelength range from 350 to 850 nm, which covers the band of the white light source and the spectrometer. The device sensitivity can be defined as the slope of the integrated response as a function of the RI of the analyte (FIG. 17(d)) and achieve a sensitivity of 200,000 nm·Δ% T/RIU (refractive index unit) which is an order of magnitude higher than reported values from quasi-3D plasmonic crystal and nano-slit array in spite of the fact that the integrated wavelength-region of the present example was comparatively small (see, e.g., M. E. Stewart, N. H. Mack, V. Malyarchuk, J. A. N. T. Soares, T. W. Lee, S. K. Gray, R. G. Nuzzo, J. A. Rogers, Proc. Nat. Acad. Soc., 2006, 103, 17143-17148 and P. Y. Chung, K. L. Lee, G. Schultz, P. K. Wei, C. Batich, C., MRS Proc. 2010, 1253, 1253-K10-26). The simulated value for the quasi-3D plasmonic crystal was found to be 175,000 nm·Δ% T/RIU, which approached our experimental result despite the non-ideal simulation parameters (e.g. infinite structure, plane-wave, and polarized wave).[32] The response of the device found in this experimental analysis was governed by the interplay between the SIO and the plasmonic crystal. The sensitivity of the device may be improved by extending the measured wavelength-region to cover more than the EOT resonances and the pseudo-PBGs.

In summary, a silk-based HPPC structure and its application as a refractive index sensor were presented. The complex spectral response in transmission is a result of the interplay between the 2D plasmonic crystal and the 3D pseudo-PBG material, making the structure suited to multispectral RI sensing. The coexistence of the EOT and the band-gap shift in the sensor were experimentally and theoretically identified. The sensitivity obtained from the HPPC was found to be an order of magnitude higher than a comparable device based solely on a plasmonic crystal. Additional improvements may be provided to improve the sensitivity by expanding the interrogation bandwidth and by choosing EOT modes that are more sensitive to the RI change in wavelength and intensity. Furthermore, the HPPC may be cost-effectively fabricated and the properties of silk enable facile functionalization of the structure with biological dopants ultimately adding further utility to this approach by using the favorable biochemical properties of this all-protein material platform.

Experimental Parameters/Procedures

Silk Fibroin Preparation

Cocoons of the *Bombyx mori* silkworm were boiled for 30 minutes in a solution of 0.02M $Na_2CO_3$ to remove the sericin protein. The extracted fibroin was rinsed with distilled water and then dried in ambient air for 12 hours. After drying, the fibroin was dissolved in a 9.3M LiBr solution at 60° C. for 4 hours, yielding a 20 wt % aqueous solution, and subsequently the solution was dialyzed against distilled water using a dialysis cassette at room temperature for 48 hours until the solution reached a concentration of 8 wt %. The obtained solution was purified using a centrifuge and a 0.8 μm syringe filter.

Simulation

The FDTD simulations were performed using MEEP, which was developed by MIT. The periodic boundary condition was adapted to simulate in limited system resource. During the simulations, to get a field profile of the plasmonic mode, electromagnetic pulses were launched near a target nanostructure. For the transmission spectrum, a plane wave was launched in the lower plane with the distance of 1 μm from the HPPC (air region) and collected in the upper plane (silk region). A mesh size of 10 nm was employed and the refractive index of silk was set to be 1.54.

Measurement

All spectra in connection with this example were measured using a VIS/NIR fiber optic spectrometer (USB-2000, Ocean Optics). White light was propagated through the fiber and illuminated the HPPCs. The transmitted signal was coupled into the same fiber tip and went to the spectrometer. The distance between the fiber tip and sample was fixed at 500 μm. The reference signal was collected using an aluminum mirror. Fibers used in this study had 0.22 numerical apertures and 400 μm core diameters.

Example 3

Fluorescent Enhancement with a Quantum Dot-Doped Silk Photonic Crystal

Experiments in this Example demonstrate the utility of silk photonic crystals for photonic applications by exploring the use of doped (quantum dots and fluorescence) crystals.

Figure 19:
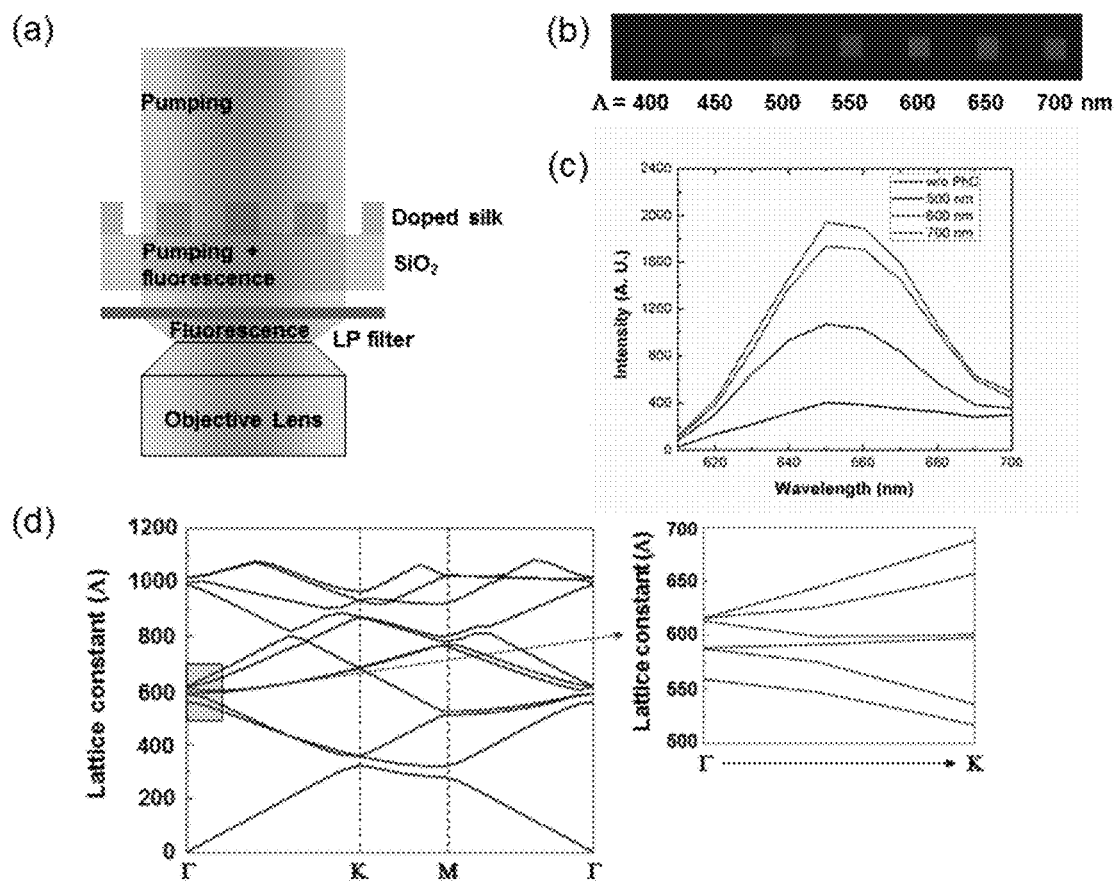
FIGS. 19a-d demonstrate utility of direct nano-patterning of silk fibroin films in enhancement of fluorescence emission. (a) Schematic of the fluorescence measurement is shown. (b) Multispectral CCD image of QD-doped silk PhC showing fluorescent enhancement, (c) Spectra obtained from PhC with a lattice constant of 500 nm, 600 nm, and 700 nm. As a control for comparison, an absorption spectrum of the doped silk without PhC is shown (w/o PhC). (d) Photonic band-structure of PhC calculated using the plane-wave expansion (PWE) method.

In this Example, the quantum-dots (QDs) were dispersed in an aqueous solution and were mixed into the silk fibroin solution at a concentration of 0.125 μM. The $SiO_2$ layer has a refractive index of 1.45, which being lower than silk (nsilk=1.54) guides photons into a silk-slab. Silk photonic crystals with lattice constants (Λ) ranging from 400-700 nm with 50 nm increments were generated. The sample was excited from top surface using a 480 nm LED and the fluorescent emission was collected by an objective lens as shown in FIG. 19*a*. The excitation light was blocked using a 610 nm long pass filter. The multispectral CCD image and spectra of the patterns are shown in FIGS. 19*b-c*. A 5-fold increase in intensity as shown in FIG. 19*b* was observed despite the low refractive index contrast between the silk (1.54) and air (1.00) on the silk photonic crystals with a 600 nm Λ.

Further in this Example, a two dimensional photonic band-structure as shown in FIG. 19*d* was calculated by a plane-wave expansion (PWE) method, in order to analyze the enhancement of fluorescence. The silk photonic crystal supported the leaky resonant modes with a low quality (Q) factor at the frequencies (Λ/λ), corresponding to Λ=550-650 nm at the fixed wavelength of 650 nm. The lattice constants calculated from the band-structure could be related to the actual silk photonic crystal structure that showed the fluorescence enhancement. The effect of the leaky modes that overlap the emission bandwidth of the QDs could be related to the enhanced extraction phenomena where a low Q-factor of the leaky mode could be beneficial, as the coupled radiation could be scattered faster whereas the coupling of the lossy radiation could be limited.

Example 4

Fluorescent Enhancement with a Biological Protein-Material System

Experiments in this Example demonstrate that a fully biological-material system composed of silk fibroin and the super folder GFP (sfGFP) variant show fluorescent enhancement.

Figure 20:
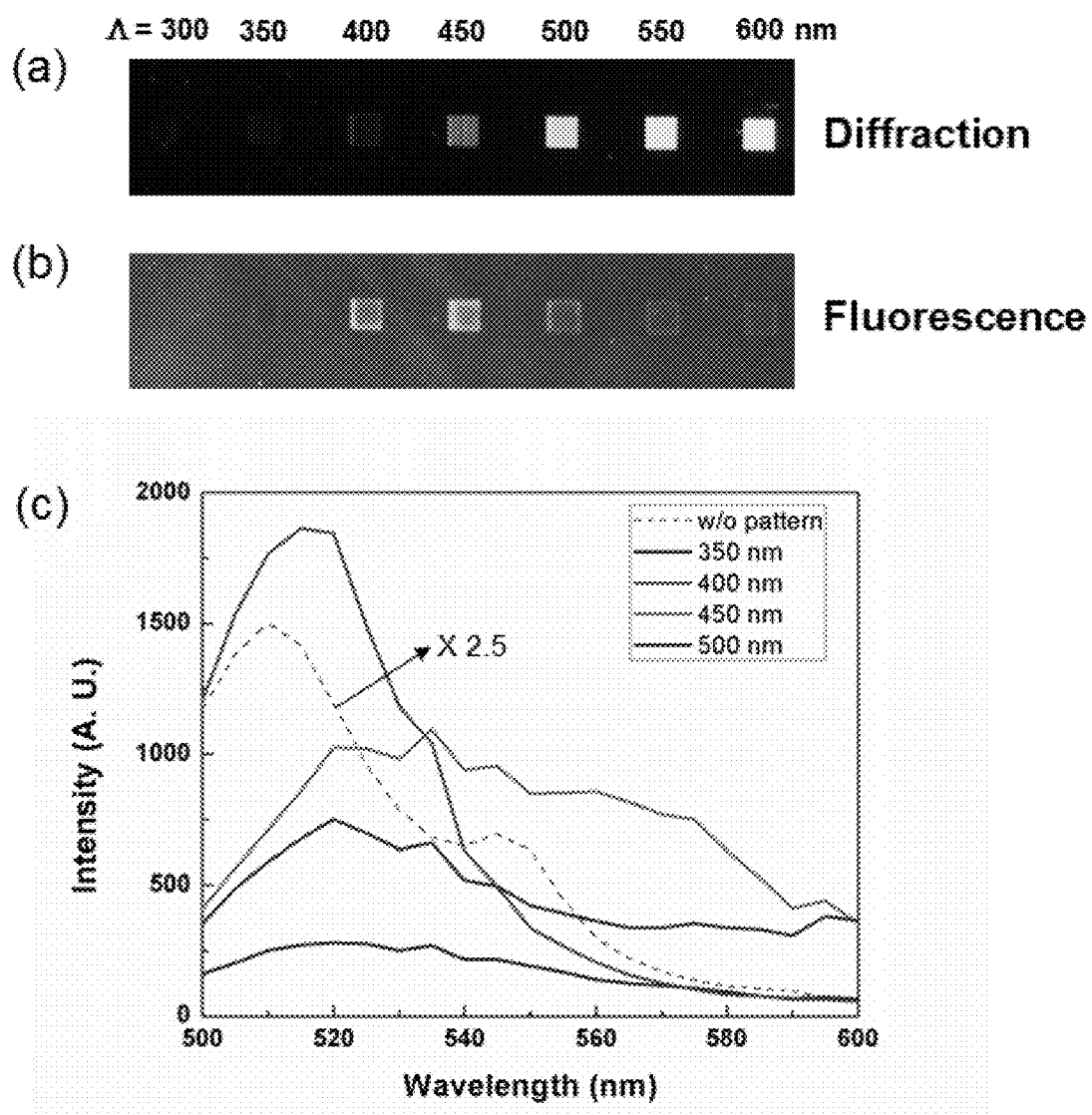
FIGS. 20a-c illustrate fluorescent enhancement with a fully biological protein-material system. (a)-(b) Multispectral CCD (dark-field microscopic and fluorescence) images of a green fluorescent protein (GFP) doped silk fibroin PhC under white light and laser illumination. (c) Spectra obtained from the PhCs showing the enhancement in fluorescence emission.

In this Example, devices were fabricated with a GFP-doped silk solution (1 mM concentration). The fluorescent protein dopants are ideal for biosensor applications due to high quantum yield, high extinction coefficient, and the high resistance against denaturing through solvent, pH, high temperature or photo bleaching. Fluorescent proteins are also extremely stable due to the dense beta sheet barrel protein structure encapsulating the chromophore. Multispectral CCD images of the GFP doped silk photonic crystals under white light illumination and 488 nm laser illumination are shown in FIGS. 20*a-b*. The lattice constants (Λ) of the silk photonic crystals ranged from 300 to 600 nm with 50 nm increments.

In this Example, the highest fluorescence enhancement, corresponded with the leaky band-edge modes from the silk photonic crystal structures with lattice constants (Λ of 400 and 450 nm. The observed spectral responses from fluorescent enhancement and by diffraction were similar. The spectra shown in FIG. 4*c* indicated the fluorescent enhancement of the sfGFP doped silk fibroin silk photonic crystals. The enhanced fluorescent peaks were found to shift with changing lattice constants and this shift was attributed to the wide fluorescent peak of GFP spectrum.

Example 5

Enhanced Singlet Oxygen Production by SIO-Phorphyrin

The rise in bacterial resistance to antibiotics calls for new antibacterial strategies. Photodynamic therapy of bacteria utilizes the use of light in combination with a photosensitizer to induce a phototoxic reaction, much like the use of photodynamic therapy for cancer [1]. Porphyrins are commonly used as a photosensitizer that can produce reactive oxygen upon exposure to light. Here we apply the porphyrin-doped silk inverse opal (SIO) to build a new kind of a photo-antimicrobial film that can kill *Staphylococcus aureus*

(*S. aureus*) bacteria, a gram positive bacterium. The band-edge effect shown in the SIO enhances the absorption of light, thereby amplifying the generation of singlet oxygen from porphyrin. This proof-of-concept experiment would suggest developing new treatment alternative to the standard antibiotic treatment for skin infections.

Figure 21:
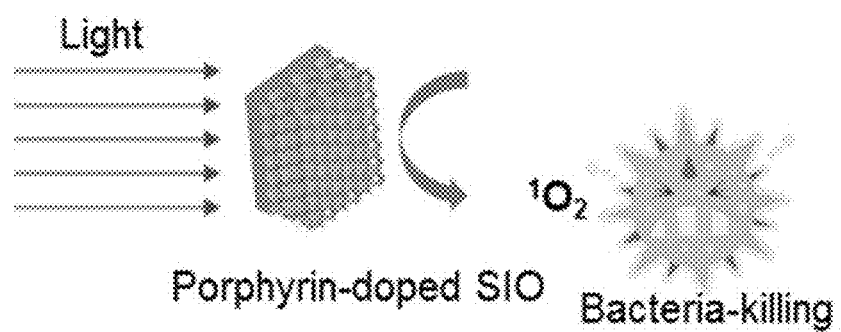
FIG. 21 provides a schematic diagram of photodynamic bacteria killing
Figure 22:
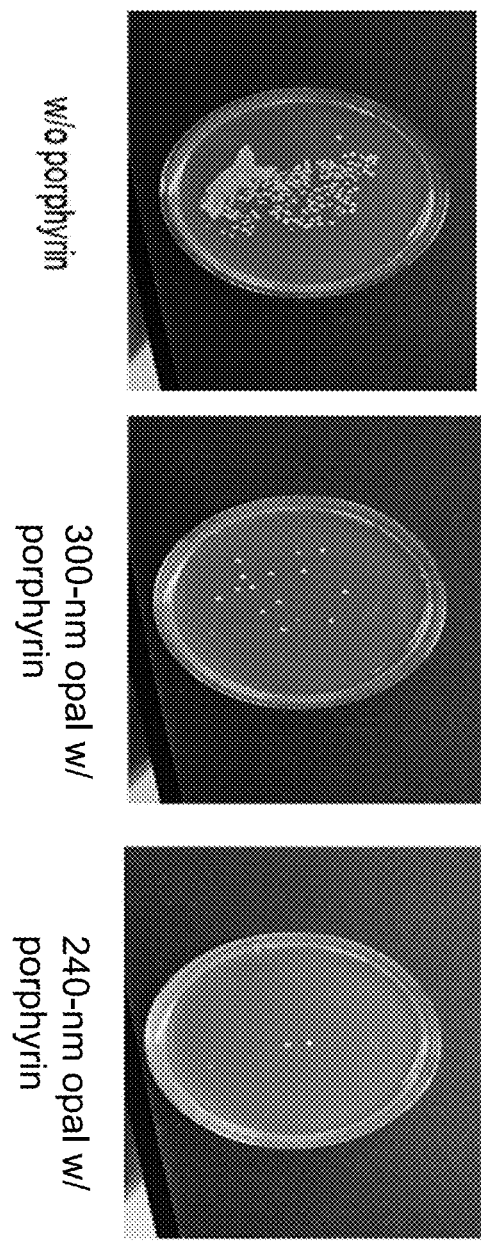
FIG. 22 provides photographs of the incubated agar plate for without porphyrin (left), with the 300-nm opal (middle), and the 240-nm opal (right).
Figure 23:
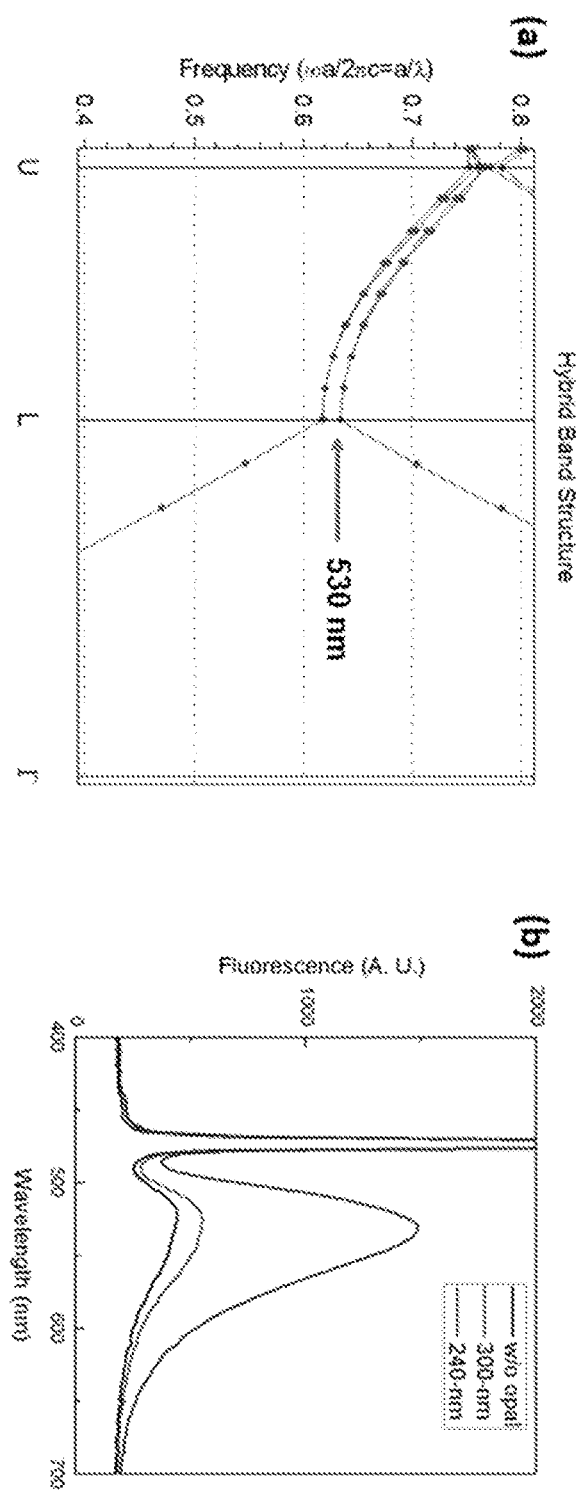
FIG. 23 (a) A photonic band-structure of the SIO. The upper band-edge at L-point corresponds to the wavelength of 530 nm when with the 240 nm opal. (b) Fluorescence of a singlet oxygen reagent.

FIG. 21 shows a schematic diagram of experiment. We doped water-soluble porphyrin (5,10,15,20-Tetrakis(1-methyl-4-pyridinio)porphyrin tetra(p-toluenesulfonate)) into the SIO by mixing two solutions (porphyrin and silk). Details to fabricate the opal described in Ref. 2. To investigate the band-edge effect, two opals with different lattice constant (240 and 300 nm) were fabricated and *S. aureus* solution was dropped on the SIO. A 532-nm green laser was illuminated with the power of 10 mW for 10 minutes. After the photodynamic killing, we spread the bacteria solution onto an agar plate. The agar plate was incubated for 24 hours to grow the survived bacteria.

Colony counting from FIG. 21 shows that the porphyrin opal kills more bacteria when it is compared with a reference which was illuminated without porphyrin. Especially, the 240-nm opal reveals more effective antibacterial activity than the 300 nm opal. From the band-structure shown in FIG. 3a, since the band-edge of the 240 nm opal is matched with the wavelength of the green laser, the opal can amplify the generation of the singlet oxygen. This phenomenon was confirmed by the use of a detection reagent that is highly selective for singlet oxygen (FIG. 3b). Consistent with this observation, the 240-nm opal shows high fluorescent emission, indicating there are more singlet oxygen molecules generated.

We demonstrate a new photo-antimicrobial film composed of silk fibroin and porphyrin. Integrated SIO enhance the absorption of light by tuning the band-edge frequency to the illumination. The nanophotonic-effect provides a means for developing new types of structure for improved photodynamic therapy.

REFERENCE

1. T. Maisch, J. Baier, B. Franz, M. Maier, M. Landthaler, R. M. Szeimies, and W. Baumler, "The role of singlet oxygen and oxygen concentration in photodynamic inactivation of bacteria," *PNAS* 104, 7223 (2007).
2. S. Kim, A. N. Mitropoulos, J. D. Spitzberg, H. Tao, D. L. Kaplan, and F. G. Omenetto, "Silk inverse opals," *Nature Photon.* 6, 818 (2012).

What is claimed is:

1. An apparatus comprising:
a silk photonic crystal, the crystal comprising nanoscale periodic structures that exhibit structural color when they are exposed to incident electromagnetic radiation; and
a light responsive entity that responds when it is exposed to electromagnetic radiation, wherein the electromagnetic radiation elicits a light induced effect,
wherein the light responsive entity is coupled to the silk photonic crystal,
wherein the nanoscale periodic structures are arranged and constructed so that electromagnetic frequencies at the silk photonic crystal's band gap edge substantially overlap with those electromagnetic frequencies that elicit the light-induced effect in the light responsive entity, so that when the photonic crystal is exposed to incident radiation it exhibits structural color, the light-responsive entity is exposed to the exhibited structural color, the elicited light-induced effect in the light responsive entity is amplified and/or enhanced by the exhibited structural color.

2. The apparatus of claim 1, wherein the silk photonic crystal is a silk inverse opal.

3. The apparatus of claim 2, wherein the silk inverse opal has a lattice constant in a range of between about 200 nm and about 600 nm.

4. The apparatus of claim 2, wherein the silk inverse opal has a face-centered cubic structure.

5. The apparatus of claim 2, wherein the light responsive entity comprises a metallic layer on the silk inverse opal.

6. The apparatus of claim 5, wherein the metallic layer is on an interior surface of the silk inverse opal.

7. The apparatus of claim 5, wherein the metallic layer comprises a metal, wherein the metal is selected from the group consisting of transition metals, post-transition metals, alkali metals, alkaline earth metals, lanthanides, actinides and combinations thereof.

8. The apparatus of claim 5, wherein the metallic layer is between about 40 nm and about 100 nm thick.

9. The apparatus of claim 1, wherein the electromagnetic frequencies at the band gap edge are between about 450 nm and about 550 nm.

10. The apparatus of claim 1, wherein the range of electromagnetic frequencies that induce a light-induced effect in the light responsive entity is from about 300 nm to about 600 nm.

11. The apparatus of claim 1, wherein the light-induced effect is selected from the group consisting of absorption, excitation, emission, refraction, heating, chemical reaction, and combinations thereof.

12. The apparatus of claim 1, wherein the light responsive entity is selected from the group consisting of: a plasmonic material, a photosensitizer, quantum dots, a fluorescent entity and combinations thereof.

13. The apparatus of claim 12, wherein the photosensitizer is selected from the group consisting of porphyrins, chlorophylls, dyes and combinations thereof.

14. The apparatus of claim 12, wherein the plasmonic materials comprise plasmonic nanoparticles.

15. The apparatus of claim 14, wherein the plasmonic nanoparticles comprise metallic nanoparticles.

16. The apparatus of claim 15, wherein the metallic nanoparticles are gold.

17. The apparatus of claim 12, wherein the plasmonic materials comprise plasmonic crystals.

18. The apparatus of claim 12, wherein the plasmonic materials comprise at least one metal or an alloy, or is doped with at least one metal or alloy.

19. The apparatus of claim 18, wherein the at least one metal is a noble metal or non-noble metal.

20. The apparatus of claim 19, wherein the noble metal is or comprises gold, silver, ruthenium, rhodium, palladium, osmium, iridium, platinum, or mercury.

21. The apparatus of claim 19, wherein the non-noble metal is or comprises titanium, aluminum, nickel, fluorine, cerium, tin, bismuth, antimony, molybdenum, chromium, cobalt, zinc, tungsten, polonium, rhenium and copper.

22. The apparatus of claim 12, wherein the plasmonic materials comprise an oxide or oxides of at least one noble or non-noble metal.

23. The apparatus of claim 12, wherein the plasmonic materials comprise silica or silk fibroin doped with rare earth emitters, such as Pr+3, Er+3, or Nd+3.

24. The apparatus of claim 12, wherein the plasmonic materials comprise an alloy or alloys of at least one noble or non-noble metal.

25. The apparatus of claim 12, wherein the plasmonic materials comprise a nonhomogeneous mixture of metals.

26. A method of forming the apparatus of claim 1, comprising:
   preparing a silk fibroin solution;
   inducing a plurality of spherical units to self-assemble into a lattice;
   applying the silk fibroin solution to the lattice such that the silk fibroin solution fills voids between the plurality spherical units;
   separately or as a part of the silk fibroin solution, applying a light responsive entity to the lattice;
   drying the silk fibroin solution into a silk film; and
   removing the plurality of spherical units.

27. The method of claim 26, wherein the step of inducing comprises:
   casting a solution with the plurality of spherical units onto a silicon wafer, wherein the spherical units comprise poly(methyl methacrylate); and
   applying heat to the silicon wafer.

28. The method of claim 26, wherein drying the silk fibroin solution into the silk film comprises:
   drying the silk fibroin solution for twenty four hours at room temperature.

29. The method of claim 26, wherein removing the plurality of spherical units comprises:
   soaking the silk film and the lattice of the plurality of spherical units in a solvent.

30. The method of claim 26, wherein the light responsive entity is selected from the group consisting of a plasmonic material, plasmonic nanoparticles, a photosensitizer, quantum dots, a fluorescent entity, a metallic layer on the lattice and combinations thereof.

31. The method of claim 26, further comprising:
   immersing the silk film in a substance to alter the photonic band gap of the apparatus.

* * * * *

SEQUENCE LISTING

```
<160> NUMBER OF SEQ ID NOS: 22

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(90)
<223> OTHER INFORMATION: Wherein any of residues 7-90 may be missing.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Gly Ala Gly Ser Gly Ala Gly Ala
        50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90

<210> SEQ ID NO 2
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is V, I or A.
<220> FEATURE:
<221> NAME/KEY: MISC_FEATURE
<222> LOCATION: (3)..(30)
```

<223> OTHER INFORMATION: Wherein any of residues 3-30 may be missing.

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Bombyx mori

<400> SEQUENCE: 3

Gly Ala Ala Ser
1

<210> SEQ ID NO 4
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (14)..(15)
<223> OTHER INFORMATION: Wherein any of residues 14-15 may be missing

<400> SEQUENCE: 4

Ser Ser Ala Ala Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: Wherein any of residues 2-5 may be missing
<220> FEATURE:
<221> NAME/KEY: MISC_FEATURE
<222> LOCATION: (2)..(5)
<223> OTHER INFORMATION: Wherein X is any residue
<220> FEATURE:
<221> NAME/KEY: MISC_FEATURE
<222> LOCATION: (8)..(8)
<223> OTHER INFORMATION: Wherein X is any residue

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is A, S, Y, R, D, V or W -continued

```
<400> SEQUENCE: 6

Gly Gly Gly Xaa
1

<210> SEQ ID NO 7
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (4)..(6)
<223> OTHER INFORMATION: Wherein any residues 4-6 may be missing

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Galleria mellonella

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is L, I, V or P
<220> FEATURE:
<221> NAME/KEY: MISC_FEATURE
<222> LOCATION: (5)..(5)
<223> OTHER INFORMATION: Wherein X is L, I, V or P

<400> SEQUENCE: 9

Gly Xaa Gly Gly Xaa Gly
1               5

<210> SEQ ID NO 10
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Wherein X is Y, V, S or A
<220> FEATURE:
<221> NAME/KEY: MISC_FEATURE
<222> LOCATION: (6)..(20)
<223> OTHER INFORMATION: Wherein any of 6-20 may be missing
<220> FEATURE:
<221> NAME/KEY: MISC_FEATURE
<222> LOCATION: (10)..(10)
<223> OTHER INFORMATION: Wherein X is Y, V, S or A
<220> FEATURE:
<221> NAME/KEY: MISC_FEATURE
```

```
<222> LOCATION: (15)..(15)
<223> OTHER INFORMATION: Wherein X is Y, V, S or A
<220> FEATURE:
<221> NAME/KEY: MISC_FEATURE
<222> LOCATION: (20)..(20)
<223> OTHER INFORMATION: Wherein X is Y, V, S or A

<400> SEQUENCE: 10

Gly Pro Gly Gly Xaa Gly Pro Gly Gly Xaa Gly Pro Gly Gly Xaa Gly
1               5                   10                  15

Pro Gly Gly Xaa Tyr
            20

<210> SEQ ID NO 11
<211> LENGTH: 5
<212> TYPE: PRT
<213> ORGANISM: Argiope trifasciata

<400> SEQUENCE: 11

Gly Arg Gly Gly Ala
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(10)
<223> OTHER INFORMATION: Wherein any of 5-10 may be missing

<400> SEQUENCE: 12

Gly Ala Gly Ala Ala Ala Ala Ala Ala Gly Gly Ala
1               5                   10

<210> SEQ ID NO 13
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Wherein X is Q, Y, L, A, S or R
<220> FEATURE:
<221> NAME/KEY: MISC_FEATURE
<222> LOCATION: (5)..(5)
<223> OTHER INFORMATION: Wherein X is Q, Y, L, A, S or R
<220> FEATURE:
<221> NAME/KEY: MISC_FEATURE
<222> LOCATION: (7)..(7)
<223> OTHER INFORMATION: Wherein X is Q, Y, L, A, S or R
<220> FEATURE:
<221> NAME/KEY: MISC_FEATURE
<222> LOCATION: (8)..(8)
<223> OTHER INFORMATION: Wherein X is Q, Y, L, A, S or R

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Bombyx mori

<400> SEQUENCE: 14
```

-continued

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Bombyx mandarina

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Antheraea mylitta

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Antheraea yamamai

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Galleria mellonella

<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Nephila madascariensis

<400> SEQUENCE: 19

Thr Thr Ile Ile Glu Asp Leu Asp Ile Thr Ile Asp Gly Ala Asp Gly
1               5                   10                  15

Pro Ile

<210> SEQ ID NO 20
<211> LENGTH: 8
<212> TYPE: PRT
<213> ORGANISM: Major ampullata

<400> SEQUENCE: 20

Thr Ile Ser Glu Glu Leu Thr Ile
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic polypeptide

```
<400> SEQUENCE: 21

Gly Ser Gly Ala Gly Ala
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(5)
<223> OTHER INFORMATION: Wherein X is any residue

<400> SEQUENCE: 22

Gly Pro Gly Xaa Xaa
1               5
```